(12) United States Patent
Ogihara et al.

(10) Patent No.: US 9,075,309 B2
(45) Date of Patent: *Jul. 7, 2015

(54) SILICON-CONTAINING SURFACE MODIFIER, RESIST UNDERLAYER FILM COMPOSITION CONTAINING THIS, AND PATTERNING PROCESS

(71) Applicant: SHIN-ETSU CHEMICAL CO., LTD., Tokyo (JP)

(72) Inventors: Tsutomu Ogihara, Jyoetsu (JP); Takafumi Ueda, Jyoetsu (JP); Yoshinori Taneda, Jyoetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,154

(22) Filed: Jan. 22, 2013

(65) Prior Publication Data

US 2013/0210236 A1 Aug. 15, 2013

(30) Foreign Application Priority Data

Feb. 14, 2012 (JP) ................................ 2012-029228

(51) Int. Cl.
| | | |
|---|---|---|
| G03F 7/075 | (2006.01) | |
| G03F 7/09 | (2006.01) | |
| G03F 7/11 | (2006.01) | |
| G03F 7/36 | (2006.01) | |
| G03F 7/40 | (2006.01) | |
| H01L 21/302 | (2006.01) | |
| C07F 7/18 | (2006.01) | |
| C09D 183/06 | (2006.01) | |
| C08G 77/14 | (2006.01) | |

(52) U.S. Cl.
CPC ............ *G03F 7/0752* (2013.01); *G03F 7/0757* (2013.01); *H01L 21/302* (2013.01); *G03F 7/0751* (2013.01); *G03F 7/11* (2013.01); *G03F 7/36* (2013.01); *G03F 7/40* (2013.01); *C07F 7/1836* (2013.01); *C09D 183/06* (2013.01); *G03F 7/094* (2013.01); *C07F 7/184* (2013.01); *C08G 77/14* (2013.01)

(58) Field of Classification Search
None
See application file for complete search history.

(56) References Cited

U.S. PATENT DOCUMENTS

| | | | |
|---|---|---|---|
| 4,510,136 A | 4/1985 | Moberg | |
| 4,902,603 A | 2/1990 | Slater et al. | |
| 5,178,989 A | 1/1993 | Heller et al. | |
| 5,508,358 A | 4/1996 | Ono et al. | |
| 5,632,910 A | 5/1997 | Nagayama et al. | |
| 7,651,829 B2 | 1/2010 | Hamada et al. | |
| 2001/0016635 A1 | 8/2001 | Evain et al. | |
| 2002/0187422 A1 | 12/2002 | Angelopoulos et al. | |
| 2003/0191268 A1* | 10/2003 | Iwasawa et al. ................. 528/10 |
| 2003/0235786 A1 | 12/2003 | Krishnamurthy et al. | |
| 2004/0058275 A1 | 3/2004 | Neef et al. | |
| 2004/0241579 A1 | 12/2004 | Hamada et al. | |
| 2005/0048395 A1 | 3/2005 | Kobayashi et al. | |
| 2005/0112383 A1 | 5/2005 | Tanaka et al. | |
| 2006/0019195 A1 | 1/2006 | Hatakeyama et al. | |
| 2006/0024980 A1 | 2/2006 | Tsuchiya et al. | |
| 2006/0040206 A1 | 2/2006 | Nakashima et al. | |
| 2007/0134916 A1 | 6/2007 | Iwabuchi et al. | |
| 2007/0178318 A1 | 8/2007 | Tanaka et al. | |
| 2007/0203275 A1 | 8/2007 | Kikuchi et al. | |
| 2007/0231738 A1 | 10/2007 | Kaneko et al. | |
| 2007/0238300 A1 | 10/2007 | Ogihara et al. | |
| 2008/0026322 A1 | 1/2008 | Ogihara et al. | |
| 2009/0011366 A1 | 1/2009 | Tsubaki et al. | |
| 2009/0136869 A1 | 5/2009 | Ogihara et al. | |
| 2010/0040972 A1 | 2/2010 | Tarutani et al. | |

(Continued)

FOREIGN PATENT DOCUMENTS

| | | |
|---|---|---|
| EP | 1 628 160 A2 | 2/2006 |
| EP | 1 798 599 A1 | 6/2007 |

(Continued)

OTHER PUBLICATIONS

Jun. 13, 2013 European Search report issued in European Patent Application No. EP 13000599.4.

(Continued)

*Primary Examiner* — Sin Lee
(74) *Attorney, Agent, or Firm* — Oliff PLC

(57) ABSTRACT

The present invention provides a silicon-containing surface modifier wherein the modifier contains one or more of a repeating unit shown by the following general formula (A) and a partial structure shown by the following general formula (C). The present invention has an object to provide a resist underlayer film applicable not only to a negatively developed resist pattern formed by a hydrophilic organic compound but also to a conventional positively developed resist pattern formed by a hydrophobic compound.

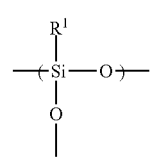

(A)

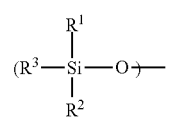

(C)

22 Claims, 1 Drawing Sheet

(56) References Cited

U.S. PATENT DOCUMENTS

| | | |
|---|---|---|
| 2010/0041805 A1 | 2/2010 | Amidaiji et al. |
| 2010/0086872 A1 | 4/2010 | Ogihara et al. |
| 2012/0276483 A1 | 11/2012 | Ogihara et al. |
| 2013/0005150 A1 | 1/2013 | Ogihara et al. |
| 2013/0045601 A1 | 2/2013 | Ogihara et al. |
| 2013/0101942 A1 | 4/2013 | Tanaka et al. |

FOREIGN PATENT DOCUMENTS

| | | |
|---|---|---|
| EP | 1 845 132 A2 | 10/2007 |
| EP | 2 103 655 A1 | 9/2009 |
| EP | 2 138 898 A1 | 12/2009 |
| EP | 2 172 808 A1 | 4/2010 |
| EP | 2 500 775 A2 | 9/2012 |
| EP | 2 518 562 A2 | 10/2012 |
| EP | 2 540 780 A1 | 1/2013 |
| JP | A-07-181688 | 7/1995 |
| JP | A-07-183194 | 7/1995 |
| JP | A-11-258813 | 9/1999 |
| JP | A-2000-053921 | 2/2000 |
| JP | A-2004-153125 | 5/2004 |
| JP | A-2005-128509 | 5/2005 |
| JP | A-2005-173552 | 6/2005 |
| JP | A-2005-520354 | 7/2005 |
| JP | A-2005-537502 | 12/2005 |
| JP | A-2006-508377 | 3/2006 |
| JP | A-2006-251369 | 9/2006 |
| JP | A-2006-317864 | 11/2006 |
| JP | A-2007-199653 | 8/2007 |
| JP | A-2007-226170 | 9/2007 |
| JP | A-2007-297590 | 11/2007 |
| JP | A-2007-302873 | 11/2007 |
| JP | A-2008-281974 | 11/2008 |
| JP | A-2008-281980 | 11/2008 |
| JP | 2009-025707 A | 2/2009 |
| JP | A-2009-053657 | 3/2009 |
| JP | A-2009-126940 | 6/2009 |
| JP | A-2010-085893 | 4/2010 |
| JP | B2-4716037 | 7/2011 |
| JP | 2013-083964 A | 5/2013 |
| TW | 2008-06746 | 2/2008 |
| WO | WO 2004/007192 A1 | 1/2004 |
| WO | WO 2011/105368 A1 | 9/2011 |

OTHER PUBLICATIONS

Jan. 6, 2015 Office Action issued in Japanese Patent Application No. 2012-029228.
Oct. 9, 2012 Extended European Search Report issued in European Patent Application No. 12004626.3.
Jul. 23, 2014 Office Action issued in European Patent Application No. 12 004 626.3.
Aug. 19, 2014 Notification of Reasons for Refusal issued in Japanese Patent Application No. 2011-220708 (with partial translation).
Database CA [Online], Ogihara et al., "A Patterning Process," Oct. 31, 2012, XP002698566.
Database Reaxys [Online], Sumitomo Chemical Company, Limited, "Organic Silicon-Based Compound and Method of Producing the Same," Aug. 30, 2007, XP002698567.
Temtsin et al., "Aromatic PMOs: tolyl, xylyl and dimethoxyphenyl groups integrated within the channel walls of hexagonal mesoporous silicas," *Journal of Materials Chemistry*, vol. 11, No. 12, Oct. 23, 2001, pp. 3202-3206.
Database Reaxys [Online], Manoso et al., "Improved Synthesis of Aryltrialkoxysilanes via Treatment of Aryl Grignard or Lithium Reagents with Tetraalkyl Orthosilicates," 2004, XP002698568.
Database Reaxys [Online], Seganish et al., "Efforts Directed toward the Synthesis of Colchicine: Application of Palladium-Catalyzed Siloxane Cross-Coupling Methodology," 2005, XP002698569.
Database CA [Online], Moberg, William K., "Fungicidal 1-(silylmethyl)-1,2,4-triazole derivatives," 1986, XP002698570.
Database Ca [Online], Virtanen et al., "Organosilane and their hydrolytic polymers as surface treatment agents for use in chromatography and electronics," 1987, XP002698571.
Database CA [Online], Harkonen et al., "External silane donors in Ziegler-Natta catalysis. An approach to the optimum structure of the donor," 1991, XP002698572.
Database CA [Online], O'Dell, R., "A convenient synthesis of arylhis (ethyltrifluorosiliconate)s," 1995, XP002698573.
Database CA [Online], Evain et al., "Alpha-olefin polymerization catalyst system containing an aromatic silane compound," 2001, XP002698574.
Jun. 24, 2013 Extended European Search Report issued in European Application No. 13002020.9.
Oct. 9, 2014 Office Action issued in European Patent Application No. 13002020.9.
Patai, S. et al., "The Chemistry of Organic Silicon Compounds," 1989, John Wiley & Sons, pp. 909-916.
Aug. 12, 2013 Extended European Search Report issued in European Application No. 12002878.2.
Jan. 20, 2014 Taiwanese Office Action issued in Taiwanese Patent Application No. 101115187 (with partial English-language translation).
Jun. 19, 2013 Extended European Search Report issued in European Patent Application No. EP 13 00 0600.0.
May 20, 2014 Office Action issued in Japanese Patent Application No. 2012-029230 (with partial translation).
U.S. Appl. No. 14/107,841 in the name of Ogihara et al., filed Dec. 16, 2013.
Maenhoudt et al., "Double Patterning scheme for sub-0.25 k1 single damascene structures at NA=0.75, λ=193nm", *Proceedings of SPIE*, 2005, vol. 5754, pp. 1508-1518.
Nakamura et al., "Contact Hole Formation by Multiple Exposure Technique in Ultra-low k1 Lithography", *Proceedings of SPIE*, 2004, vol. 5377, pp. 255-263.
Mar. 17, 2014 Office Action issued in U.S. Appl. No. 13/524,669.
Jul. 9, 2014 Office Action issued in U.S. Appl. No. 13/524,669.
Oct. 21, 2014 Office Action issued in U.S. Appl. No. 13/854,622.
Feb. 10, 2014 Office Action issued in U.S. Appl. No. 13/430,319.
Jul. 17, 2013 Office Action issued in U.S. Appl. No. 13/430,319.
Sep. 4, 2014 Office Action issued in U.S. Appl. No. 13/747,125.
U.S. Appl. No. 13/747,125 in the name of Ogihara et al., filed Jan. 22, 2013.
U.S. Appl. No. 14/107,500 in the name of Ogihara et al., filed Dec. 16, 2013.
U.S. Appl. No. 13/854,622 in the name of Ogihara et al., filed Apr. 1, 2013.
U.S. Appl. No. 13/430,319 in the name of Ogihara et al., filed Mar. 26, 2012.
Feb. 25, 2015 Office Action issued in U.S. Appl. No. 14/107,500.
Dec. 24, 2014 Office Action issued in Japanese Application No. 2012-029230.
Mar. 27, 2015 Office Action issued in European Application No. 13000599.4.

\* cited by examiner

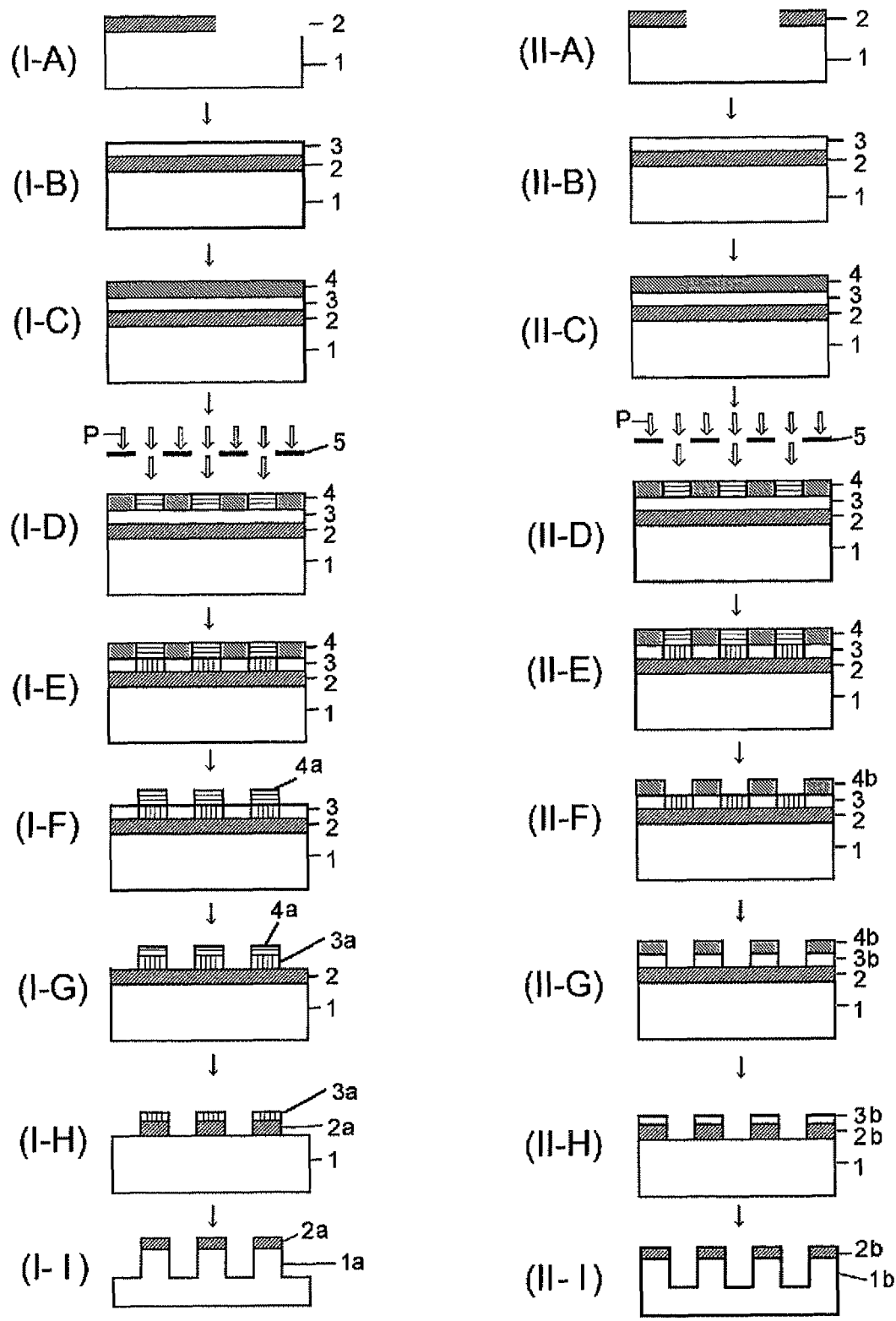

SILICON-CONTAINING SURFACE MODIFIER, RESIST UNDERLAYER FILM COMPOSITION CONTAINING THIS, AND PATTERNING PROCESS

BACKGROUND OF THE INVENTION

1. Field of the Invention

The present invention relates to a silicon-containing surface modifier, a resist underlayer film composition containing this, and a patterning process.

2. Description of the Related Art

In 1980s, photo-exposure using a g-beam (436 nm) or an i-beam (365 nm) of a mercury lamp as a light source had been widely used in the resist patterning. As a means for further miniaturization, shifting to a shorter wavelength of the exposure light was assumed to be effective, so that, in mass production process after the DRAM (Dynamic Random Access Memory) with 64 megabits (processing dimension of 0.25 μm or less) in 1990s, a KrF excimer laser (248 nm), a shorter wavelength than the i-beam (365 nm), had been used in place of the i-beam as an exposure light source. However, in production of DRAMs with integration degree of 256 M and 1 G or higher which require further miniaturized process technologies (processing dimension of 0.2 μm or less), a light source with further short wavelength is required, and thus, a photolithography using an ArF excimer laser (193 nm) has been investigated seriously since about a decade ago. At first, the ArF lithography was planned to be applied to manufacturing of a device starting from a 180-nm node device, but the life of the KrF excimer lithography was prolonged to mass production of the 130-nm node device; and thus, a full-fledged application of the ArF lithography started from the 90-nm node. Further, mass production of the 65-nm node device is now underway by combining thereof with a lens having an increased NA till 0.9. Further shortening of wavelength of the exposure light is progressing in the next 45-nm node device; and for that, the $F_2$-lithography with 157 nm wavelength became a candidate. However, there are many problems with the $F_2$ lithography: cost-up of a scanner due to use of a large quantities of expensive $CaF_2$ single crystals for a projector lens; extremely poor sustainability of a soft pellicle, which leads to change of an optical system due to introduction of a hard pellicle; decrease in etching resistance of a resist film, and so forth. Because of these problems, development of the $F_2$ lithography was suspended, and the ArF immersion lithography was introduced.

In the ArF immersion lithography, water having refractive index of 1.44 is introduced between a projection lens and a wafer by a partial fill method thereby enabling high speed scanning; and thus, mass production of the 45-nm node device is now underway by using a lens with a NA class of 1.3.

For the 32-nm node lithography technology, a lithography with a vacuum ultraviolet beam (EUV) of 13.5 nm wavelength is considered to be a candidate. Problems to be solved in the EUV lithography are a higher output power of the laser, a higher sensitivity of the resist film, a higher resolution power, a lower line edge roughness (LER), a non-defect MoSi laminate mask, a lower aberration of the reflective mirror, and so forth; and thus, there are mounting problems to be solved.

Development of the immersion lithography with a high refractive index, another candidate for the 32-nm node, was suspended, because transmittance of LUAG, a candidate for a high refractive index lens, is low, and refractive index of the liquid could not reach an aimed value of 1.8.

As mentioned above, in the photo-exposure used as a general technology, resolution power based on the wavelength of a light source is approaching to its inherent limit. Therefore, in recent years, development by an organic solvent, with which a very fine hole pattern that could not be achieved by a patterning process with a positive tone by a conventional alkaline development is formed by a patterning process with a negative tone by the organic solvent development, is receiving an attention again. This is a patterning process with which a negative pattern is formed by the organic solvent development by using a positive resist composition having a high resolution power. Further, an investigation to obtain a doubled resolution power by combining two developments of the alkaline development and the organic solvent development is now underway.

As to the ArF resist composition used for the negative tone development by an organic solvent as mentioned above, a conventional positive ArF resist composition can be used; and a patterning process thereof is shown, for example, in the Patent Document 1 to 3.

One method to transfer the negative tone pattern formed as mentioned above to a substrate is a multilayer resist method. In this method, a photoresist film, i.e., an intermediate film having a different etching selectivity from a resist upper layer film, for example, a silicon-containing resist underlayer film, is intervened between the resist upper layer film and a substrate to be processed whereby obtaining a pattern on the resist upper layer film; and then, after the pattern is transferred to the resist underlayer film by dry etching by using the upper layer resist pattern as a dry etching mask, the pattern is further transferred to the substrate to be processed by dry etching by using the resist underlayer film as a dry etching mask.

Illustrative example of the silicon-containing resist underlayer film used in the multilayer resist method as mentioned above includes a silicon-containing inorganic film formed by CVD, such as a $SiO_2$ film (for example, Patent Document 4) and a SiON film (for example, Patent Document 5), and those formed by a spin coating method, such as a SOG film (spin-on-glass film) (for example, Patent Document 6) and a crosslinking silsesquioxane film (for example, Patent Document 7).

PRIOR ART DOCUMENTS

Patent Documents

Patent Document 1: Japanese Patent Laid-Open Publication No. 2008-281974

Patent Document 2: Japanese Patent Laid-Open Publication No. 2008-281980

Patent Document 3: Japanese Patent Laid-Open Publication No 2009-53657

Patent Document 4: Japanese Patent Laid-Open Publication No. 7-183194

Patent Document 5: Japanese Patent Laid-Open Publication No. 7-181688

Patent Document 6: Japanese Patent Laid-Open Publication No. 2007-302873

Patent Document 7: Japanese Patent Laid-Open Publication No. 2005-520354

SUMMARY OF THE INVENTION

However, on contrary to the positive development (alkaline development) in which a resist pattern is formed of a hydrophobic compound not soluble in an alkaline developer, in the negative development (organic solvent development), a resist pattern is formed of a hydrophilic organic compound having an acidic carboxyl group and the like in high concentration by a deprotection reaction, so that the upper layer resist cannot express satisfactorily its performance by a conventional resist underlayer film for the alkaline development.

On the other hand, if the resist underlayer film used in the negative development is different from the resist underlayer film used in the positive development, piping equipment dedicated to respective developments are necessary; and therefore, it is economically disadvantageous.

The present invention was made in view of the situation mentioned above, and has an object to provide a resist underlayer film applicable not only to the resist pattern which is formed of a hydrophilic organic compound obtained by the negative development but also to the resist pattern which is formed of a hydrophobic compound and obtained by the conventional positive development.

To solve the problem shown above, the present invention provides a silicon-containing surface modifier, wherein the surface modifier contains one or more of a repeating unit shown by the following general formula (A) and a partial structure shown by the following general formula (C),

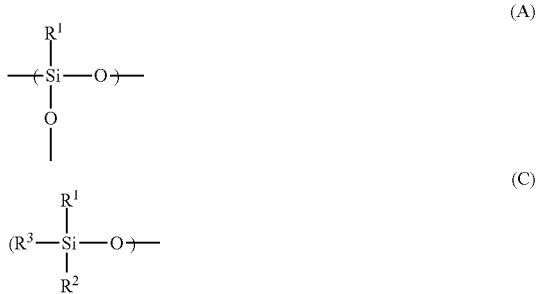

wherein $R^1$ represents an organic group having a hydroxyl group or a carboxylic acid group, the groups being substituted with an acid-labile group. Each of $R^2$ and $R^3$ independently represents a group identical to $R^1$, a hydrogen atom, or a monovalent organic group having 1 to 30 carbon atoms.

When a resist underlayer film formed by using a resist underlayer film composition which contains the silicon-containing surface modifier of the present invention as mentioned above is used, a resist pattern having good surface roughness with good adhesion to the resist underlayer film and without pattern fall may be formed in any of positive development (alkaline development) and negative development (organic solvent development).

The silicon-containing surface modifier may further contain a repeating unit shown by the following general formula (B),

wherein $R^1$ and $R^2$ represent the same meanings as before.

By containing the repeating unit shown by the general formula (B), design range of the silicon-containing surface modifier may become further broader so that it can be applied to patterning using various photoresists.

Furthermore, the acid-labile group in the foregoing $R^1$ is preferably an acetal group or a tertiary alkyl group.

If an acetal group or a tertiary alkyl group is used as the acid-labile group in $R^1$, especially adhesion to the upper layer resist pattern is improved also in a negative development process so that pattern fall can be prevented from occurring even in a narrow line pattern.

In addition, the present invention provides a silicon-containing resist underlayer film composition wherein the composition contains the silicon-containing surface modifier and a polysiloxane compound.

If the silicon-containing surface modifier of the present invention is added with the polysiloxane compound, the silicon-containing resist underlayer film composition not causing pattern fall can be provided.

As the component in the polysiloxane compound, it is preferable that content of the component derived from a four-functional hydrolysable monomer be 70 mole % or more in the polysiloxane compound.

If content of the component derived from a four-functional hydrolysable monomer as the component in the polysiloxane compound is 70 mole % or more in the polysiloxane compound, the silicon-containing surface modifier of the present invention can be readily localized in surface of the film during formation thereof so that the silicon-containing resist underlayer film not causing pattern fall in any of positive development and negative development.

In addition, the composition of the present invention may contain a solvent having a boiling point of 180° C. or higher.

If the high boiling point solvent having a boiling point of 180° C. or higher is contained in the composition, the resist underlayer film having good adhesion to the upper layer resist pattern may be formed.

Further, the present invention provides a patterning process, wherein, an organic underlayer film is formed on a body to be processed by using an application-type organic underlayer film composition, a silicon-containing resist underlayer film is formed on the organic underlayer film by using the above-mentioned silicon-containing resist underlayer film composition, a photoresist film is formed on the silicon-containing resist underlayer film by using a chemically amplifying type resist composition, after heat treatment the photoresist film is exposed to a high energy beam, a positive pattern is formed by dissolving an exposed area of the photoresist film by using an alkaline developer, the pattern is transferred to the silicon-containing resist underlayer film by dry etching by using the photoresist film formed with the pattern as a mask, the pattern is transferred by dry etching of the organic underlayer film by using the silicon-containing resist underlayer film transferred with the pattern as a mask, and then the pattern is transferred to the body to be processed by dry etching by using the organic underlayer film transferred with the pattern as a mask.

In addition, the present invention provides a patterning process, wherein, an organic hard mask mainly composed of carbon is formed on a body to be processed by a CVD method, a silicon-containing resist underlayer film is formed on the organic hard mask by using the above-mentioned silicon-containing resist underlayer film composition, a photoresist film is formed on the silicon-containing resist underlayer film by using a chemically amplifying type resist composition, after heat treatment the photoresist film is exposed to a high energy beam, a positive pattern is formed by dissolving an exposed area of the photoresist film by using an alkaline developer, the pattern is transferred to the silicon-containing resist underlayer film by dry etching by using the photoresist film formed with the pattern as a mask, the pattern is transferred by dry etching of the organic hard mask by using the silicon-containing resist underlayer film transferred with the pattern as a mask, and then the pattern is transferred to the body to be processed by dry etching by using the organic hard mask transferred with the pattern as a mask.

If a pattern is formed by positive development by using the silicon-containing resist underlayer film formed by the silicon-containing resist underlayer film composition of the present invention, a pattern formed in the upper layer resist can be formed on the substrate without causing transfer difference in size by optimizing a combination of the CVD film and the coat film as mentioned above.

In addition, the present invention provides a patterning process, wherein, an organic underlayer film is formed on a body to be processed by using an application-type organic underlayer film composition, a silicon-containing resist underlayer film is formed on the organic underlayer film by using the above-mentioned silicon-containing resist underlayer film composition, a photoresist film is formed on the silicon-containing resist underlayer film by using a chemically amplifying type resist composition, after heat treatment the photoresist film is exposed to a high energy beam, a negative pattern is formed by dissolving an unexposed area of the photoresist film by using an organic solvent developer, the pattern is transferred to the silicon-containing resist underlayer film by dry etching by using the photoresist film formed with the pattern as a mask, the pattern is transferred by dry etching of the organic underlayer film by using the silicon-containing resist underlayer film transferred with the pattern as a mask, and then the pattern is transferred to the body to be processed by dry etching by using the organic underlayer film transferred with the pattern as a mask.

In addition, the present invention provides a patterning process, wherein, an organic hard mask mainly composed of carbon is formed on a body to be processed by a CVD method, a silicon-containing resist underlayer film is formed on the organic hard mask by using the above-mentioned silicon-containing resist underlayer film composition, a photoresist film is formed on the silicon-containing resist underlayer film by using a chemically amplifying type resist composition, after heat treatment the photoresist film is exposed to a high energy beam, a negative pattern is formed by dissolving an unexposed area of the photoresist film by using an organic solvent developer, the pattern is transferred to the silicon-containing resist underlayer film by dry etching by using the photoresist film formed with the pattern as a mask, the pattern is transferred by dry etching of the organic hard mask by using the silicon-containing resist underlayer film transferred with the pattern as a mask, and then the pattern is transferred to the body to be processed by dry etching by using the organic hard mask transferred with the pattern as a mask.

If a negatively developed pattern is formed by using the silicon-containing resist underlayer film formed by the silicon-containing resist underlayer film composition of the present invention, a pattern formed in the upper layer resist can be formed on the substrate without causing transfer difference in size by optimizing a combination of the CVD film and the coat film as mentioned above.

In addition, in the negative and the positive patterning process, as the body to be processed, it is preferable that a substrate for a semiconductor device or a substrate for a semiconductor device coated with any of a metal film, a metal alloy film, a metal carbide film, a metal oxide film, a metal nitride film, a metal oxide carbide film, and a metal oxide nitride film be used.

In the patterning processes mentioned above, it is preferable that the metal to constitute the body to be processed be any of silicon, gallium, titanium, tungsten, hafnium, zirconium, chromium, germanium, copper, aluminum, and iron, or a metal alloy of them.

By using the patterning process of the present invention, a pattern can be formed by processing the body to be processed as mentioned above.

As explained above, when the resist underlayer film formed by using the resist underlayer film composition containing the silicon-containing surface modifier of the present invention is used, a resist pattern having good adhesion to the resist underlayer film with good surface roughness and without pattern fall may be formed in any of the positive development (alkaline development) and the negative development (organic solvent development). In addition, because this resist underlayer film can have high etching selectivity to an organic material, the formed photoresist pattern can be transferred to the silicon-containing resist underlayer film and then sequentially to the organic underlayer film or to the CVD organic hard mask by a dry etching process. Especially, in recent years, as a process for manufacturing of a semiconductor device advances toward miniaturization, in order to avoid pattern fall after development, film thickness of the photoresist film tends to become thinner so that pattern transfer to the resist underlayer film becomes more difficult. However, if the silicon-containing resist underlayer film composition of the present invention is used, deformation of the photoresist pattern during dry etching can be suppressed even if a thin photoresist is used as an etching mask, so that this pattern can be transferred to the substrate with high precision.

In addition, in practical manufacturing process of a semiconductor device, all the patterning processes cannot be changed from the positive development to the negative development, but only small part of an ultrafine process is changed; and thus, it may be assumed that the existing positive development process remains unchanged. In this case, if equipment solely dedicated to the negative resist underlayer film and to the positive underlayer film are used, the equipment and quality control of the composition may become cumbersome. Accordingly, if the resist underlayer film composition is usable in both the positive and the negative processes as the case of the present invention, rational management may be possible in both equipment and quality control.

BRIEF DESCRIPTION OF THE DRAWINGS

FIG. 1 is a flow chart showing the patterning process of the present invention.

DESCRIPTION OF THE PREFERRED EMBODIMENTS

Hereinafter, the present invention will be explained in more detail.

In a conventional positive photoresist, film properties of the photoresist film before photo-exposure and film properties of the pattern formed by an alkaline development after photo-exposure (hereinafter this pattern is called "positive pattern") have been the same. And thus, to enhance adhesion of the positive pattern with the resist underlayer film, enhancement of adhesion of the positive pattern to the resist underlayer film and lowering of the roughness thereof could be effectively achieved by approximating contact angle of the photoresist to pure water with contact angle of the resist underlayer film to pure water (hereinafter "contact angle to pure water" is called "contact angle").

However, in the pattern obtained by a negative development (hereinafter, this pattern is called "negative pattern"), when comparison is made on film properties between the photoresist film before photo-exposure and the negative pattern after photo-exposure, in the negative pattern, an acid-labile group is eliminated by an acid generated by the photo-exposure thereby increasing the amount of a hydrophilic group such as a carboxyl group and a phenolic hydroxyl group; and as a result, the contact angle is shifted toward a more hydrophilic side, i.e., a lower side, than that of the photoresist film before photo-exposure. Because of this, in the patterning process in which both the negative development and the positive development are used as mentioned above, it was found, if a conventional resist underlayer film for positive development whose contact angle is made coincident with that of the photoresist film before the photo-exposure is used as it is, discrepancy from the contact angle of the negative pattern after photo-exposure is generated thereby causing pattern fall and an adverse effect in roughness in the negative pattern.

Accordingly, inventors of the present invention found that, by utilizing the aspect that the positive pattern is the unexposed area of the photoresist film and that the negative pattern is the exposed area of the photoresist film, if it was possible to have the contact angle approximated to the contact angle of the unexposed area of the photoresist film before photo-exposure and to have the contact angle approximated to the exposed area of the contact angle of the photo resist film after the photo-exposure, the resist underlayer film having an optimum surface condition in any of the processes could be obtained. Accordingly, the inventors carried out an extensive investigation on the silicon-containing resist underlayer film composition having the contact angle thereof decreased only in the exposed area; and as a result, it was found that, when a silicon-containing surface modifier containing an organic group which has a hydroxyl group or a carboxylic acid group, the groups being substituted with an acid-labile group, was blended with a resist underlayer film composition in an appropriate mixing ratio, a silicon-containing resist underlayer film composition having the contact angle thereof decreased only in the exposed area could be obtained, thereby accomplished the present invention.

That is, the silicon-containing surface modifier of the present invention is characterized by that the surface modifier contains one or more of a repeating unit shown by the following general formula (A) (hereinafter, sometimes referred to as "repeating unit (A)") and a partial structure shown by the following general formula (C) (hereinafter, sometimes referred to as "partial structure (C)"),

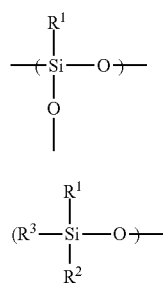

wherein $R^1$ represents an organic group having a hydroxyl group or a carboxylic acid group, the groups being substituted with an acid-labile group (preferably a cyclic or a noncyclic acetal group or a tertiary alkyl group). Each of $R^2$ and $R^3$ independently represents a group identical to $R^1$, a hydrogen atom, or a monovalent organic group having 1 to 30 carbon atoms.

Meanwhile, the organic group in the present invention means a organic group which contains a carbon atom; and it may further contain a hydrogen tom, and in addition, a nitrogen atom, an oxygen atom, a sulfur atom, a silicon atom, a halogen atom, and so forth.

The silicon-containing surface modifier of the present invention may further contain a repeating unit shown by the following general formula (B) (hereinafter, sometimes referred to as "repeating unit (B)"),

wherein and $R^2$ represent the same meanings as before.

Illustrative example of the organic group shown by $R^1$ and having a hydroxyl group or a carboxylic acid group, the groups being substituted with an acid-labile group, in the repeating units (A) and (B) and the partial structure (C), which constitute the silicon-containing surface modifier of the present invention, includes the structures shown by the following formulae. Meanwhile, in the following formulae, (Si) is described to show the bonding site to Si.

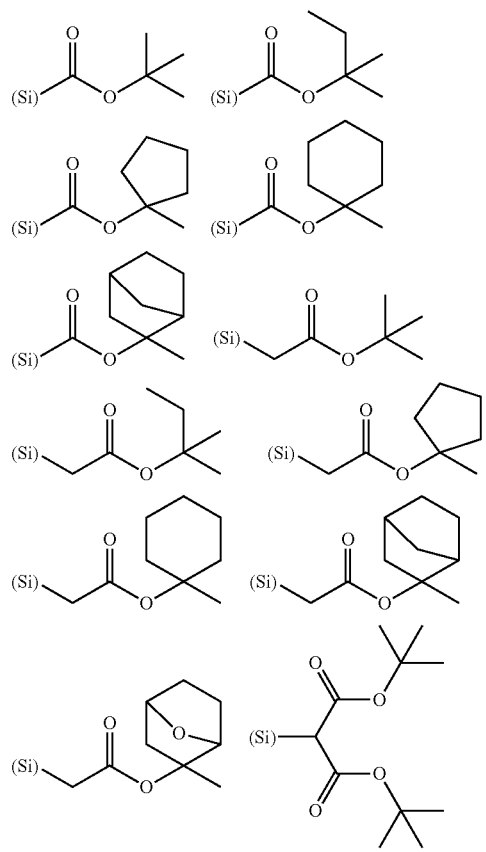

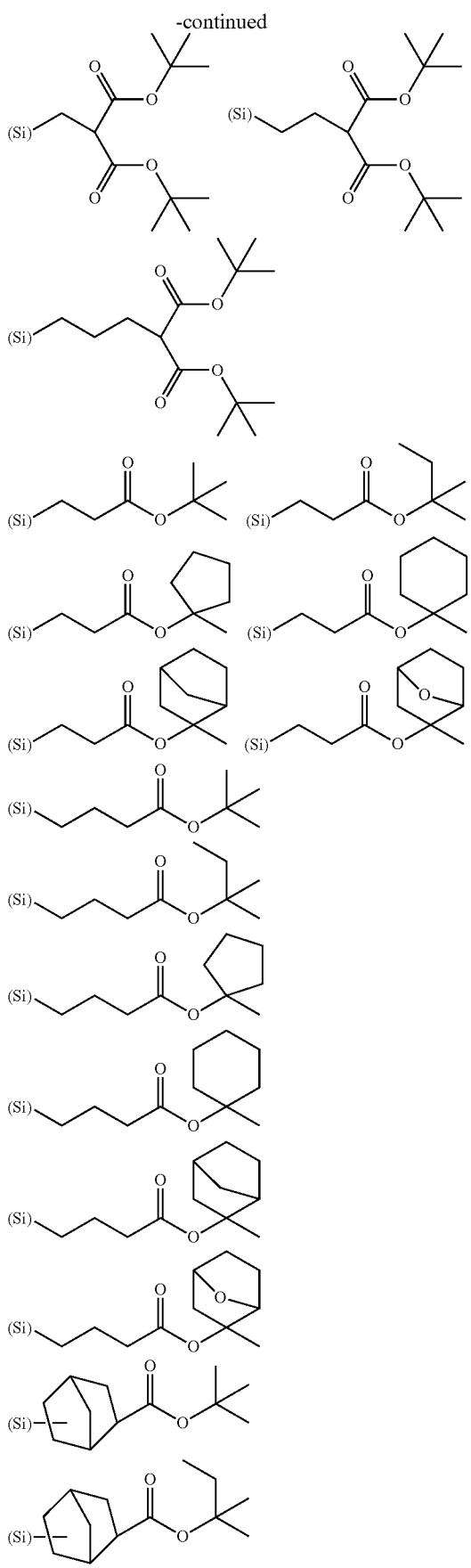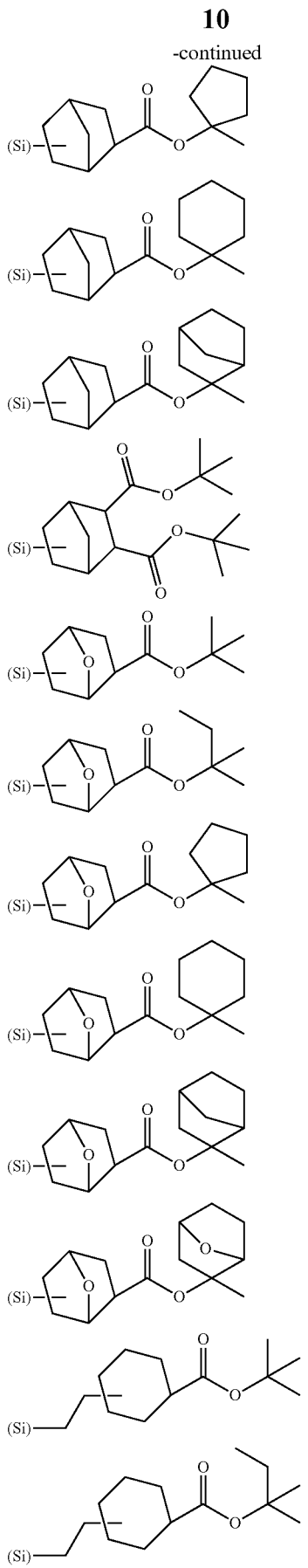

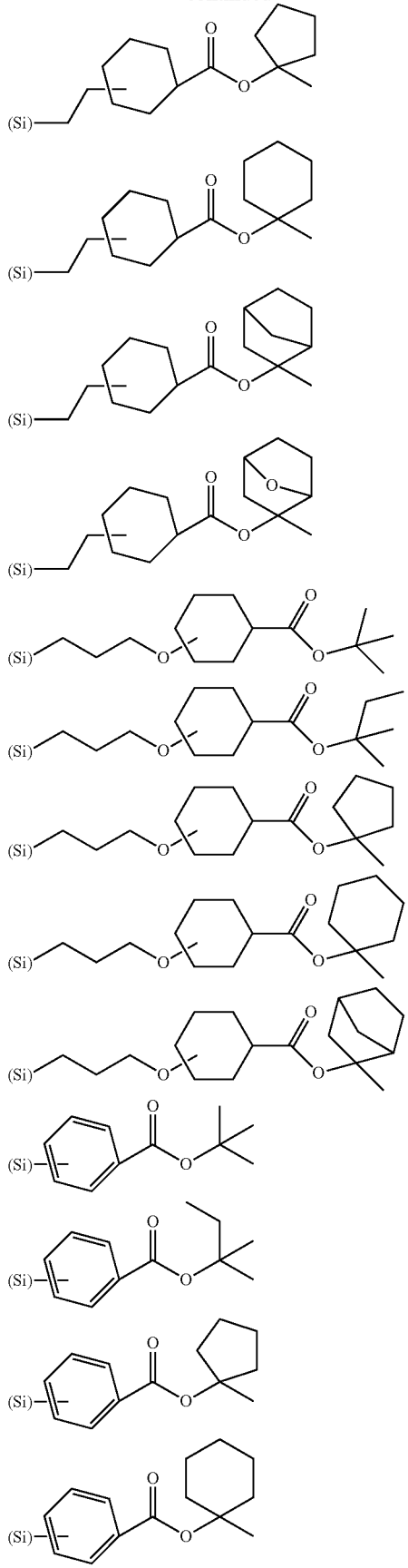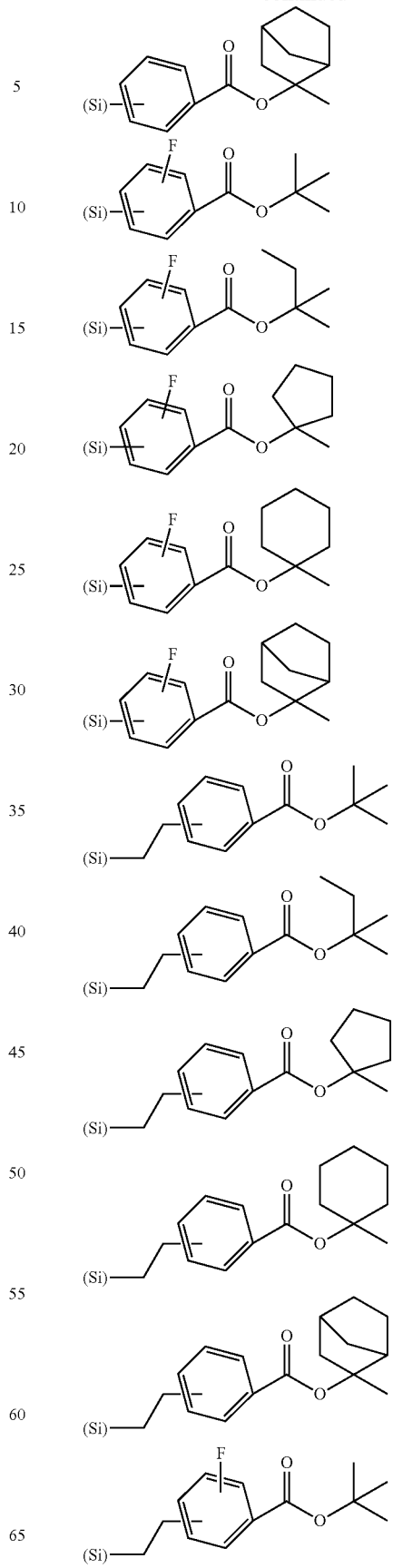

-continued
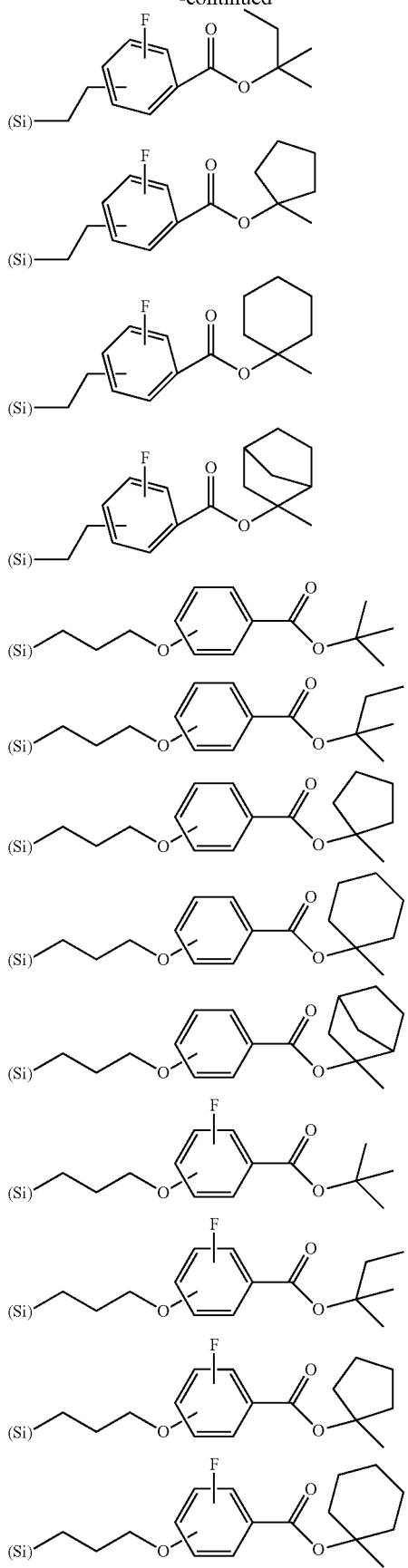
-continued
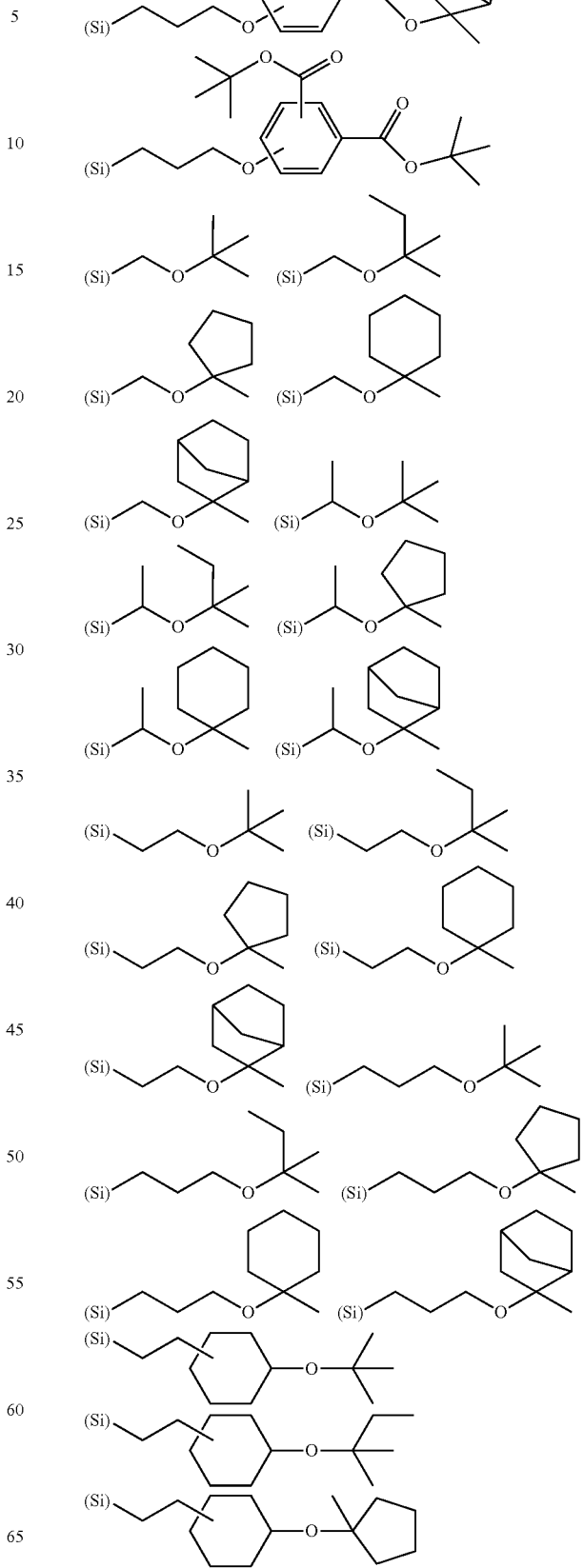

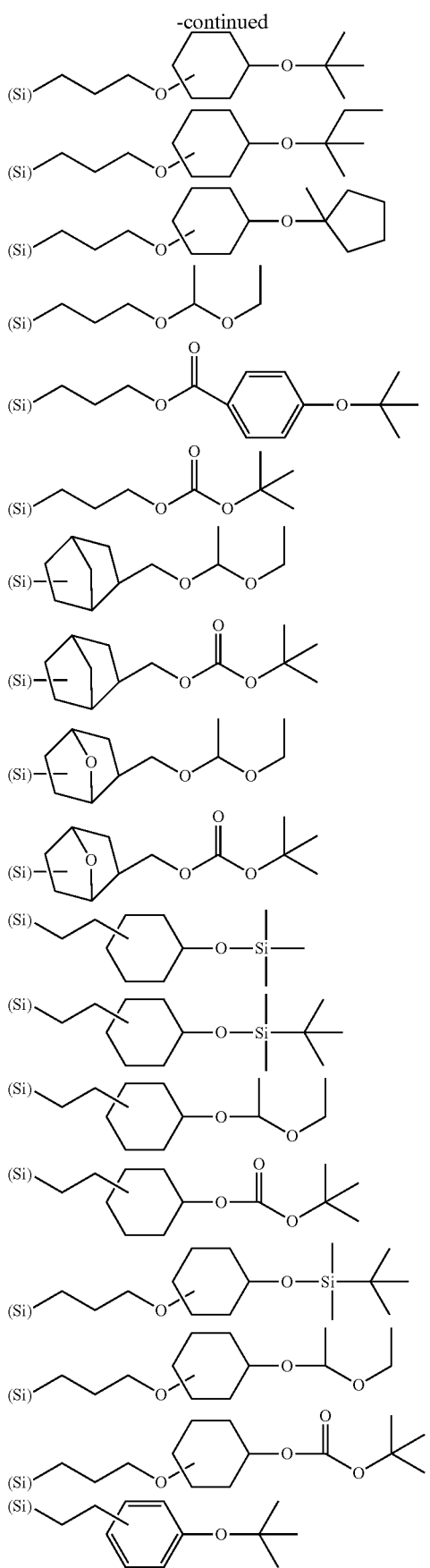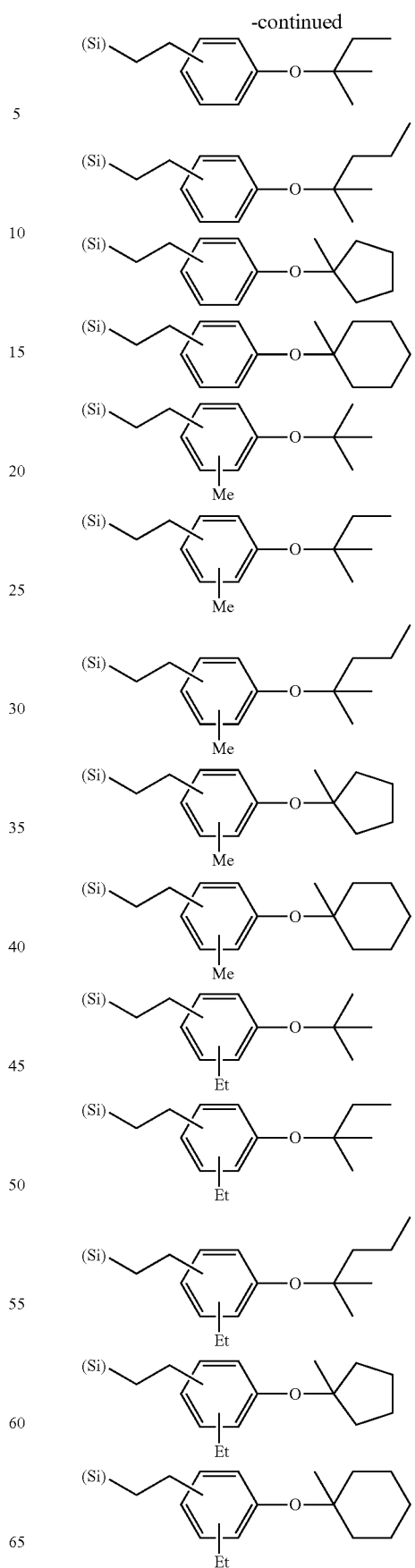

-continued
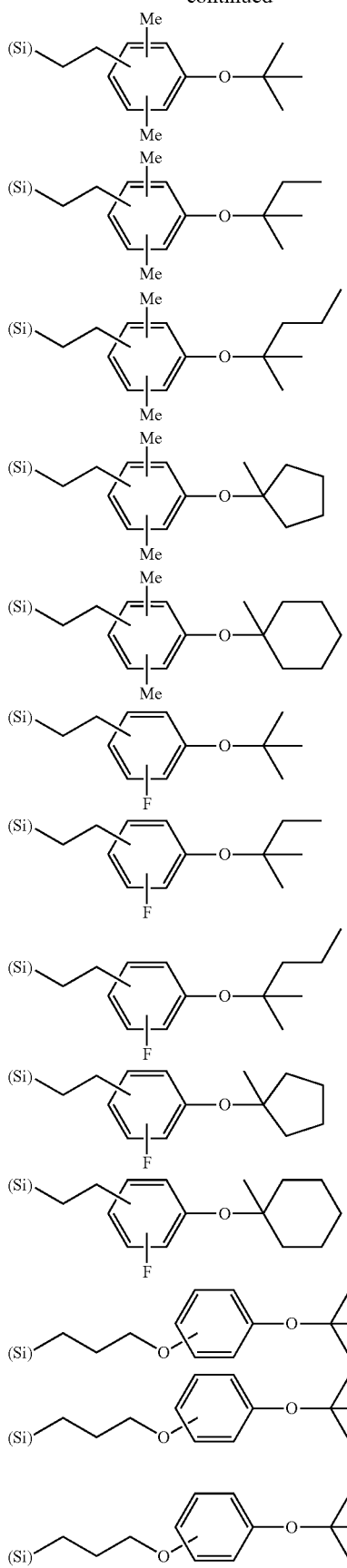
-continued
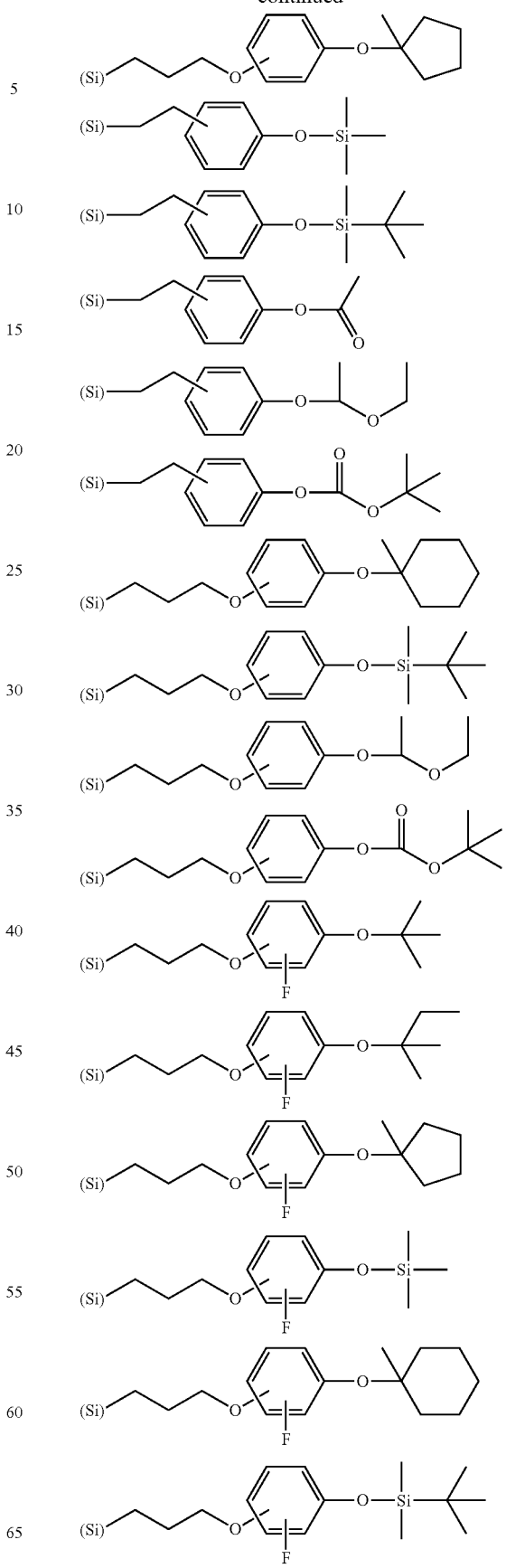

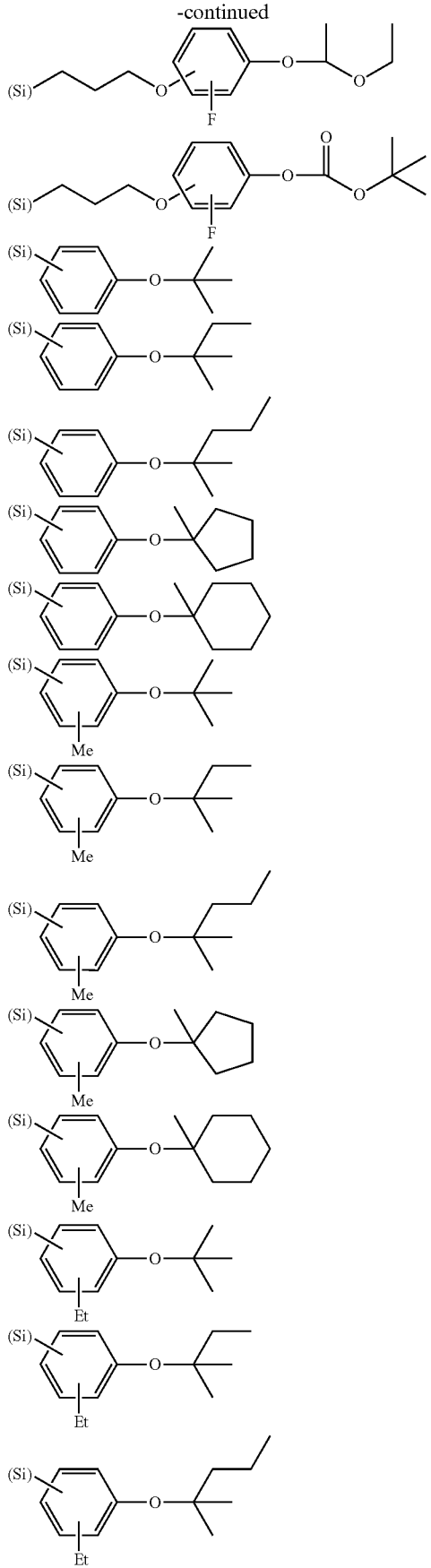
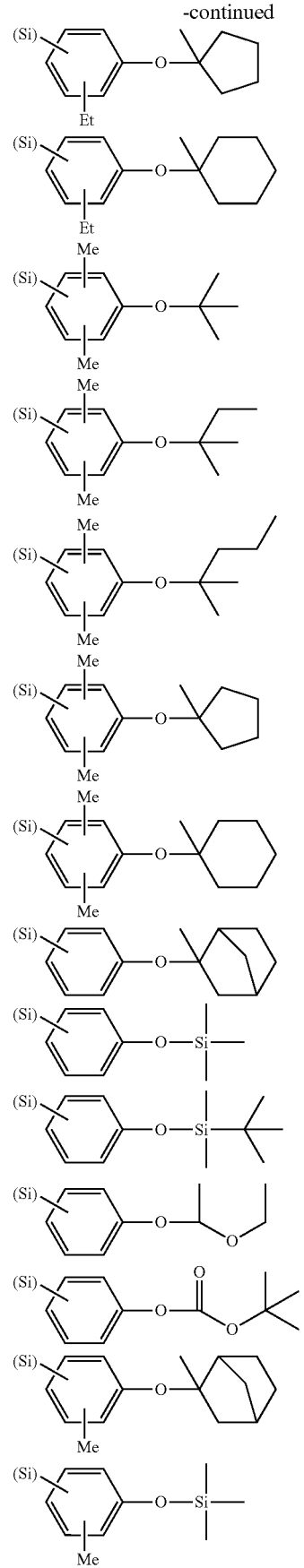

-continued
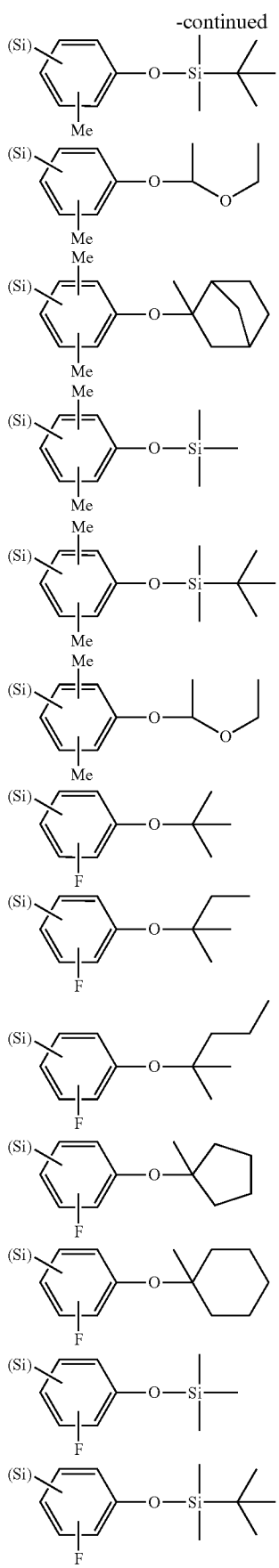
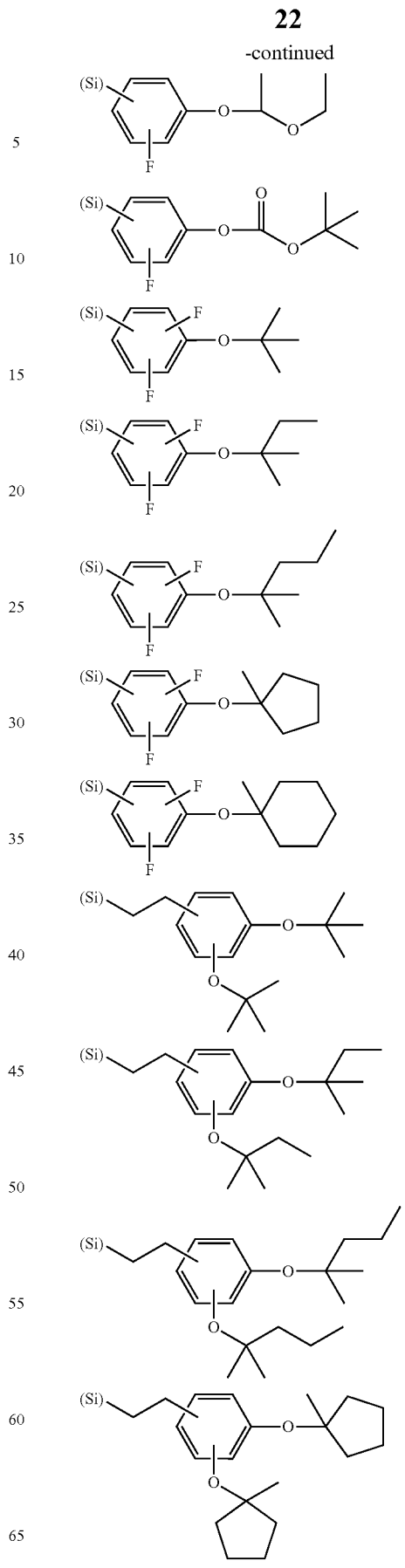

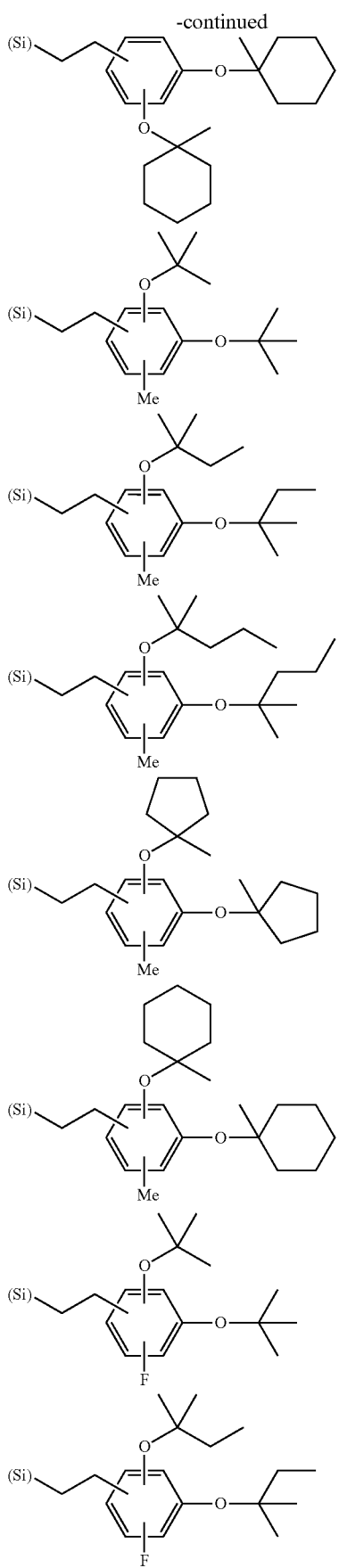
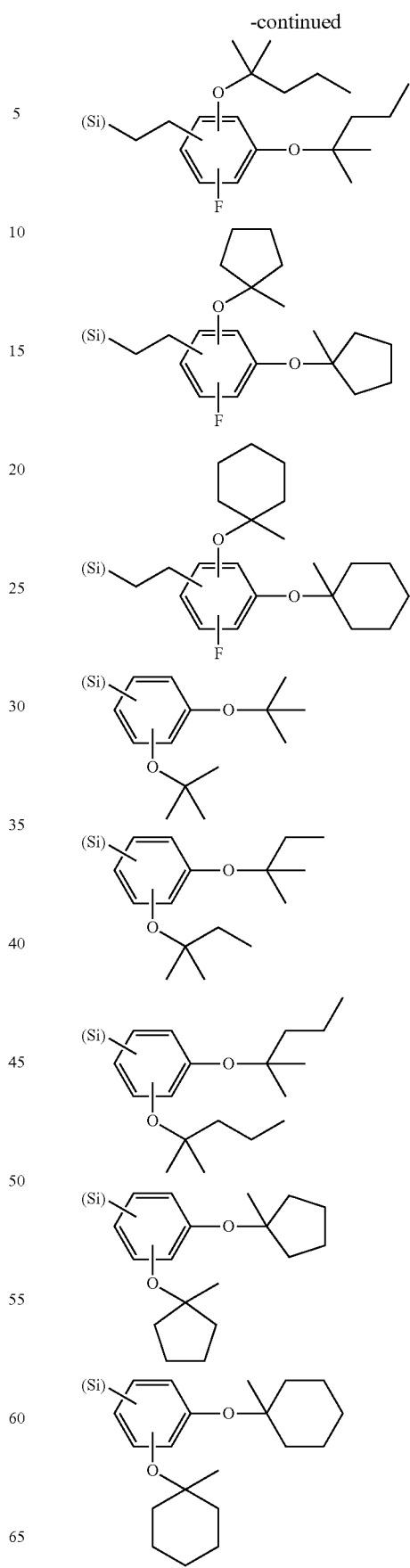

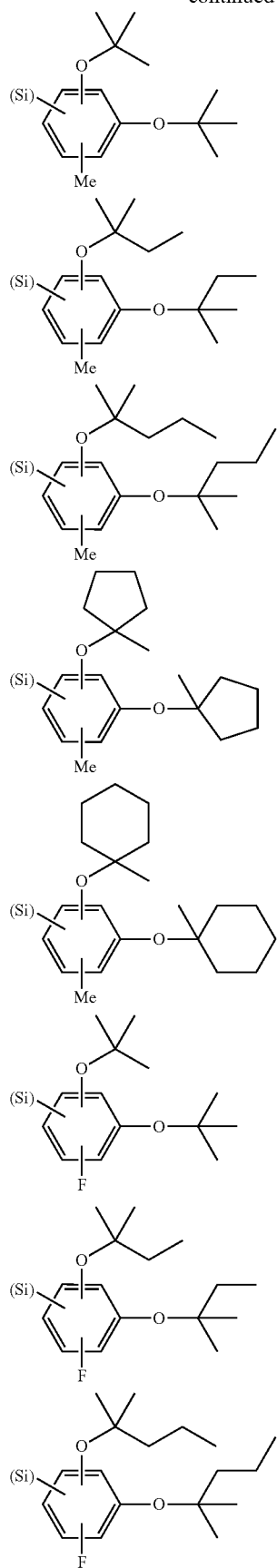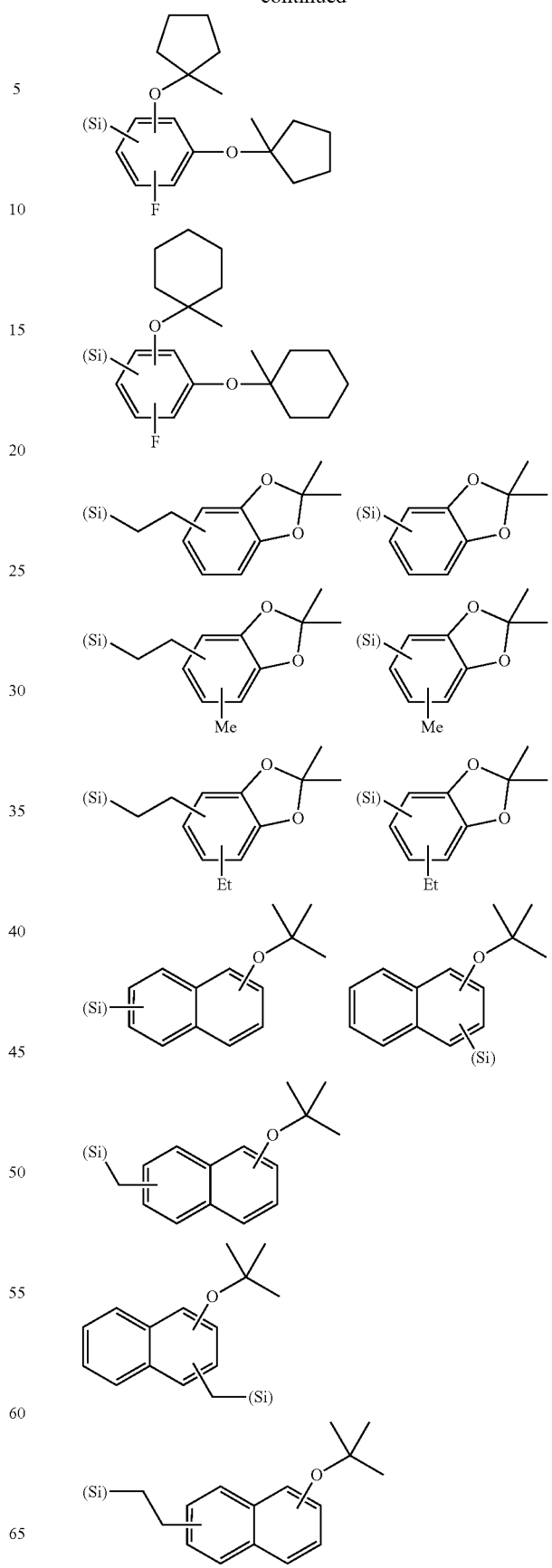

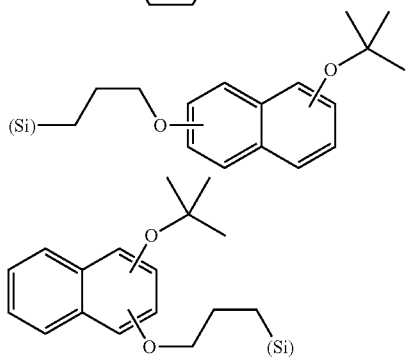

As to the hydrolysable monomer used as a raw material to form the surface modifier of the present invention, a monomer having the foregoing structures on a silicon atom while containing, as the hydrolysable group, one, two, or three of chlorine, bromine, iodine, an acetoxy group, a methoxy group, an ethoxy group, a propoxy group, a butoxy group, or the like, and further a hydrogen atom or a monovalent organic group having 1 to 30 carbon atoms as $R^2$ and $R^3$ may be used.

In addition, other hydrolysable monomers shown below may be contained therein; and thus, the silicon-containing surface modifier of the present invention may be produced by hydrolytic condensation of a mixture like this.

Illustrative example of the other hydrolysable monomers includes tetramethoxy silane, tetraethoxy silane, tetrapropoxy silane, tetraisopropoxy silane, trimethoxy silane, triethoxy silane, tripropoxy silane, triisopropoxy silane, methyl trimethoxy silane, methyl triethoxy silane, methyl tripropoxy silane, methyl triisopropoxy silane, ethyl trimethoxy silane, ethyl triethoxy silane, ethyl tripropoxy silane, ethyl triisopropoxy silane, vinyl trimethoxy silane, vinyl triethoxy silane, vinyl tripropoxy silane, vinyl triisopropoxy silane, propyl trimethoxy silane, propyl triethoxy silane, propyl tripropoxy silane, propyl triisopropoxy silane, isopropyl trimethoxy silane, isopropyl triethoxy silane, isopropyl tripropoxy silane, isopropyl triisopropoxy silane, butyl trimethoxy silane, butyl triethoxy silane, butyl tripropoxy silane, butyl triisopropoxy silane, sec-butyl trimethoxy silane, sec-butyl triethoxy silane, sec-butyl tripropoxy silane, sec-butyl triisopropoxy silane, t-butyl trimethoxy silane, t-butyl triethoxy silane, t-butyl tripropoxy silane, t-butyl triisopropoxy silane, cyclopropyl trimethoxy silane, cyclopropyl triethoxy silane, cyclopropyl tripropoxy silane, cyclopropyl triisopropoxy silane, cyclobutyl trimethoxy silane, cyclobutyl triethoxy silane, cyclobutyl tripropoxy silane, cyclobutyl triisopropoxy silane, cyclopentyl trimethoxy silane, cyclopentyl triethoxy silane, cyclopentyl tripropoxy silane, cyclopentyl triisopropoxy silane, cyclohexyl trimethoxy silane, cyclohexyl triethoxy silane, cyclohexyl tripropoxy silane, cyclohexyl triisopropoxy silane, cyclohexenyl trimethoxy silane, cyclohexenyl triethoxy silane, cyclohexenyl tripropoxy silane, cyclohexenyl triisopropoxy silane, cyclohexenylethyl trimethoxy silane, cyclohexenylethyl triethoxy silane, cyclohexenylethyl tripropoxy silane, cyclohexenylethyl triisopropoxy silane, cyclooctyl trimethoxy silane, cyclooctayl triethoxy silane, cyclooctyl tripropoxy silane, cyclooctyl triisopropoxy silane, cyclopentadienylpropyl trimethoxy silane, cyclopentadienylpropyl triethoxy silane, cyclopentadienylpropyl tripropoxy silane, cyclopentadienylpropyl triisopropoxy silane, bicycloheptenyl trimethoxy silane, bicycloheptenyl triethoxy silane, bicycloheptenyl tripropoxy silane, bicycloheptenyl triisopropoxy silane, bicycloheptyl trimethoxy silane, bicycloheptyl triethoxy silane, bicycloheptyl tripropoxy silane, bicycloheptyl triisopropoxy silane, adamantly trimethoxy silane, adamantly triethoxy silane, adamantly tripropoxy silane, adamantly triisopropoxy silane, phenyl trimethoxy silane, phenyl triethoxy silane, phenyl tripropoxy silane, phenyl triisopropoxy silane, benzyl trimethoxy silane, benzyl triethoxy silane, benzyl tripropoxy silane, benzyl triisopropoxy silane, anisyl trimethoxy silane, anisyl triethoxy silane, anisyl tripropoxy silane, anysil triisopropoxy silane, tolyl trimethoxy silane, tolyl triethoxy silane, tolyl tripropoxy silane, tolyl triisopropoxy silane, phenetyl trimethoxy silane, phenetyl triethoxy silane, phenetyl tripropoxy silane, phenetyl triisopropoxy silane, naphthyl trimethoxy silane, naphthyl triethoxy silane, naphthyl tripropoxy silane, naphthyl triisopropoxy silane, dimethyl dimethoxy silane, dimethyl diethoxy silane, methyl ethyl dimethoxy silane, methyl ethyl diethoxy silane, dimethyl dipropoxy silane, dimethyl diisopropoxy silane, diethyl dimethoxy silane, diethyl diethoxy silane, diethyl dipropoxy silane, diethyl diisopropoxy silane, dipropyl dimethoxy silane, dipropyl diethoxy silane, dipropyl dipropoxy silane, dipropyl diisopropoxy silane, diisopropyl dimethoxy silane, diisopropyl diethoxy silane, diisopropyl dipropoxy silane, diisopropyl diisopropoxy silane, dibutyl dimethoxy silane, dibutyl diethoxy silane, dibutyl dipropoxy silane, dibutyl diisopropoxy silane, disec-butyl dimethoxy silane, disec-butyl diethoxy silane, disec-butyl dipropoxy silane, disec-butyl diisopropoxy silane, dit-butyl dimethoxy silane, dit-butyl diethoxy silane, dit-butyl dipropoxy silane, dit-butyl diisopropoxy silane, dicyclopropyl dimethoxy silane, dicyclopropyl diethoxy silane, dicyclopropyl dipropoxy silane, dicyclopropyl diisopropoxy silane, dicyclobutyl dimethoxy silane, dicyclobutyl diethoxy silane, dicyclobutyl dipropoxy silane, dicyclobutyl diisopropoxy silane, dicyclopentyl dimethoxy silane, dicyclopentyl diethoxy silane, dicyclopentyl dipropoxy silane, dicyclopentyl diisopropoxy silane, dicyclohexyl dimethoxy silane, dicyclohexyl diethoxy silane, dicyclohexyl dipropoxy silane, dicyclohexyl diisopropoxy silane, dicyclohexenyl dimethoxy silane, dicyclohexenyl diethoxy silane, dicyclohexenyl dipropoxy silane, dicyclohexenyl diisopropoxy silane, dicyclohexenylethyl dimethoxy silane, dicyclohexenylethyl diethoxy silane, dicyclohexenylethyl dipropoxy silane, dicyclohexenylethyl diisopropoxy silane, dicyclooctyl dimethoxy silane, dicyclooctyl diethoxy silane, dicyclooctyl dipropoxy silane, dicyclooctyl diisopropoxy silane, dicyclopentadienylpropyl dimethoxy silane, dicyclopentadienylpropyl diethoxy silane, dicyclopentadienylpropyl dipropoxy silane, dicyclopentadienylpropyl diisopropoxy silane, bis(bicycloheptenyl)dimethoxy silane, bis(bicycloheptenyl)diethoxy silane, bis(bicycloheptenyl)dipropoxy silane, bis(bicycloheptenyl)diisopropoxy silane, bis(bicycloheptyl)dimethoxy silane, bis(bicycloheptyl)diethoxy silane, bis(bicycloheptyl)dipropoxy silane, bis(bicycloheptyl)diisopropoxy silane, diadamantyl dimethoxy silane, diadamantyl diethoxy silane, diadamantyl dipropoxy silane, diadamantyl diisopropoxy silane, diphenyl dimethoxy silane, diphenyl diethoxy silane, methyl phenyl dimethoxy silane, methyl phenyl diethoxy silane, diphenyl dipropoxy silane, diphenyl diisopropoxy silane, trimethyl methoxy silane, trimethyl ethoxy silane, dimethyl ethyl methoxy silane, dimethyl ethyl ethoxy silane, dimethyl phenyl methoxy silane, dimethyl phenyl ethoxy silane, dimethyl benzyl methoxy silane, dimethyl benzyl ethoxy silane, dimethyl phenethyl methoxy silane, and dimethyl phenethyl ethoxy silane.

Preferable example of the other hydrolysable monomers mentioned above includes tetramethoxy silane, tetraethoxy silane, methyl trimethoxy silane, methyl triethoxy silane, ethyl trimethoxy silane, ethyl triethoxy silane, vinyl trimethoxy silane, vinyl triethoxy silane, propyl trimethoxy silane, propyl triethoxy silane, isopropyl trimethoxy silane, isopropyl triethoxy silane, butyl trimethoxy silane, butyl triethoxy silane, isobutyl trimethoxy silane, isobutyl triethoxy silane, allyl trimethoxy silane, allyl triethoxy silane, cyclopentyl trimethoxy silane, cyclopentyl triethoxy silane, cyclohexyl trimethoxy silane, cyclohexyl triethoxy silane, cyclohexenyl trimethoxy silane, cyclohexenyl triethoxy silane, phenyl trimethoxy silane, phenyl triethoxy silane, benzyl trimethoxy silane, benzyl triethoxy silane, tolyl trimethoxy silane, tolyl triethoxy silane, anisyl trimethoxy silane, anisyl triethoxy silane, phenetyl trimethoxy silane, phenetyl triethoxy silane, dimethyl dimethoxy silane, dimethyl diethoxy silane, diethyl dimethoxy silane, diethyl diethoxy silane, methyl ethyl dimethoxy silane, methyl ethyl diethoxy silane, dipropyl dimethoxy silane, dibutyl dimethoxy silane, methyl phenyl dimethoxy silane, methyl phenyl diethoxy silane, trimethyl methoxy silane, dimethyl ethyl methoxy silane, dimethyl phenyl methoxy silane, dimethyl benzyl methoxy silane, and dimethyl phenethyl methoxy silane.

Meanwhile, in the case that the foregoing $R^2$ and $R^3$ are an organic group having 1 to 30 carbon atoms, example of the organic group is an organic group having one or more of a carbon-oxygen single bond or a carbon-oxygen double bond. Specifically an organic group having one or more of a group selected from the group consisting of an epoxy group, an ester group, an alkoxy group, and a hydroxyl group may be mentioned. Illustrative example thereof includes the group shown by the following general formula (1).

$$(P-Q_1-(S_1)_{v1}-Q_2-)_u-(T)_{v2}-Q_3-(S_2)_{v3}-Q_4- \tag{1}$$

wherein P represents a hydrogen atom, a hydroxyl group, a epoxy ring

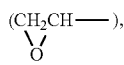

an alkoxy group having 1 to 4 carbon atoms, an alkylcarbonyloxy group having 1 to 6 carbon atoms, or an alkylcarbonyl group having 1 to 6 carbon atoms; each of $Q_1$, $Q_2$, $Q_3$, and $Q_4$ independently represents $-C_qH_{(2q-p)}P_p-$ wherein P represents the same meaning as before; p represents an integer of 0 to 3; q represents an integer of 0 to 10 (however, q=0 means a single bond)); u represents an integer of 0 to 3; each of $S_1$ and $S_2$ independently represents $-O-$, $-CO-$, $-OCO-$, $-COO-$, or $-OCOO-$. Each of v1, v2, and v3 independently represents 0 or 1. Concurrently with the above, T represents an alicyclic or an aromatic divalent group optionally containing a heteroatom, and illustrative example of the alicyclic or the aromatic T optionally containing a heteroatom such as an oxygen atom includes those shown below. In T, respective bonding sites to $Q_2$ and to $Q_3$ are not particularly restricted; and the sites are appropriately selected by considering reactivity due to a steric factor, availability of a commercially available reagent, and so on.

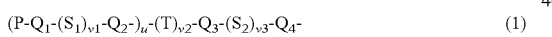

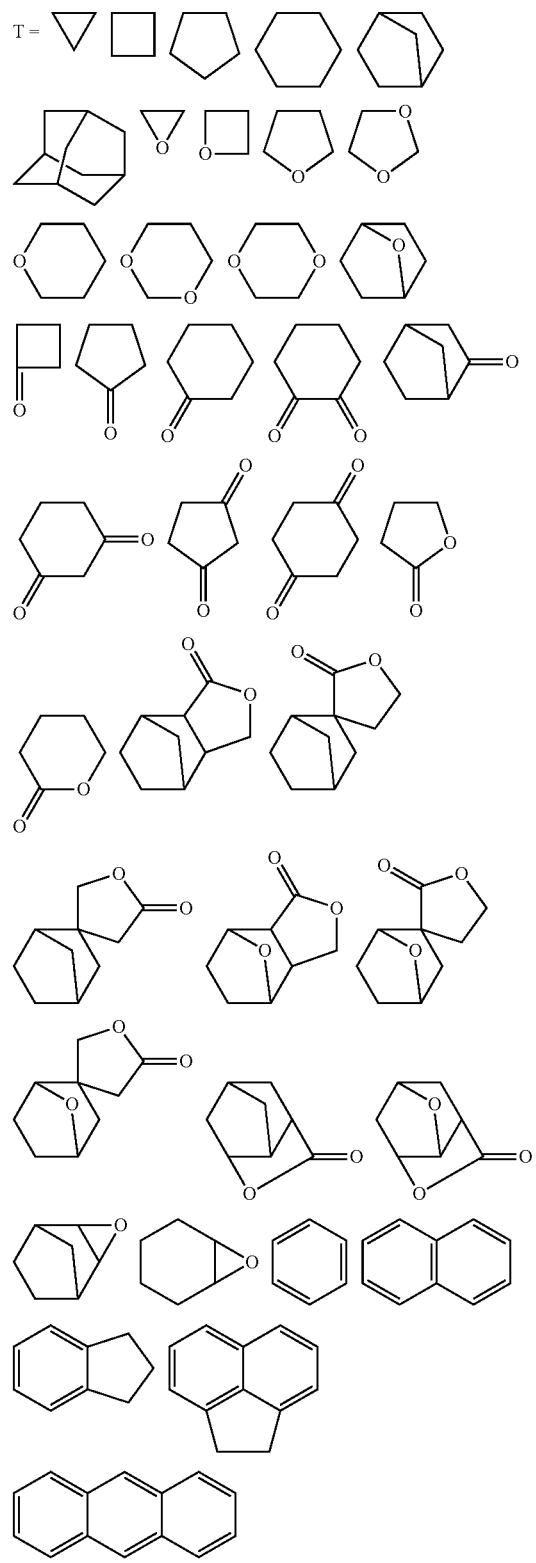

Preferable example of the organic group which is shown by the general formula (1) and has one or more of a carbon-oxygen single bond or a carbon-oxygen double bond includes those shown below. Meanwhile, in the following formulae, (Si) is described to show the bonding site to Si.

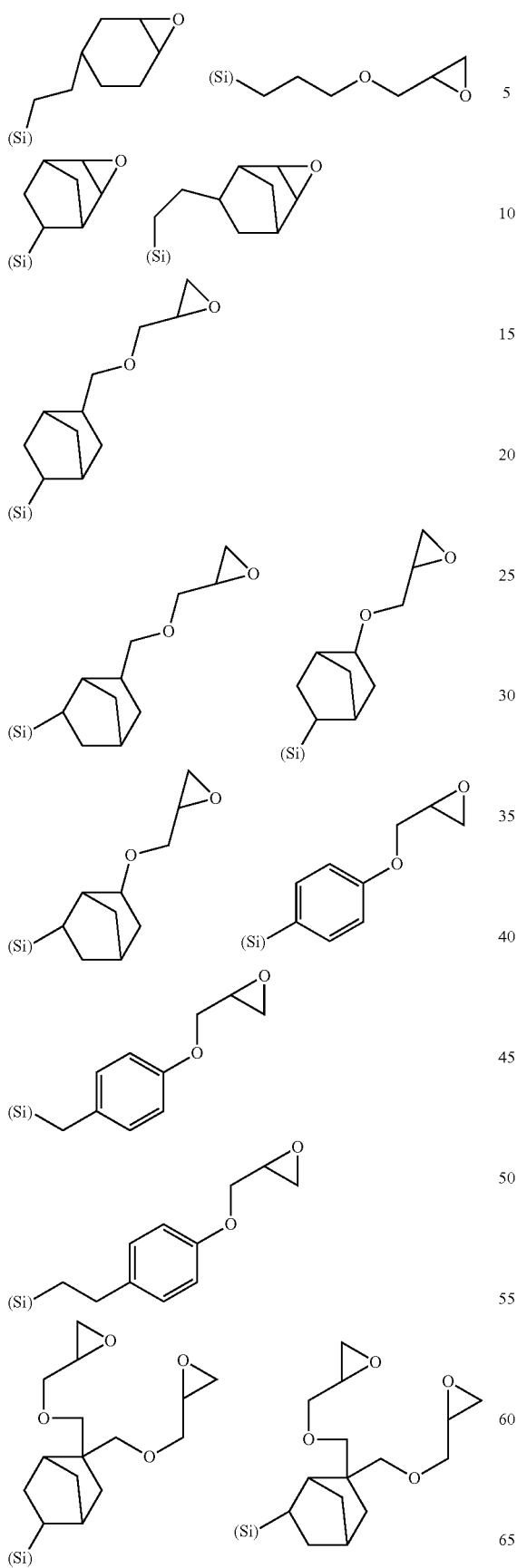

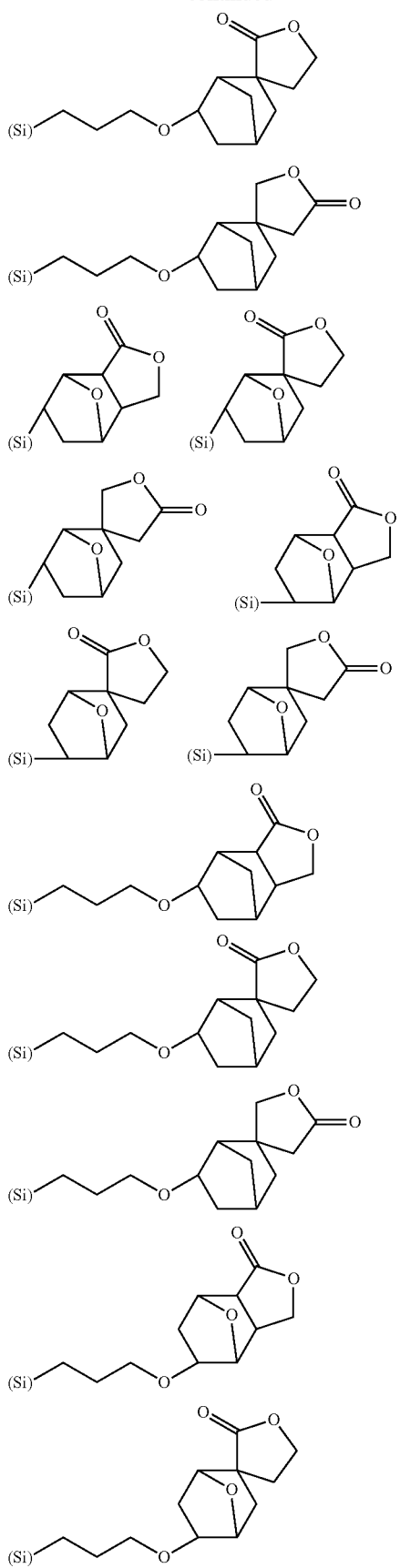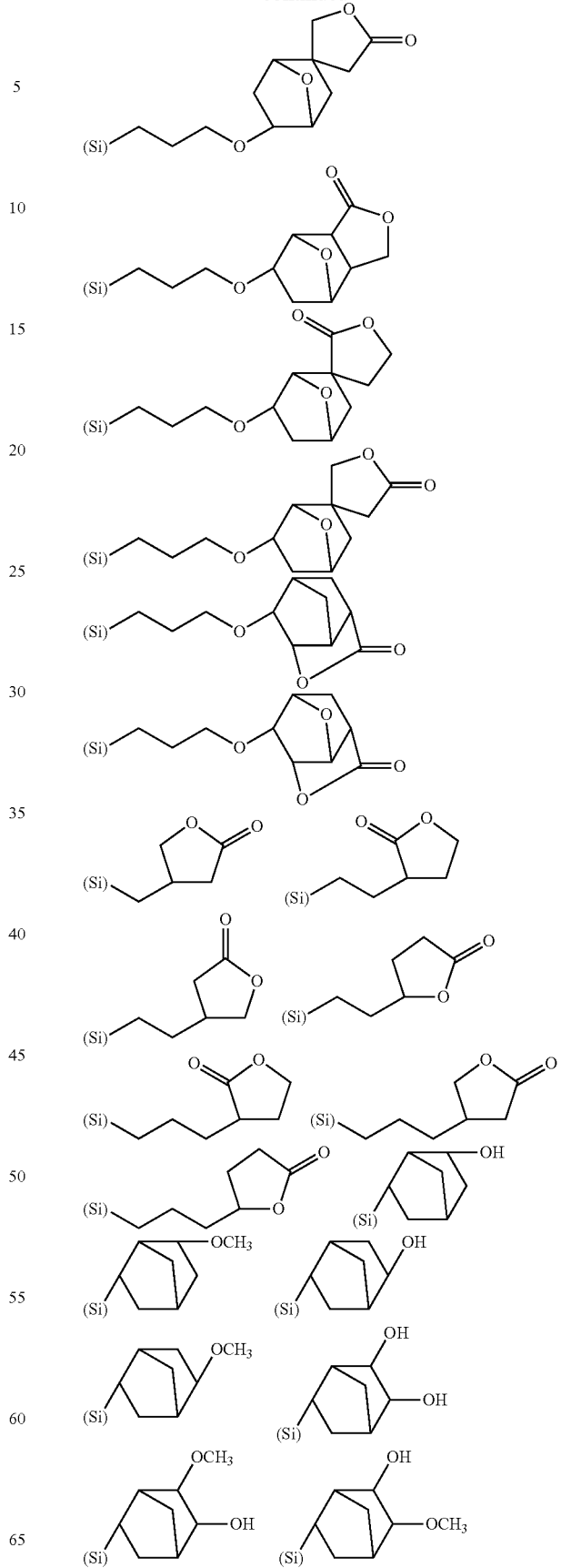

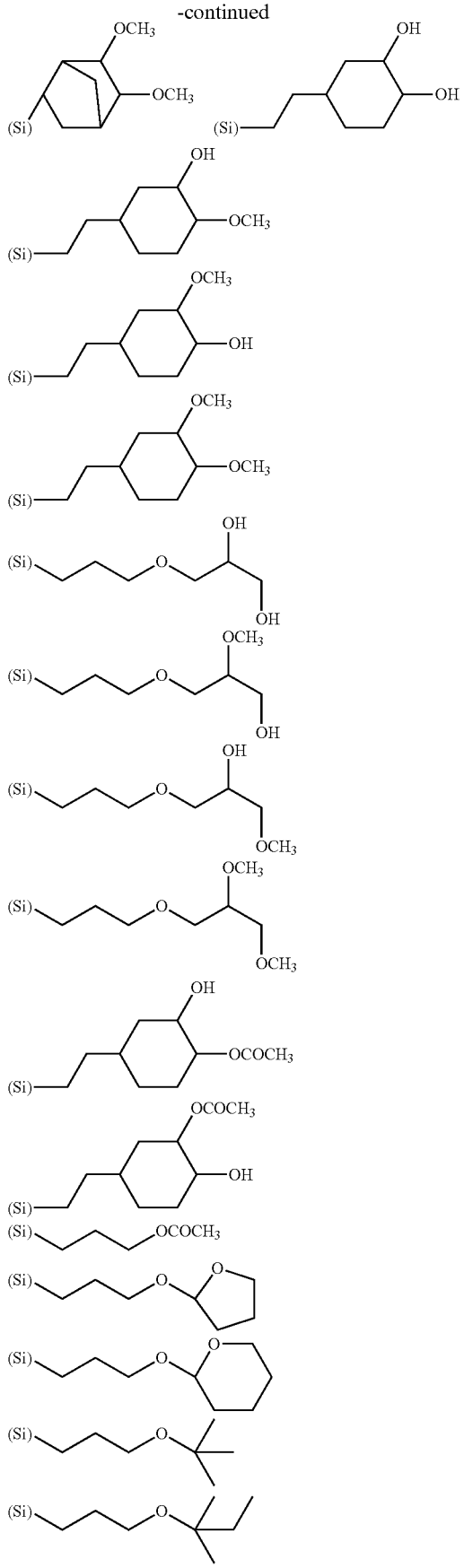
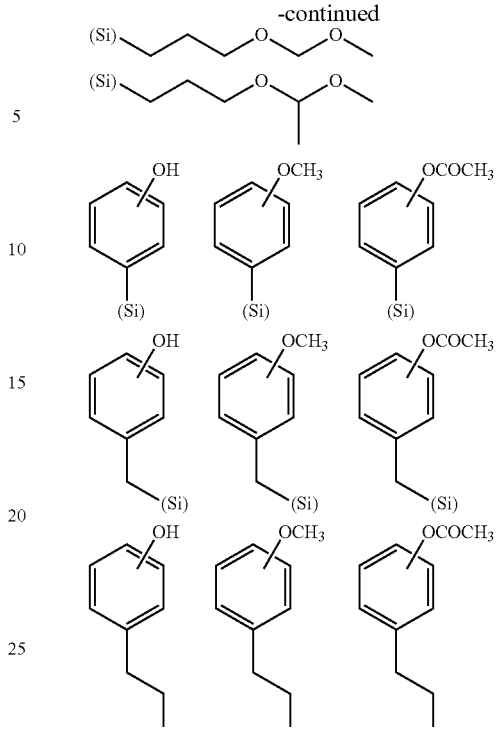
Alternatively, illustrative example of the organic group shown by $R^2$ and $R^3$ can include an organic group having a silicon-silicon bond. Groups shown below are the specific examples thereof.
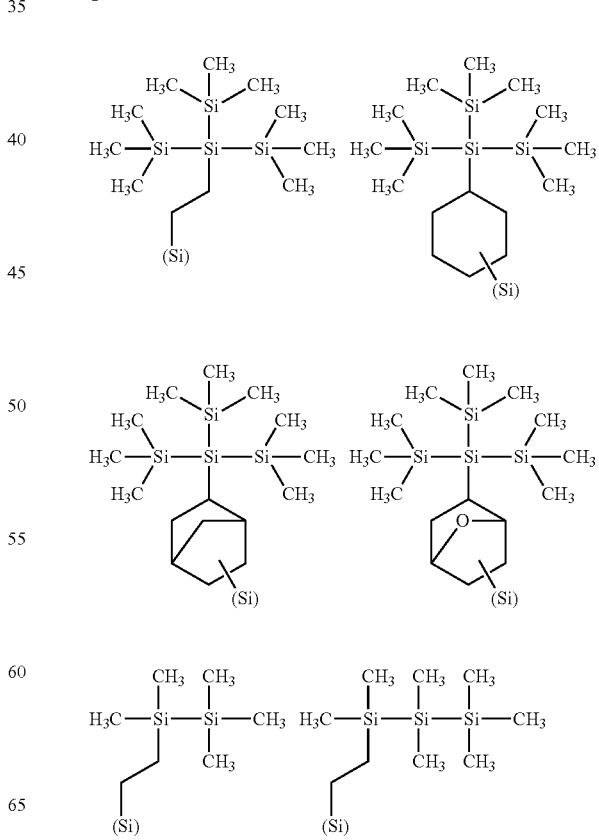

-continued

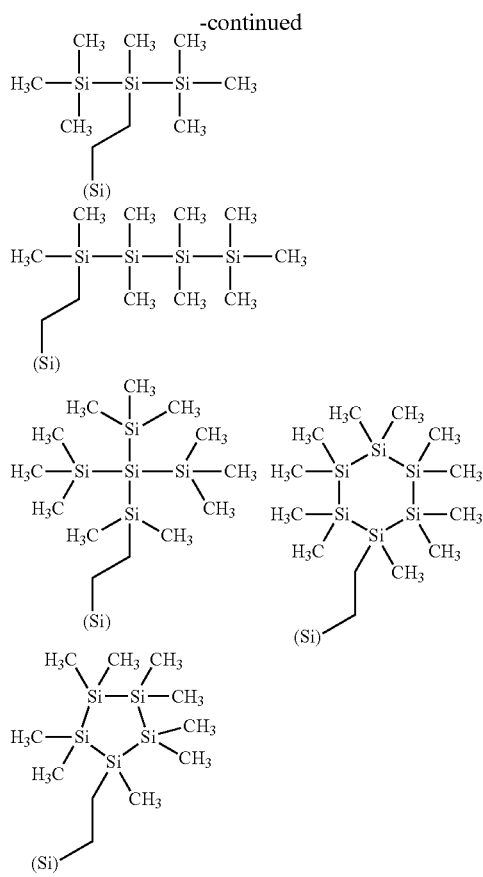

1. Synthesis Methods of the Silicon-Containing Surface Modifier 1-1. Synthesis Method 1: Acid Catalyst The silicon-containing surface modifier of the present invention may be produced, for example, by hydrolytic condensation of one or a mixture of two or more kinds of the hydrolysable monomers mentioned above in the presence of an acid catalyst.

Illustrative example of the acid catalyst used for this reaction includes an organic acid such as formic acid, acetic acid, oxalic acid, and maleic acid; and hydrofluoric acid, hydrochloric acid, hydrobromic acid, sulfuric acid, nitric acid, perchloric acid, phosphoric acid, methanesulfonic acid, benzenesulfonic acid, and toluenesulfonic acid. Use amount of the catalyst is $1\times10^{-6}$ to 10 moles, preferably $1\times10^{-5}$ to 5 moles, or more preferably $1\times10^{-4}$ to 1 mole, relative to 1 mole of the monomer.

Amount of water to obtain the silicon-containing surface modifier by the hydrolytic condensation of these monomers is preferably 0.01 to 100 moles, more preferably 0.05 to 50 moles, or still more preferably 0.1 to 30 moles, relative to 1 mole of the hydrolysable subtituent which is bonded to the monomer. When the amount is not more than 100 moles, small equipment can be used for the reaction; and thus, it is economical.

Operational procedure of adding the monomer into an aqueous catalyst solution is employed to start the hydrolitic condensation reaction. At this time, an organic solvent may be added in the aqueous catalyst solution, or the monomer may be diluted by an organic solvent, or both of them may be done. The reaction temperature is 0 to 100° C., or preferably 5 to 80° C. A method, wherein the temperature thereof is kept at 5 to 80° C. during the time of drop of the monomer, and then, aging is done at 20 to 80° C., is preferable.

Preferable example of the organic solvent which can be added to the aqueous catalyst solution or can dilute the monomer includes methanol, ethanol, 1-propanol, 2-propanol, 1-butanol, 2-butanol, 2-methyl-1-propanol, acetone, acetonitrile, tetrahydrofuran, toluene, hexane, ethyl acetate, methyl ethyl ketone, methyl isobutyl ketone, cyclohexanone, methyl amyl ketone, butanediol monomethyl ether, propylene glycol monomethyl ether, ethylene glycol monomethyl ether, butanediol monoethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, γ-butyrolactone, and a mixture of these solvents.

Among these solvents, a water-soluble solvent is preferable. Illustrative example thereof includes an alcohol such as methanol, ethanol, 1-propanol, and 2-propanol; a polyol such as ethylene glycol and propylene glycol; a polyol condensation derivative such as butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, and ethylene glycol monopropyl ether; acetone, acetonitrile, and tetrahydrofuran. Among them, a solvent having a boiling point of 100° C. or lower is particularly preferable.

Meanwhile, use amount of the organic solvent is preferably 0 to 1,000 mL, or especially preferably 0 to 500 mL, relative to 1 mole of the monomer. Less use amount of the organic solvent is more economical because its reaction vessel becomes smaller.

Thereafter, a neutralization reaction of the catalyst is carried out, if necessary, to obtain an aqueous reaction mixture solution. Use amount of a alkali substance for neutralization is preferably 0.1 to 2 equivalents relative to the acid used as the catalyst. Any alkali substance may be used as far as the substance shows a alkali property in water.

Then, it is preferable to remove byproducts such as an alcohol produced by the hydrolytic condensation reaction from the reaction mixture under reduced pressure or the like. Temperature to heat the reaction mixture in this operation is preferably 0 to 100° C., more preferably 10 to 90° C., or still more preferably 15 to 80° C., though it depends on kinds of an added organic solvent and an alcohol produced by the reaction. Degree of the vacuum in this operation is preferably an atmospheric pressure or lower, more preferably 80 kPa or lower in the absolute pressure, or still more preferably 50 kPa or lower in the absolute pressure, though it depends on kinds of an organic solvent and an alcohol and so forth to be removed, an exhausting equipment, a condensation apparatus, and heating temperature. Although it is difficult to know exactly an amount of the alcohol removed, it is preferable that about 80% or more by mass of a produced alcohol and so forth be removed.

Then, the acid catalyst used in the hydrolytic condensation reaction may be removed from the reaction mixture. The acid catalyst may be removed by mixing the silicon-containing surface modifier with water, and then extracting the silicon-containing surface modifier by an organic solvent. The organic solvent which can dissolve the silicon-containing surface modifier while can be separated into two layers when mixed with water is preferably used. Illustrative example of the organic solvent includes methanol, ethanol, 1-propanol, 2-propanol, 1-butanol, 2-butanol, 2-methyl-1-propanol, acetone, tetrahydrofuran, toluene, hexane, ethyl acetate, cyclohexanone, methyl amyl ketone, butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, t-butyl acetate, t-butyl propionate, propylene glycol mono-t-butyl ether acetate, γ-butyrolactone, methyl isobutyl ketone, cyclopentyl methyl ether, and a mixture of them.

In addition, a mixture of a water-soluble organic solvent and a water-insoluble organic solvent may also be used. Illustrative examples of the preferable mixture include a mixture of methanol and ethyl acetate, a mixture of ethanol and ethyl acetate, a mixture of 1-propanol and ethyl acetate, a mixture of 2-propanol and ethyl acetate, a mixture of butanediol monomethyl ether and ethyl acetate, a mixture of propylene glycol monomethyl ether and ethyl acetate, a mixture of ethylene glycol monomethyl ether and ethyl acetate, a mixture of butanediol monoethyl ether and ethyl acetate, a mixture of propylene glycol monoethyl ether and ethyl acetate, a mixture of ethylene glycol monoethyl ether and ethyl acetate, a mixture of butanediol monopropyl ether and ethyl acetate, a mixture of propylene glycol monopropyl ether and ethyl acetate, a mixture of ethylene glycol monopropyl ether and ethyl acetate, a mixture of methanol and methyl isobutyl ketone, a mixture of ethanol and methyl isobutyl ketone, a mixture of 1-propanol and methyl isobutyl ketone, a mixture of 2-propanol and methyl isobutyl ketone, a mixture of propylene glycol monomethyl ether and methyl isobutyl ketone, a mixture of ethylene glycol monomethyl ether and methyl isobutyl ketone, a mixture of propylene glycol monoethyl ether and methyl isobutyl ketone, a mixture of ethylene glycol monoethyl ether and methyl isobutyl ketone, a mixture of propylene glycol monopropyl ether and methyl isobutyl ketone, a mixture of ethylene glycol monopropyl ether and methyl isobutyl ketone, a mixture of methanol and cyclopentyl methyl ether, a mixture of ethanol and cyclopentyl methyl ether, a mixture of 1-propanol and cyclopentyl methyl ether, a mixture of 2-propanol and cyclopentyl methyl ether, a mixture of propylene glycol monomethyl ether and cyclopentyl methyl ether, a mixture of ethylene glycol monomethyl ether and cyclopentyl methyl ether, a mixture of propylene glycol monoethyl ether and cyclopentyl methyl ether, a mixture of ethylene glycol monoethyl ether and cyclopentyl methyl ether, a mixture of propylene glycol monopropyl ether and cyclopentyl methyl ether, a mixture of ethylene glycol monopropyl ether and cyclopentyl methyl ether, a mixture of methanol and propylene glycol methyl ether acetate, a mixture of ethanol and propylene glycol methyl ether acetate, a mixture of 1-propanol and propylene glycol methyl ether acetate, a mixture of 2-propanol and propylene glycol methyl ether acetate, a mixture of propylene glycol monomethyl ether and propylene glycol methyl ether acetate, a mixture of ethylene glycol monomethyl ether and propylene glycol methyl ether acetate, a mixture of propylene glycol monoethyl ether and propylene glycol methyl ether acetate, a mixture of ethylene glycol monoethyl ether and propylene glycol methyl ether acetate, a mixture of propylene glycol monopropyl ether and propylene glycol methyl ether acetate, and a mixture of ethylene glycol monopropyl ether and propylene glycol methyl ether acetate, though the combination is not limited to the above.

Meanwhile, mixing ratio of the water-soluble organic solvent to the water-insoluble organic solvent is appropriately selected; but the amount of the water-soluble organic solvent is 0.1 to 1,000 parts by mass, preferably 1 to 500 parts by mass, or more preferably 2 to 100 parts by mass, relative to 100 parts by mass of the water-insoluble organic solvent.

Then, washing by neutral water may be done. So-called de-ionized water or ultrapure water may be used. Amount of this water is 0.01 to 100 liters, preferably 0.05 to 50 liters, more preferably 0.1 to 5 liters, relative to 1 liter of the silicon-containing surface modifier solution. This washing operation may be done in such a way that the both solutions are mixed in a vessel by agitation, and then settled to separate a water layer. Number of washing is 1 or more, or preferably about 1 to about 5, because washing of 10 times or more is not worth to have full effects.

Alternatively, the acid catalyst may be removed by use of an ion-exchange resin, or in such a way that it is neutralized by an epoxy compound such as ethylene oxide and propylene oxide, and then removed. These methods may be selected appropriately according to the acid catalyst used in the reaction.

In this operation of water-washing, number of washing and amount of water for washing may be determined appropriately in view of effects of catalyst removal and fractionation because there is an instance that a part of the silicon-containing surface modifier escapes into a water layer, thereby substantially the same effect as fractionation operation can be obtained.

To any of the silicon-containing surface modifier solution having the remaining acid catalyst and the silicon-containing surface modifier solution having the acid catalyst removed therefrom is added a final solvent, and then the solvents therein are exchanged under reduced pressure to obtain an intended solution of the silicon-containing surface modifier. Temperature at the time of this solvent exchange operation is preferably 0 to 100° C., more preferably 10 to 90° C., or still more preferably 15 to 80° C., though it is depending on the reaction solvent and the extraction solvent to be removed. Degree of the vacuum in this operation is preferably an atmospheric pressure or lower, more preferably 80 kPa or lower in the absolute pressure, or still more preferably 50 kPa or lower in the absolute pressure, though it depends on kinds of the extraction solvent to be removed, an exhausting equipment, a condensation equipment, and heating temperature.

In this operation, there is a case that the silicon-containing surface modifier becomes unstable by the solvent exchange. This occurs depending on compatibility of a final solvent with the silicon-containing surface modifier; and in order to prevent this from occurring, an alcohol having a cyclic ether substituent with the valency thereof being one, or two or higher, examples thereof being described in paragraphs of [0181] to [0182] in the Japanese Patent Laid-Open Publication No. 2009-126940, may be added as a stabilizer. Adding amount thereof is 0 to 25 parts by mass, preferably 0 to 15 parts by mass, and more preferably 0 to 5 parts by mass, or 0.5 parts or more by mass when it is added, relative to 100 parts by mass of the silicon-containing surface modifier contained in the solution before the solvent exchange. The solvent exchange may be done, if necessary, by adding an alcohol having a cyclic ether substituent with the valency thereof being one, or two or higher into the solution before the solvent exchange.

There is a risk that the silicon-containing surface modifier undergoes a condensation reaction further when it is concentrated beyond a certain concentration level whereby changing to the state where it cannot be dissolved into an organic solvent again; and thus, it is preferable that the modifier be kept in the state of solution with proper concentration. However, if the concentration thereof is too dilute, amount of the solvent becomes excessively large; and thus, to keep the solution in the state of proper concentration is economical and preferable. The concentration thereof at this time is preferably in the range of 0.1 to 20% by mass.

A preferable solvent finally added to the silicon-containing surface modifier solution is an alcohol solvent; and especially preferable solvents thereof are monoalkyl ether derivatives of ethylene glycol, diethylene glycol, triethylene glycol, propylene glycol, dipropylene glycol, butanediol, and so on. Specific example of the preferable solvent includes butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, and ethylene glycol monopropyl ether.

Alternatively, if these solvents are a main solvent, a nonalcoholic solvent may be added thereinto as an adjuvant solvent. Illustrative example of this adjuvant solvent includes acetone, tetrahydrofuran, toluene, hexane, ethyl acetate, cyclohexanone, methyl amyl ketone, propylene glycol dimethyl ether, diethylene glycol dimethyl ether, propylene glycol monomethyl ether acetate, propylene glycol monoethyl ether acetate, ethyl pyruvate, butyl acetate, methyl 3-methoxypropionate, ethyl 3-ethoxypropionate, t-butyl acetate, t-butyl propionate, propylene glycol mono-t-butyl ether acetate, γ-butyrolactone, methyl isobutyl ketone, and cyclopentyl methyl ether.

In an alternative operational procedure using an acid catalyst, the hydrolysis reaction is started by adding water or a water-containing organic solvent into a monomer or into an organic solution of a monomer. In this operation, the catalyst may be added into the monomer or the organic solution of the monomer, or into water or the water-containing organic solvent. The reaction temperature is 0 to 100° C., or preferably 10 to 80° C. A method, wherein the temperature thereof is kept at 10 to 50° C. during the time of drop of water, and then, aging is done at 20 to 80° C., is preferable.

When the organic solvent is used, a water-soluble solvent is preferable. Illustrative example thereof includes methanol, ethanol, 1-propanol, 2-propanol, 1-butanol, 2-butanol, 2-methyl-1-propanol, acetone, tetrahydrofuran, and acetonitrile; a polyol condensation derivative such as butanediol monomethyl ether, propylene glycol monomethyl ether, ethylene glycol monomethyl ether, butanediol monoethyl ether, propylene glycol monoethyl ether, ethylene glycol monoethyl ether, butanediol monopropyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, and propylene glycol monopropyl ether acetate; and a mixture of these solvents.

Use amount of these organic solvents is preferably 0 to 1,000 mL, or especially preferably 0 to 500 mL, relative to 1 mole of the monomer. Less use amount of the organic solvent is more economical because the reaction vessel thereof becomes smaller. Work-up of the reaction mixture thus obtained is done in a manner similar to those mentioned before, whereby obtaining the silicon-containing surface modifier.

1-2. Synthesis Method 2: Alkali Catalyst

Alternatively, the silicon-containing surface modifier may be produced, for example, by hydrolytic condensation of one or a mixture of two or more kinds of the hydrolysable monomer mentioned above in the presence of an alkali catalyst.

Illustrative example of the alkali catalyst used in this operation includes methylamine, ethylamine, propylamine, butylamine, ethylene diamine, hexamethylene diamine, dimethylamine, diethylamine, ethyl methyl amine, trimethylamine, triethylamine, tripropylamine, tributylamine, cyclohexylamine, dicyclohexylamine, monoethanol amine, diethanol amine, dimethyl monoethanol amine, monomethyl diethanol amine, triethanol amine, diazabicyclooctane, diazabicyclononene, diazabicycloundecene, hexamethylene tetramine, aniline, N,N-dimethylaniline, pyridine, N,N-dimethylaminopyridine, pyrrole, piperazine, pyrrolidine, piperidine, picoline, tetramethyl ammonium hydroxide, cholin hydroxide, tetrapropyl ammonium hydroxide, tetrabutyl ammonium hydroxide, ammonia, lithium hydroxide, sodium hydroxide, potassium hydroxide, barium hydroxide, and calcium hydroxide. Use amount of the catalyst is $1 \times 10^{-6}$ to 10 moles, preferably $1 \times 10^{-5}$ to 5 moles, or more preferably $1 \times 10^{-4}$ to 1 mole, relative to 1 mole of the silicon monomer.

Amount of water to obtain the silicon-containing surface modifier by the hydrolitic condensation reaction of the foregoing monomers is preferably 0.1 to 50 moles, relative to 1 mole of the hydrolysable subtituent which is bonded to the monomer. When the amount is not more than 50 moles, small equipment can be used for the reaction; and thus, it is economical.

Operational procedure of adding the monomer into an aqueous catalyst solution is employed to start the hydrolitic condensation reaction. At this time, an organic solvent may be added in the aqueous catalyst solution, or the monomer may be diluted by an organic solvent, or both of them may be done. The reaction temperature is 0 to 100° C., or preferably 5 to 80° C. A method, wherein the temperature thereof is kept at 5 to 80° C. during the time of drop of the monomer, and then, aging is done at 20 to 80° C., is preferable.

Preferable organic solvents which can be added to the aqueous alkali catalyst solution or can dilute the monomer are similar to those mentioned as the examples of the organic solvent which can be added into the aqueous acid catalyst solution. Meanwhile, use amount of the organic solvent is preferably 0 to 1,000 mL relative to 1 mole of the monomer to carry out the reaction economically.

Thereafter, a neutralization reaction of the catalyst is carried out, if necessary, to obtain an aqueous reaction mixture solution. Use amount of an acidic substance for neutralization is preferably 0.1 to 2 equivalents relative to the alkaline substance used as the catalyst. Any acidic substance may be used as far as the substance shows an acidic property in water.

Then, it is preferable to remove byproducts such as an alcohol produced by the hydrolytic condensation reaction from the reaction mixture under reduced pressure or the like. Temperature to heat the reaction mixture in this operation is preferably 0 to 100° C., more preferably 10 to 90° C., or still more preferably 15 to 80° C., though it depends on kinds of the added organic solvent and the alcohol produced by the reaction. Degree of the vacuum in this operation is preferably an atmospheric pressure or lower, more preferably 80 kPa or lower in the absolute pressure, or still more preferably 50 kPa or lower in the absolute pressure, though it depends on kinds of the organic solvent and the alcohol to be removed, an exhausting equipment, a condensation apparatus, and heating temperature. Although it is difficult to know exactly an amount of the alcohol removed, it is preferable that about 80% or more by mass of a produced alcohol be removed.

Then, to remove the alkali catalyst used in the hydrolitic condensation reaction, the silicon-containing surface modifier is extracted by an organic solvent. An organic solvent which can dissolve the silicon-containing surface modifier while can be separated into two layers when mixed with water is preferably used. Alternatively, a mixture of a water-soluble organic solvent and a water-insoluble organic solvent may be used.

Specific examples of the organic solvent which can be used to remove the alkali catalyst are similar to the organic solvents and the mixture of a water-soluble organic solvent and a water-insoluble organic solvent which were specifically shown to remove the acid catalyst previously.

Meanwhile, mixing ratio of the water-soluble organic solvent to the water-insoluble organic solvent is appropriately selected; but the amount of the water-soluble organic solvent is 0.1 to 1,000 parts by mass, preferably 1 to 500 parts by mass, or more preferably 2 to 100 parts by mass, relative to 100 parts by mass of the water-insoluble organic solvent.

Then, washing is done by neutral water. So-called deionized water or ultrapure water may be used. Amount of this water is 0.01 to 100 liters, preferably 0.05 to 50 liters, or more preferably 0.1 to 5 liters, relative to 1 liter of the silicon-containing surface modifier solution. This washing operation may be done in such a way that the both solutions are mixed in a vessel by agitation, and then settled to separate a water layer. Number of washing is 1 or more, or preferably about 1 to about 5, because washing of 10 times or more is not worth to have full effects.

To the silicon-containing surface modifier solution after washing is added a final solvent, and then solvents therein are exchanged under reduced pressure to obtain an intended solution containing the silicon-containing surface modifier. Temperature at the time of the solvent exchange is preferably 0 to 100° C., more preferably 10 to 90° C., or still more preferably 15 to 80° C., though it depends on the extraction solvent to be removed. Degree of the vacuum in this operation is preferably an atmospheric pressure or lower, more preferably 80 kPa or lower in the absolute pressure, or still more preferably 50 kPa or lower in the absolute pressure, though it depends on kinds of the extraction solvent to be removed, an exhausting equipment, a condensation apparatus, and heating temperature.

A preferable solvent finally added to the silicon-containing surface modifier solution is an alcohol solvent; and especially preferable solvents thereof are a monoalkyl ether of ethylene glycol, diethylene glycol, triethylene glycol, and so on; and a monoalkyl ether of propylene glycol, dipropylene glycol, and so on. Specific example of the preferable solvent includes propylene glycol monomethyl ether, ethylene glycol monomethyl ether, propylene glycol monoethyl ether, ethylene glycol monoethyl ether, propylene glycol monopropyl ether, and ethylene glycol monopropyl ether.

In an alternative operational procedure using an alkali catalyst, the hydrolysis reaction is started by adding water or a water-containing organic solvent into a monomer or into an organic solution of a monomer. In this operation, the catalyst may be added into the monomer or into the organic solution of the monomer, or into water or the water-containing organic solvent. The reaction temperature is 0 to 100° C., or preferably 10 to 80° C. A method, wherein the temperature thereof is kept at 10 to 50° C. during the time of drop of water, and then, aging is done at 20 to 80° C., is preferable.

The organic solvent which can be used in the organic solution of the monomer or in the water-containing organic solvent is preferably water-soluble; and illustrative example thereof includes methanol, ethanol, 1-propanol, 2-propanol, 1-butanol, 2-butanol, 2-methyl-1-propanol, acetone, tetrahydrofuran, and acetonitrile; a polyol condensation derivative such as propylene glycol monomethyl ether, ethylene glycol monomethyl ether, propylene glycol monoethyl ether, ethylene glycol monoethyl ether, propylene glycol monopropyl ether, ethylene glycol monopropyl ether, propylene glycol dimethyl ether, diethylene glycol dimethyl ether, propylene glycol monomethyl ether acetate, propylene glycol monoethyl ether acetate, and propylene glycol monopropyl ether acetate; and a mixture of these solvents.

Molecular weight of silicon-containing surface modifier obtained by the Synthesis Methods 1 or 2 mentioned above can be controlled not only by selection of the monomer but also by control of reaction conditions during the time of polymerization, wherein the molecular weight thereof is preferably 100,000 or less, more preferably 200 to 50,000, or still more preferably 300 to 30,000. When the weight-average molecular weight is 100,000 or less, foreign matters or coating smear may not be formed.

Meanwhile, the data of the weight-average molecular weight are of the polystyrene-equivalent molecular weight based on the standard polystyrene, wherein the data are obtained by a gel permeation chromatography (GPC) using RI as a detector and tetrahydrofuran as an eluting solvent.

Further, the present invention provides a silicon-containing resist underlayer film composition which contains the silicon-containing surface modifier of the present invention as mentioned above and a polysiloxane compound.

Blending amount of the silicon-containing surface modifier therein is 0.01 to 50, or preferably 0.1 to 10, as the mass ratio relative to 100 of the base polymer polysiloxane compound.

The polysiloxane compound contained in the resist underlayer film composition prepared by using the silicon-containing surface modifier of the present invention may be produced, for example, under the condition of treating the aforementioned other hydrolysable monomers by using an acid or an alkali catalyst.

In addition, a polysiloxane derivative which is produced from a mixture of this monomer with a hydrolysable metal compound shown by the following general formula (2) under the condition of using the foregoing acid or alkali catalyst may be used as a component of the resist underlayer film composition,

$$U(OR^7)_{m7}(OR^8)_{m8} \qquad (2)$$

wherein $R^7$ and $R^8$ represent an organic group having 1 to 30 carbon atoms; m7+m8 is a number which is equal to a valency that is determined by U; m7 and m8 represent an integer of 0 or more; and U represents elements belonging to the groups III, IV, or V in the periodic table except for carbon and silicon elements.

Illustrative example of the hydrolysable metal compound (2) used therein includes the following compounds.

In the case that U is boron, illustrative example of the compound shown by the general formula (2) includes, as the monomer, boron methoxide, boron ethoxide, boron propoxide, boron butoxide, boron amyloxide, boron hexyloxide, boron cyclopentoxide, boron cyclohexyloxide, boron allyloxide, boron phenoxide, boron methoxyethoxide, boric acid, and boron oxide.

In the case that U is an aluminum, illustrative example of the compound shown by the general formula (2) includes, as the monomer, aluminum methoxide, aluminum ethoxide, aluminum propoxide, aluminum butoxide, aluminum amyloxide, aluminum hexyloxide, aluminum cyclopentoxide, aluminum cyclohexyloxide, aluminum allyloxide, aluminum phenoxide, aluminum methoxyethoxide, aluminum ethoxyethoxide, aluminum dipropoxyethyl acetoacetate, aluminum dibutoxyethyl acetoacetate, aluminum propoxy bisethyl acetoacetate, aluminum butoxy bisethyl acetoacetate, aluminum 2,4-pentanedionate, and aluminum 2,2,6,6-tetramethyl-3,5-heptanedionate.

In the case that U is a gallium, illustrative example of the compound shown by the general formula (2) includes, as the monomer, gallium methoxide, gallium ethoxide, gallium propoxide, gallium butoxide, gallium amyloxide, gallium hexyloxide, gallium cyclopentoxide, gallium cyclohexyloxide, gallium allyloxide, gallium phenoxide, gallium methoxyethoxide, gallium ethoxyethoxide, gallium dipropoxyethyl acetoacetate, gallium dibutoxyethyl acetoacetate, gallium propoxy bisethyl acetoacetate, gallium butoxy bisethyl acetoacetate, gallium 2,4-pentanedionate, and gallium 2,2,6,6-tetramethyl-3,5-heptanedionate.

In the case that U is a yttrium, illustrative example of the compound shown by the general formula (2) includes, as the monomer, yttrium methoxide, yttrium ethoxide, yttrium propoxide, yttrium butoxide, yttrium amyloxide, yttrium hexyloxide, yttrium cyclopentoxide, yttrium cyclohexyloxide, yttrium allyloxide, yttrium phenoxide, yttrium methoxyethoxide, yttrium ethoxyethoxide, yttrium dipropoxyethyl acetoacetate, yttrium dibutoxyethyl acetoacetate, yttrium propoxy bisethyl acetoacetate, yttrium butoxy bisethyl acetoacetate, yttrium 2,4-pentanedionate, and yttrium 2,2,6,6-tetramethyl-3,5-heptanedionate.

In the case that U is a germanium, illustrative example of the compound shown by the general formula (2) includes, as the monomer, germanium methoxide, germanium ethoxide, germanium propoxide, germanium butoxide, germanium amyloxide, germanium hexyloxide, germanium cyclopentoxide, germanium cyclohexyloxide, germanium allyloxide, germanium phenoxide, germanium methoxyethoxide, and germanium ethoxyethoxide.

In the case that U is a titanium, illustrative example of the compound shown by the general formula (2) includes, as the monomer, titanium methoxide, titanium ethoxide, titanium propoxide, titanium butoxide, titanium amyloxide, titanium hexyloxide, titanium cyclopentoxide, titanium cyclohexyloxide, titanium allyloxide, titanium phenoxide, titanium methoxyethoxide, titanium ethoxyethoxide, titanium dipropoxy bisethyl acetoacetate, titanium dibutoxy bisethyl acetoacetate, titanium dipropoxy bis-2,4-pentanedionate, and titanium dibutoxy bis-2,4-pentanedionate.

In the case that U is a hafnium, illustrative example of the compound shown by the general formula (2) includes, as the monomer, hafnium methoxide, hafnium ethoxide, hafnium propoxide, hafnium butoxide, hafnium amyloxide, hafnium hexyloxide, hafnium cyclopentoxide, hafnium cyclohexyloxide, hafnium allyloxide, hafnium phenoxide, hafnium methoxyethoxide, hafnium ethoxyethoxide, hafnium dipropoxy bisethyl acetoacetate, hafnium dibutoxy bisethyl acetoacetate, hafnium dipropoxy bis-2,4-pentanedionate, and hafnium dibutoxy bis-2,4-pentanedionate.

In the case that U is a tin, illustrative example of the compound shown by the general formula (2) includes, as the monomer, methoxy tin, ethoxy tin, propoxy tin, butoxy tin, phenoxy tin, methoxyethoxy tin, ethoxyethoxy tin, tin 2,4-pentanedionate, and tin 2,2,6,6-tetramethyl-3,5-heptanedionate.

In the case that U is an arsenic, illustrative example of the compound shown by the general formula (2) includes, as the monomer, methoxy arsenic, ethoxy arsenic, propoxy arsenic, butoxy arsenic, and phenoxy arsenic.

In the case that U is an antimony, illustrative example of the compound shown by the general formula (2) includes, as the monomer, methoxy antimony, ethoxy antimony, propoxy antimony, butoxy antimony, phenoxy antimony, antimony acetate, and antimony propionate.

In the case that U is a niobium, illustrative example of the compound shown by the general formula (2) includes, as the monomer, methoxy niobium, ethoxy niobium, propoxy niobium, butoxy niobium, and phenoxy niobium.

In the case that U is a tantalum, illustrative example of the compound shown by the general formula (2) includes, as the monomer, methoxy tantalum, ethoxy tantalum, propoxy tantalum, butoxy tantalum, and phenoxy tantalum.

In the case that U is a bismuth, illustrative example of the compound shown by the general formula (2) includes, as the monomer, methoxy bismuth, ethoxy bismuth, propoxy bismuth, butoxy bismuth, and phenoxy bismuth.

In the case that U is a phosphorous, illustrative example of the compound shown by the general formula (2) includes, as the monomer, trimethyl phosphate, triethyl phosphate, tripropyl phosphate, trimethyl phosphite, triethyl phosphite, tripropyl phosphite, and diphosphorous pentaoxide.

In the case that U is a vanadium, illustrative example of the compound shown by the general formula (2) includes, as the monomer, vanadium oxide bis(2,4-pentanedionate), vanadium 2,4-pentanedionate, vanadium tributoxide oxide, and vanadium tripropoxide oxide.

In the case that U is a zirconium, illustrative example of the compound shown by the general formula (2) includes, as the monomer, methoxy zirconium, ethoxy zirconium, propoxy zirconium, butoxy zirconium, phenoxy zirconium, zirconium dibutoxide bis(2,4-pentanedionate), and zirconium dipropoxide bis(2,2,6,6-tetramethyl-3,5-heptanedionate).

As to the polysiloxane compound, it is preferable that content of a component derived from the four-functional hydrolysable monomer be 70 mole % or more as the component in the polysiloxane compound.

2. Other Components 2-1. Thermal Crosslinking Accelerator

In the present invention, a thermal crosslinking accelerator may be blended to the silicon-containing resist underlayer film composition. Examples of the thermal crosslinking accelerator which can be blended therein are compounds shown by the following general formula (3) or (4). Specific examples thereof are those described in the Japanese Patent Laid-Open Publication No. 2007-302873,

$$L_aH_bX \qquad (3)$$

wherein L represents any of lithium, sodium, potassium, rubidium, and cesium; X represents a hydroxyl group, or an organic acid group having 1 to 30 carbon atoms with the valency thereof being one, or two or higher; a represents an integer of 1 or more, b represents 0 or an integer of 1 or more, and a+b is a valency of the hydroxyl group or the organic acid group,

$$MY \qquad (4)$$

wherein M represents any of sulfonium, iodonium, and ammonium; and Y represents a non-nucleophilic counter ion.

Meanwhile, the foregoing thermal crosslinking accelerators may be used solely or in a combination of two or more of them. Adding amount of the thermal crosslinking accelerator is preferably 0.01 to 50 parts by mass, or more preferably 0.1 to 40 parts by mass, relative to 100 parts by mass the base polymer polysiloxane.

2-2. Organic Acids

To improve stability of the silicon-containing resist underlayer film composition of the present invention, it is preferable to add an organic acid having 1 to 30 carbon atoms with the valency thereof being one, or two or higher be added thereinto. Illustrative example of the acid to be added herein includes formic acid, acetic acid, propionic acid, butanoic acid, pentanoic acid, hexanoic acid, heptanoic acid, octanoic acid, nonanoic acid, decanoic acid, oleic acid, stearic acid, linoleic acid, linolenic acid, benzoic acid, phthalic acid, isophthalic acid, terephthalic acid, salicylic acid, trifluoroacetic acid, monochloroacetic acid, dichloroacetic acid, trichloroacetic acid, oxalic acid, malonic acid, methylmalonic acid, ethylmalonic acid, propylmalonic acid, butylmalonic acid, dimethylmalonic acid, diethylmalonic acid, succinic acid, methylsuccinic acid, glutaric acid, adipic acid, itaconic acid, maleic acid, fumaric acid, citraconic acid, and citric acid. Especially, oxalic acid, maleic acid, formic acid, acetic acid, propionic acid, citric acid, and the like are preferable. To keep storage stability, two or more kinds of these acids may be used as a mixture. Adding amount thereof is 0.001 to 25 parts by mass, preferably 0.01 to 15 parts by mass, or more preferably 0.1 to 5 parts by mass, relative to 100 parts by mass of silicon which is contained in the composition.

Alternatively, the above-mentioned organic acid is added such that pH of the composition may become preferably $0 \leq pH \leq 7$, more preferably $0.3 \leq pH \leq 6.5$, or still more preferably $0.5 \leq pH \leq 6$.

2-3. Water

In the present invention, water may be added to the composition. When water is added thereinto, the polysiloxane compound in the composition is hydrated whereby improving a lithography performance. Water content in the solvent component of the composition is 0 to 50% by mass (both not inclusive), especially preferably 0.3 to 30% by mass, or still further more preferably 0.5 to 20% by mass. In each component, if water amount is too large, uniformity of the silicon-containing resist underlayer film is deteriorated thereby causing a risk of an eye hole in the worst case. On the other hand, if water amount is too small, there is a risk of deterioration in the lithography performance.

Use amount of entirety of the solvent including water is preferably 100 to 100,000 parts by mass, or especially preferably 200 to 50,000 parts by mass, relative to 100 parts by mass of the base polymer polysiloxane compound.

2-4. Photo-Sensitive Acid Generator

In the present invention, a photo-sensitive acid generator may be added to the composition. Specifically photo-sensitive acid generators which are described in paragraphs of [0160] to [0179] of the Japanese Patent Laid-Open Publication No. 2009-126940 may be used in the present invention.

2-5. Stabilizer

In addition, in the present invention, a stabilizer may be added to the composition. A stabilizer of an alcohol having a cyclic ether substituent with the valency thereof being one, or two or higher may be added. Especially, addition of stabilizers described in paragraphs [0181] to [0182] of the Japanese Patent Laid-Open Publication No. 2009-126940 can improve stability of the silicon-containing resist underlayer film composition.

2-6. Surfactant

Further, in the present invention, a surfactant may be added to the composition if necessary. Specific examples thereof are those materials described in paragraph [0185] of the Japanese Patent Laid-Open Publication No. 2009-126940.

2-7. Other Component

Further, in the present invention, a high boiling point solvent having a boiling point of 180° C. or higher may be added to the composition if necessary. Illustrative example of this high boiling point solvent includes 1-octanol, 2-ethylhexanol, 1-nonanol, 1-decanol, 1-undecanol, ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropyelene glycol, glycerin, n-nonyl acetate, ethylene glycol monoethyl ether acetate, γ-butyrolactone, 1,2-diacetoxyethane, 1-acetoxy-2-methoxyethane, 1,2-diacetoxypropane, diethylene glycol monomethyl ether acetate, diethylene glycol monoethyl ether acetate, diethylene glycol mono-n-butyl ether acetate, propylene glycol monomethyl ether acetate, propylene glycol monopropyl ether acetate, propylene glycol monobutyl ether acetate, dipropylene glycol monomethyl ether acetate, and dipropylene glycol monoethyl ether acetate.

If the high boiling solvent having a boiling point of 180° C. or higher is contained therein, a resist underlayer film having good adhesion to the upper layer resist pattern may be formed.

3. Negative Patterning Process

3-1. Negative Patterning Process 1

The present invention provides a patterning process, wherein, an organic underlayer film is formed on a body to be processed by using an application-type organic underlayer film composition, a silicon-containing resist underlayer film is formed on the organic underlayer film by using the above-mentioned silicon-containing resist underlayer film composition, a photoresist film is formed on the silicon-containing resist underlayer film by using a chemically amplifying type resist composition, after heat treatment the photoresist film is exposed to a high energy beam, a negative pattern is formed by dissolving an unexposed area of the photoresist film by using an organic solvent developer, the pattern is transferred to the silicon-containing resist underlayer film by dry etching by using the photoresist film formed with the negative pattern as a mask, the pattern is transferred by dry etching of the organic underlayer film by using the silicon-containing resist underlayer film transferred with the pattern as a mask, and then the pattern is transferred to the body to be processed by dry etching by using the organic underlayer film transferred with the pattern as a mask (so-called "multilayer resist method").

3-2. Negative Patterning Process 2

Provided further is a patterning process, wherein, an organic hard mask mainly composed of carbon is formed on a body to be processed by a CVD method, a silicon-containing resist underlayer film is formed on the organic hard mask by using the above-mentioned silicon-containing resist underlayer film composition, a photoresist film is formed on the silicon-containing resist underlayer film by using a chemically amplifying type resist composition, after heat treatment the photoresist film is exposed to a high energy beam, a negative pattern is formed by dissolving an unexposed area of the photoresist film by using an organic solvent developer, the pattern is transferred to the silicon-containing resist underlayer film by dry etching by using the photoresist film formed with the negative pattern as a mask, the pattern is transferred by dry etching of the organic hard mask by using the silicon-containing resist underlayer film transferred with the pattern as a mask, and then the pattern is transferred to the body to be processed by dry etching by using the organic hard mask transferred with the pattern as a mask.

When the negative pattern is formed by using the resist underlayer film of the present invention, the pattern formed in the photoresist can be formed on the substrate without causing transfer difference in size by optimizing a combination of the CVD film and the organic underlayer film as mentioned above.

In addition, in photo-exposure of the photoresist film, it is preferable that Contact angle of the part of the silicon-containing resist underlayer film after exposure which corresponds to the exposed area of the exposed photoresist film be decreased by 10 degrees or more as compared with before photo-exposure.

When contact angle of the exposed area of the silicon-containing resist underlayer film is decreased by 10 degrees or more as compared with before photo-exposure, difference in the contact angle to the resist pattern after the negative development becomes smaller, whereby leading to enhancement of adhesion; and as a result, pattern fall can be avoided, and a fine pattern can be formed.

The silicon-containing resist underlayer film which is used in patterning process of the present invention can be formed on the body to be processed from the silicon-containing resist underlayer film composition of the present invention by a spin coating method and the like, similarly to the photoresist film. After spin coating, it is preferable to carry out baking in order to evaporate a solvent, to avoid mixing with the photoresist film, and to accelerate the crosslinking reaction. This baking is done preferably in the temperature range of 50 to 500° C. and the time of 10 to 300 seconds. Especially preferable temperature thereof is 400° C. or lower in order to decrease a thermal damage to a device, though the temperature is depending on structure of the device to be manufactured.

Here, as the body to be processed, a substrate for a semiconductor device, or a substrate for a semiconductor device coated, as the film to be processed (as the part to be processed), with any of a metal film, a metal alloy film, a metal carbide film, a metal oxide film, a metal nitride film, a metal oxide carbide film, and a metal oxide nitride film, may be used.

As to the substrate for a semiconductor device, a silicon substrate is generally used, though not particularly limited thereto; and materials having different properties from those of the film to be processed, such as Si, amorphous silicon ($\alpha$-Si), p-Si, $SiO_2$, SiN, SiON, W, TiN, and Al, may be used.

As to the metal to constitute the body to be processed, any of silicon, gallium, titanium, tungsten, hafnium, zirconium, chromium, germanium, copper, aluminum, and iron, or a metal alloy of them may be used. As to the layer to be processed which contains these metals, illustrative example thereof includes Si, $SiO_2$, SiN, SiON, SiOC, p-Si, $\alpha$-Si, TiN, WSi, BPSG, SOG, Cr, CrO, CrON, MoSi, W, W—Si, Al, Cu, Al—Si, various kinds of a low dielectric film, and an etching stopper film thereof, wherein they may be formed with the film thickness of usually 50 to 10,000 nm, in particular 100 to 5,000 nm.

In the negative patterning process of the present invention, the photoresist film is not particularly restricted provided that it is of a chemically amplifying type to give a negative pattern by development using an organic solvent developer.

In the photo-exposure process of the present invention, for example, if the exposure process by an ArF excimer laser beam is used, a photoresist film of any usual resist composition for an ArF excimer laser beam can be used.

Many candidates for the resist composition for an ArF excimer laser beam like this have already been in the public domain, wherein the heretofore known resins can be classified roughly into a poly(meth)acryl type, a COMA type (COMA: Cyclo Olefin Maleic Anhydride), a COMA-(meth) acryl hybrid type, a ROMP type (ROMP: Ring Opening Methathesis Polymerization), a polynorbornene type, and so forth; among them, a resist composition which uses a poly (meth)acryl type resin has better resolution than the other resin types because an aliphatic skeleton is introduced to its side chain thereby securing the etching resistance thereof.

In the negative patterning process, after the silicon-containing resist underlayer film is formed, the photoresist film is formed thereonto by using a photoresist composition solution, wherein this film formation is preferably done by a spin coating method similarly to formation of the silicon-containing resist underlayer film. After the photoresist composition is spin-coated, prebake is done, preferably with the temperature of 80 to 180° C. and the time of 10 to 300 seconds. Thereafter, photo-exposure and organic solvent development are carried out successively to obtain a negative resist pattern. Further, it is preferable that post-exposure bake (PEB) be done after the photo-exposure.

Usable as the organic solvent developer includes a developer containing one or more components selected from 2-octanone, 2-nonanone, 2-heptanone, 3-heptanone, 4-heptanone, 2-hexanone, 3-hexanone, diisobutyl ketone, methyl cyclohexanone, acetophenone, methyl acetophenone, propyl acetate, butyl acetate, isobutyl acetate, amyl acetate, butenyl acetate, isoamyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate, wherein it is preferable to use a developer having the foregoing one, or two or more developer components contained therein with the total amount thereof being 50% or more by mass to remedy pattern fall and so forth.

In the patterning process of the present invention, when the silicon-containing resist underlayer film is etched, a gas mainly comprised of a fluorine-type gas such as a fluorocarbon gas is used. To minimize film loss of the photoresist film, it is preferable that etching rate of the silicon-containing resist underlayer film to the gas be fast.

In the multilayer resist method as mentioned above, if an organic underlay film is formed between the silicon-containing resist underlayer film and the body to be processed whereby using the organic underlayer film as an etching mask for the body to be processed, the organic underlayer film is preferably an organic film having an aromatic skeleton; on the other hand, if the organic underlayer film is a sacrifice film or the like, the silicon-containing organic underlayer film may be used provided that the silicon content therein is 15% or less by mass.

Organic underlayer films that are already in the public domain as the underlayer film for a three-layer resist process or a two-layer resist process which uses a silicon resist composition or that are already in public domain as the resist underlayer film material for a two-layer resist process and a three-layer resist process, the material being many resins including a novolak resin such as 4,4'-(9-fluorenylidene) bisphenol novolak resin (molecular weight of 11,000) described in the Japanese Patent Laid-Open publication No. 2005-128509, may be used. Alternatively, in order to increase heat resistance as compared with usual novolak resins, not only a resin having a polycyclic skeleton such as 6,6'-(9-fluorenylidene)-di(2-naphthol) novolak resin but also a polyimide resin may be selected (for example, Japanese Patent Laid-Open Publication No. 2004-153125).

The organic underlayer film can be formed on the body to be processed by using the composition solution thereof by a spin coating method or the like similarly to the photoresist composition. After the organic underlayer film is formed by a spin coating method or the like, it is preferable to carry out baking to evaporate an organic solvent. The baking is done preferably with the temperature of 80 to 300° C. and the time of 10 to 300 seconds.

Meanwhile, though not particularly restricted and depending on etching conditions, thickness of the organic underlayer film is preferably 5 nm or more, especially preferably 20 nm or more, and 50,000 nm or less; thickness of the silicon-containing resist underlayer film of the present invention is preferably 1 nm or more, and 500 nm or less, more preferably 300 nm or less, or still more preferably 200 nm or less; and thickness of the photoresist film is preferably in the range of 1 nm or more to 200 nm or less.

4. Patterning Process of the Present Invention by the Three-Layer Resist Method

The negative patterning process of the present invention according to the three-layer resist method as mentioned above is done as following (refer to FIG. 1). In this process, firstly the organic underlayer film 2 is formed on the body to be processed 1 by a spin coating method (FIG. 1(I-A)). It is desirable that the organic underlayer film 2 have high etching resistance because this acts as a mask during etching of the body to be processed 1; and it is also desirable that this undergo crosslinking by heat or an acid after it is formed by spin coating because mixing with the silicon-containing resist underlayer film of the upper layer is required not to occur.

Then, after the silicon-containing resist underlayer film 3 is formed thereonto by using the silicon-containing resist underlayer film composition of the present invention by spin coating (FIG. 1(I-B)), thereupon is formed the photoresist film 4 by spin coating (FIG. 1(I-C)). Meanwhile, the silicon-containing resist underlayer film 3 may be formed by using the composition giving the silicon-containing resist underlayer film 3 whose contact angle to pure water after exposure in the part thereof corresponding to the exposed area of the photoresist film 4 when it is exposed is in the range of 40 degrees or more to less than 70 degrees.

By using the mask 5, the photoresist film 4 is subjected to a usual pattern exposure using a light source P matching with the photoresist film 4, such as for example, a KrF excimer laser beam, an ArF excimer laser beam, an $F_2$ laser beam, and an EUV beam, to form a pattern preferably by any of a photolithography with the wavelength range of 10 nm or more to 300 nm or less, a direct drawing by an electron beam, and a nanoimprinting, or a combination of them (FIG. 1(I-D)); and thereafter, heat treatment thereof under the condition matching with respective photoresist films (FIG. 1(I-E)), development by an organic solvent developer (negative development), and then, as appropriate, rinsing are performed to obtain the negative resist pattern 4a (FIG. 1(I-F)).

Then, by using this negative resist pattern 4a as an etching mask, etching is carried out under the dry etching condition such that the etching rate of the silicon-containing resist underlayer film 3 may be significantly faster relative to the photoresist film, for example, by dry etching using a fluorine-based gas plasma. As a result, the negative silicon-containing resist underlayer film pattern 3a can be obtained without substantially receiving an influence of the pattern change due to side etching of the resist film (FIG. 1(I-G)).

Then, the organic underlayer film 2 is dry etched under the dry etching condition such that the etching rate of the organic underlayer film 2 may be significantly faster relative to the substrate having the negative silicon-containing resist underlayer film pattern 3a transferred with the negative resist pattern 4a obtained above, for example, by reactive dry etching with a gas plasma containing oxygen or by reactive dry etching with a gas plasma containing hydrogen and nitrogen. In this etching process, the negative organic underlayer film pattern 2a is obtained, while at the same time, the uppermost photoresist film is usually lost (FIG. 1(1-H)). Then, by using the negative organic underlayer film pattern 2a thus obtained as an etching mask, the body to be processed 1 is dry etched with high precision by using, for example, fluorine-based dry etching or chlorine-based dry etching thereby enabling to transfer the negative pattern 1a to the body to be processed 1 (FIG. 1(1-I)).

Meanwhile, in the process of the three-layer resist method mentioned above, alternatively an organic hard mask formed by a CVD method may be used in place of the organic underlayer film 2. In this case also, the body to be processed 1 can be processed by the procedure similar to the above procedure.

5. Positive Patterning Process 5-1. Positive Patterning Process 1

Further, the present invention provides a patterning process, wherein, an organic underlayer film is formed on a body to be processed by using an application-type organic underlayer film composition, a silicon-containing resist underlayer film is formed on the organic underlayer film by using the afore-mentioned silicon-containing resist underlayer film composition, a photoresist film is formed on the silicon-containing resist underlayer film by using a chemically amplifying type resist composition, after heat treatment the photoresist film is exposed to a high energy beam, a positive pattern is formed by dissolving an exposed area of the photoresist film by using an alkaline developer, the pattern is transferred to the silicon-containing resist underlayer film by dry etching by using the photoresist film formed with the positive pattern as a mask, the pattern is transferred by dry etching of the organic underlayer film by using the silicon-containing resist underlayer film transferred with the pattern as a mask, and then the pattern is transferred to the body to be processed by dry etching by using the organic underlayer film transferred with the pattern as a mask.

5-2. Positive Patterning Process 2

In addition, the present invention provides a patterning process, wherein, an organic hard mask mainly composed of carbon is formed on a body to be processed by a CVD method, a silicon-containing resist underlayer film is formed on the organic hard mask by using the afore-mentioned silicon-containing resist underlayer film composition, a photoresist film is formed on the silicon-containing resist underlayer film by using a chemically amplifying type resist composition, after heat treatment the photoresist film is exposed to a high energy beam, a positive pattern is formed by dissolving an exposed area of the photoresist film by using an alkaline developer, the pattern is transferred to the silicon-containing resist underlayer film by dry etching by using the photoresist film formed with the positive pattern as a mask, the pattern is transferred by dry etching of the organic hard mask by using the silicon-containing resist underlayer film transferred with the pattern as a mask, and then the pattern is transferred to the body to be processed by dry etching by using the organic hard mask transferred with the pattern as a mask.

If a pattern is formed by positive development by using the resist underlayer film of the present invention, a pattern formed in the photoresist can be formed on the substrate without causing transfer difference in size by optimizing a combination of the CVD film and the organic underlayer film as mentioned above.

Further, it is preferable that difference between contact angle to pure water of the silicon-containing resist underlayer film before formation of the photoresist film and contact angle to pure water of the silicon-containing resist underlayer film corresponding to the unexposed area of the photoresist film after photo-exposure be 10 degrees or less. If the difference between these contact angles is 10 degrees or less, difference of the contact angles between the unexposed area of the photoresist film and the part corresponding to this in the silicon-containing resist underlayer film can be made 10 degrees or less, whereby leading to good adhesion in the positive development; and as a result, a fine pattern can be formed.

In the positive patterning process of the present invention, the photoresist film is not particularly restricted provided that it is of a chemically amplifying type to give a positive pattern by development using an alkaline developer. As to the other matters, i.e., the film formation method, the body to be processed, the organic underlayer film, and the organic hard mask, those mentioned in the negative patterning process may be applied similarly.

In the positive patterning process, after formation of the photoresist film and then heat-treatment thereof, photo-exposure and then alkaline development by using an alkaline developer are carried out to obtain a positive resist pattern. In addition, after photo-exposure, it is preferable to carry out post-exposure bake (PEB).

As to the alkaline developer, tetramethyl ammonium hydroxide (TMAH) or the like may be used.

6. Patterning Process of the Present Invention by the Three-Layer Resist Method

The positive patterning process of the present invention according to the three-layer resist method is done as following (refer to FIG. 1). In this process, firstly the organic underlayer film 2 is formed on the body to be processed 1 by a spin coating method (FIG. 1(II-A)). It is desirable that the organic underlayer film 2 have high etching resistance because this acts as a mask during etching of the body to be processed 1; and it is also desirable that this undergo crosslinking by heat or an acid after it is formed by spin coating because mixing with the silicon-containing resist underlayer film of the upper layer is required not to occur.

Then, after the silicon-containing resist underlayer film 3 is formed thereupon by using the silicon-containing resist underlayer film composition of the present invention by spin coating (FIG. 1(II-B)), thereupon is formed the photoresist film 4 by spin coating (FIG. 1(II-C)). Meanwhile, the silicon-containing resist underlayer film 3 may be formed by using the composition giving the silicon-containing resist underlayer film 3 whose contact angle to pure water after exposure in the part thereof corresponding to the exposed area of the photoresist film 4 when it is exposed is in the range of 40 degrees or more to less than 70 degrees.

By using the mask 5, the photoresist film 4 is subjected to a usual pattern exposure using a light source P matching with the photoresist film 4, such as for example, a KrF excimer laser beam, an ArF excimer laser beam, an $F_2$ laser beam, and an EUV beam, to form a pattern preferably by any of a photolithography method with the wavelength ranging from 10 nm or more to 300 nm or less, a direct drawing method by an electron beam, and a nanoimprinting method, or a combination of them (FIG. 1(II-D)); and thereafter, heat treatment thereof under the condition matching with respective photoresist films (FIG. 1(II-E)), development by an alkaline developer, and then, as appropriate, rinsing are performed to obtain the positive resist pattern 4b (FIG. 1(II-F)).

Then, by using this resist pattern 4b as an etching mask, etching is carried out under the dry etching condition such that the etching rate of the silicon-containing resist underlayer film 3 may be significantly faster relative to the photoresist film, for example, by dry etching using a fluorine-based gas plasma. As a result, the positive silicon-containing resist underlayer film pattern 3b can be obtained without substantially receiving an influence of the pattern change due to side etching of the resist film (FIG. 1(II-G)).

Then, the organic underlayer film 2 is etched under the dry etching condition such that the etching rate of the organic underlayer film 2 may be significantly faster relative to the substrate having the positive silicon-containing resist underlayer film pattern 3b transferred with the positive resist pattern obtained above, for example, by reactive dry etching with a gas plasma containing oxygen or by reactive dry etching with a gas plasma containing hydrogen and nitrogen. In this etching process, the positive organic underlayer film pattern 2b is obtained, while at the same time, the uppermost photoresist film is usually lost (FIG. 1(II-H)). Then, by using the positive organic underlayer film pattern 2b thereby obtained as an etching mask, the body to be processed 1 is dry etched with high precision by using, for example, fluorine-based dry etching or chlorine-based dry etching thereby enabling to transfer the positive pattern 1b to the body to be processed 1 (FIG. 1(II-I)).

Meanwhile, in the process of the three-layer resist method mentioned above, alternatively an organic hard mask formed by a CVD method may be used in place of the organic underlayer film 2. In this case also, the body to be processed 1 can be processed by the procedure similar to the above procedure.

EXAMPLES

Hereinafter, the present invention will be explained specifically by showing Synthesis Examples, Examples, and Comparative Examples; but the present invention is not restricted by these descriptions. Meanwhile, in the following descriptions, "%" means "% by mass" and molecular weights were measured by GPC.

A. Synthesis of Surface Modifier Component

Synthesis Example 1-1

Into a mixture of 200 g of methanol, 0.1 g of methanesulfonic acid, and 60 g of deionized water was added a mixture of 27.2 g of Monomer 101, 22.8 g of Monomer 102, and 44.8 g of Monomer 120; and then, they were kept at 40° C. for 12 hours to carry out hydrolytic condensation. After the reaction, 200 g of propylene glycol ethyl ether (PGEE) was added thereinto; and then, the by-produced alcohol was distilled out under reduced pressure. Then, 1000 mL of ethyl acetate and 300 g of PGEE were added thereinto to separate a water layer. To the remained organic layer was added 100 mL of ion-exchanged water; and then, the resulting mixture was stirred, settled, and separated into the layers. This operation was repeated for three times. The remained organic layer was concentrated under reduced pressure to obtain 280 g of PGEE solution containing the silicon-containing compound 1-1 (compound concentration of 20%). The polystyrene-equivalent molecular weight of this compound was measured to be Mw=2,100.

Synthesis Examples 1-2 to 1-4, Synthesis Examples 1-6 to 1-10, Synthesis Examples 1-13 to 1-20, and Synthesis Examples 1-25 to 1-31 were carried out by using the monomers shown in Table 1 under the conditions similar to those in Synthesis Examples 1-1 to obtain each of the intended products.

Synthesis Example 1-5

Into a mixture of 400 g of ethanol, 5 g of 25% tetramethyl ammonium hydroxide, and 200 g of deionized water was added a mixture of 13.6 g of Monomer 101, 38.1 g of Monomer 102, and 40.6 g of Monomer 122; and then, they were kept at 40° C. for 4 hours to carry out hydrolytic condensation. After the reaction, 2 g of acetic acid was added thereinto for neutralization, and then, the by-produced alcohol was distilled out under reduced pressure. Then, 1200 mL of ethyl acetate and 400 g of PGEE were added thereinto to separate a water layer. To the remained organic layer was added 100 mL of ion-exchanged water; and then, the resulting mixture was stirred, settled, and separated into the layers. This operation was repeated for three times. The remained organic layer was concentrated under reduced pressure to obtain 260 g of PGEE solution containing the silicon-containing compound 1-5 (compound concentration of 20%). The polystyrene-equivalent molecular weight of this compound was measured to be Mw=2,000.

Synthesis Example 1-11, Synthesis Example 1-12, and Synthesis Examples 1-21 to 1-24 were carried out by using the monomers shown in Table 1 under the conditions similar to those in Synthesis Example 1-5 to obtain each of the intended products.

TABLE 2

| Structure | Name |
|---|---|
| PhSi(OCH$_3$)$_3$ | Monomer 100 |
| CH$_3$Si(OCH$_3$)$_3$ | Monomer 101 |
| Si(OCH$_3$)$_4$ | Monomer 102 |
| (CH$_3$O)$_3$Si—C$_6$H$_4$—CH$_3$ | Monomer 104 |
| (CH$_3$O)$_3$Si—C$_6$H$_4$—OCH$_3$ | Monomer 105 |
| B(OC$_3$H$_7$)$_3$ | Monomer 110 |
| Ti(OC$_4$H$_9$)$_4$ | Monomer 111 |
| Ge(OC$_4$H$_9$)$_4$ | Monomer 112 |
| P$_2$O$_5$ | Monomer 113 |
| Al[CH$_3$COCH═C(O—)CH$_3$]$_3$ | Monomer 114 |
| (CH$_3$O)$_3$Si—CH$_2$CH$_2$—C$_6$H$_4$—O—C(CH$_3$)$_3$ | Monomer 120 |
| (CH$_3$O)$_3$Si—CH$_2$CH$_2$—C$_6$H$_3$(F)—O—C(CH$_3$)$_3$ | Monomer 121 |

TABLE 1

| Synthesis Example | Raw materials for reaction | Mw |
|---|---|---|
| 1-1 | Monomer 101: 27.2 g, Monomer 102: 22.8 g, Monomer 120: 44.8 g | 2100 |
| 1-2 | Monomer 101: 13.6 g, Monomer 102: 15.2 g, Monomer 120: 89.5 g | 2300 |
| 1-3 | Monomer 101: 13.6 g, Monomer 102: 38.1 g, Monomer 121: 49.6 g | 2000 |
| 1-4 | Monomer 101: 13.6 g, Monomer 102: 15.2 g, Monomer 121: 99.1 g | 2300 |
| 1-5 | Monomer 101: 13.6 g, Monomer 102: 38.1 g, Monomer 122: 40.6 g | 2000 |
| 1-6 | Monomer 101: 13.6 g, Monomer 102: 15.2 g, Monomer 122: 81.1 g | 3700 |
| 1-7 | Monomer 101: 27.2 g, Monomer 102: 22.8 g, Monomer 123: 46.9 g | 1500 |
| 1-8 | Monomer 101: 13.6 g, Monomer 102: 15.2 g, Monomer 123: 93.7 g | 2300 |
| 1-9 | Monomer 101: 20.4 g, Monomer 102: 30.4 g, Monomer 124: 45.1 g | 1600 |
| 1-10 | Monomer 101: 27.2 g, Monomer 124: 90.1 g | 1900 |
| 1-11 | Monomer 101: 27.2 g, Monomer 102: 22.8 g, Monomer 125: 47.2 g | 3200 |
| 1-12 | Monomer 101: 27.2 g, Monomer 125: 94.3 g | 3300 |
| 1-13 | Monomer 101: 13.6 g, Monomer 102: 38.1 g, Monomer 126: 49 g | 2200 |
| 1-14 | Monomer 102: 30.4 g, Monomer 126: 97.9 g | 1500 |
| 1-15 | Monomer 101: 13.6 g, Monomer 102: 38.1 g, Monomer 127: 40.6 g | 1800 |
| 1-16 | Monomer 102: 30.4 g, Monomer 127: 81.1 g | 1800 |
| 1-17 | Monomer 101: 13.6 g, Monomer 102: 38.1 g, Monomer 128: 53.5 g | 1900 |
| 1-18 | Monomer 102: 30.4 g, Monomer 128: 106.9 g | 1700 |
| 1-19 | Monomer 101: 13.6 g, Monomer 102: 38.1 g, Monomer 129: 51.4 g | 2100 |
| 1-20 | Monomer 101: 27.2 g, Monomer 129: 102.8 g | 1900 |
| 1-21 | Monomer 101: 34.1 g, Monomer 102: 15.2 g, Monomer 130: 39.7 g | 3300 |
| 1-22 | Monomer 101: 27.2 g, Monomer 102: 22.8 g, Monomer 131: 47.8 g | 2200 |
| 1-23 | Monomer 101: 13.6 g, Monomer 102: 38.1 g, Monomer 132: 41.8 g | 2300 |
| 1-24 | Monomer 101: 34.1 g, Monomer 102: 15.2 g, Monomer 133: 47.5 g | 2100 |
| 1-25 | Monomer 101: 27.2 g, Monomer 133: 94.9 g | 1800 |
| 1-26 | Monomer 101: 47.7 g, Monomer 134: 25.4 g, Monomer 120: 13.2 g | 2000 |
| 1-27 | Monomer 101: 54.5 g, Monomer 135: 26.6 g | 1600 |
| 1-28 | Monomer 101: 40.9 g, Monomer 120: 44.8 g, Monomer 134: 12.7 g | 2100 |
| 1-29 | Monomer 101: 40.9 g, Monomer 122: 40.6 g, Monomer 135: 13.3 g | 1600 |
| 1-30 | Monomer 101: 40.9 g, Monomer 126: 49.0 g, Monomer 134: 12.7 g, Monomer 135: 13.3 g | 1700 |
| 1-31 | Monomer 100: 19.8 g, Monomer 101: 27.2 g, Monomer 102: 30.4 g | 1700 |

TABLE 2-continued

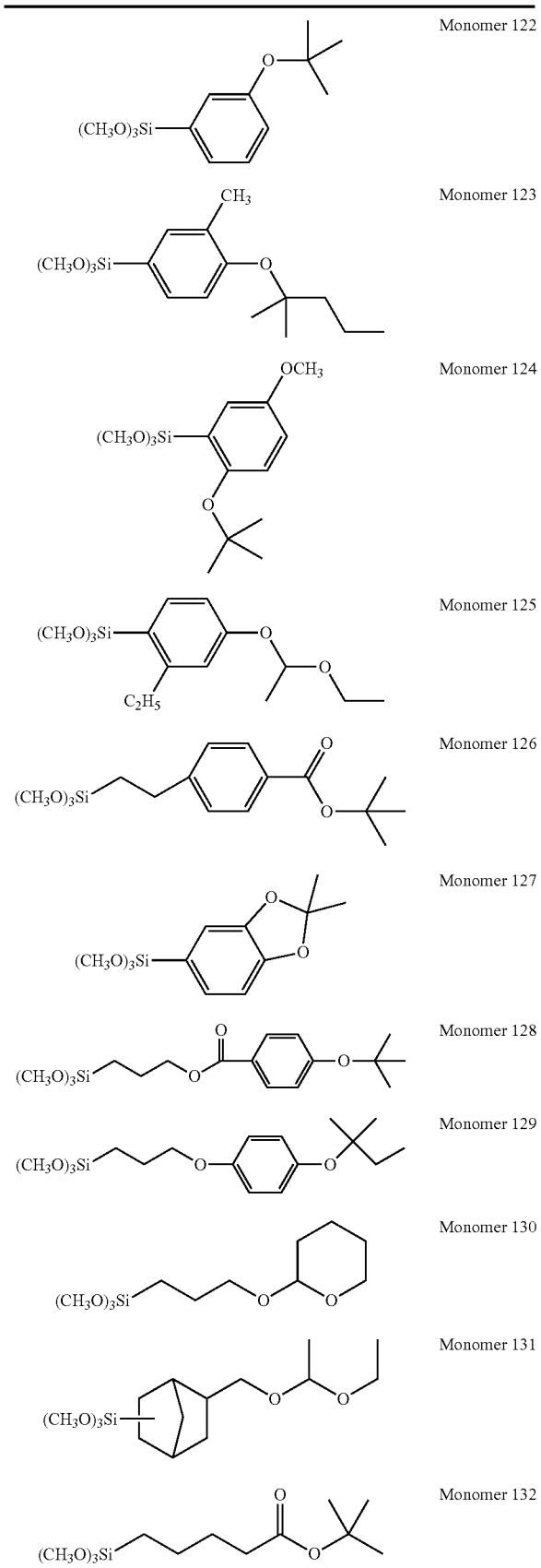

Monomer 122
Monomer 123
Monomer 124
Monomer 125
Monomer 126
Monomer 127
Monomer 128
Monomer 129
Monomer 130
Monomer 131
Monomer 132

TABLE 2-continued

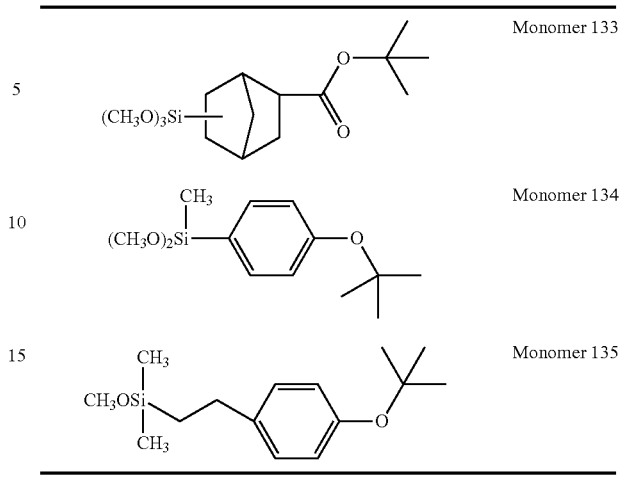

Monomer 133
Monomer 134
Monomer 135

B. Synthesis of Polymer Component

Synthesis Example 2-1

Into a mixture of 120 g of methanol, 0.1 g of 70% nitric acid, and 60 g of deionized water was added a mixture of 5.0 g of Monomer 100, 3.4 g of Monomer 101, and 68.5 g of Monomer 102; and then, they were kept at 40° C. for 12 hours to carry out hydrolytic condensation. After the reaction, 300 g of PGEE was added thereinto; and then, the by-produced alcohol and excess water were distilled out under reduced pressure to obtain 320 g of PGEE solution containing the polysiloxane compound 2-1 (polymer concentration of 10%). The polystyrene-equivalent molecular weight of this compound was measured to be Mw=2,300.

Synthesis Examples 2-2 to 2-8 were carried out by using the monomers shown in Table 3 under the conditions similar to those in Synthesis Examples 2-1 to obtain each of the intended products.

TABLE 3

| Synthesis Example | Raw materials for reaction | Mw |
|---|---|---|
| 2-1 | Monomer 100: 5.0 g, Monomer 101: 3.4 g, Monomer 102: 68.5 g | 2300 |
| 2-2 | Monomer 100: 5.0 g, Monomer 101: 3.4 g, Monomer 102: 60.9 g, Monomer 110: 9.4 g | 3800 |
| 2-3 | Monomer 100: 5.0 g, Monomer 101: 3.4 g, Monomer 102: 60.9 g, Monomer 111: 17.0 g | 3900 |
| 2-4 | Monomer 100: 5.0 g, Monomer 101: 3.4 g, Monomer 102: 60.9 g, Monomer 112: 18.3 g | 3900 |
| 2-5 | Monomer 100: 5.0 g, Monomer 101: 3.4 g, Monomer 102: 60.9 g, Monomer 113: 14.2 g | 3900 |
| 2-6 | Monomer 104: 5.3 g, Monomer 101: 3.4 g, Monomer 102: 60.9 g, Monomer 114: 16.2 g | 3600 |
| 2-7 | Monomer 105: 5.7 g, Monomer 101: 17.0 g, Monomer 102: 53.3 g | 3200 |
| 2-8 | Monomer 100: 5.0 g, Monomer 101: 23.8 g, Monomer 102: 45.7 g | 2200 |

Examples and Comparative Examples

Each of the silicon-containing surface modifiers (1-1) to (1-31) prepared by the above Synthesis Examples, each of the polysiloxane compounds (2-1) to (2-8) as the polymer component, an acid, a thermal crosslinking accelerator, a solvent, and an additive were mixed by the ratio shown in Table 4-1 to Table 4-3; and then, the resulting mixture was filtrated by a 0.1-μm filter made of a fluorinated resin to obtain each of the silicon-containing underlayer film composition solutions Sol. 1 to Sol. 52.

TABLE 4-1

| No. | Silicon-containing surface modifier (Parts by mass) | Poly-siloxane (Parts by mass) | Thermal cross-linking accelerator (Parts by mass) | Photo-sensitive acid generator (Parts by mass) | Acid (Parts by mass) | Solvent (Parts by mass) | Water (Parts by mass) |
|---|---|---|---|---|---|---|---|
| Sol. 1 | 1-1 (0.1) | 2-1 (3.9) | TPSOH (0.04) | None | Maleic acid (0.04) | PGEE (150) | Water (15) |
| Sol. 2 | 1-1 (0.1) | 2-1 (3.9) | TPSHCO$_3$ (0.04) | None | Oxalic acid (0.04) | PGEE (150) | Water (15) |
| Sol. 3 | 1-1 (0.1) | 2-1 (3.9) | TPSOx (0.04) | None | Maleic acid (0.04) | PGEE (150) | Water (15) |
| Sol. 4 | 1-1 (0.1) | 2-1 (3.9) | TPSTFA (0.04) | None | Maleic acid (0.04) | PGEE (150) | Water (15) |
| Sol. 5 | 1-1 (0.1) | 2-1 (3.9) | TPSOCOPh (0.04) | None | Oxalic acid (0.04) | PGEE (150) | Water (15) |
| Sol. 6 | 1-1 (0.1) | 2-1 (3.9) | TPSH$_2$PO$_4$ (0.04) | None | Oxalic acid (0.04) | PGEE (150) | Water (15) |
| Sol. 7 | 1-1 (0.1) | 2-1 (3.9) | QMAMA (0.04) | None | Maleic acid (0.04) | PGEE (150) | Water (15) |
| Sol. 8 | 1-1 (0.1) | 2-1 (3.9) | QBANO$_3$ (0.04) | None | Maleic acid (0.04) | PGEE (150) | Water (15) |
| Sol. 9 | 1-1 (0.1) | 2-1 (3.9) | QMATFA (0.04) | TPSNf (0.04) | Maleic acid (0.04) | PGEE (150) | Water (15) |
| Sol. 10 | 1-1 (0.1) | 2-1 (3.9) | Ph$_2$ICl (0.04) | None | Maleic acid (0.04) | PGEE (150) | Water (15) |
| Sol. 11 | 1-1 (0.1) | 2-1 (3.9) | TPSMA (0.04) | None | Maleic acid (0.04) | PGEE (150) | Water (15) |
| Sol. 12 | 1-2 (0.1) | 2-1 (3.9) | TPSMA (0.04) | None | Maleic acid (0.04) | PGEE (150) | Water (15) |
| Sol. 13 | 1-3 (0.1) | 2-1 (3.9) | TPSMA (0.04) | None | Maleic acid (0.04) | PGEE (150) | Water (15) |
| Sol. 14 | 1-4 (0.1) | 2-1 (3.9) | TPSMA (0.04) | None | Maleic acid (0.04) | PGEE (150) | Water (15) |
| Sol. 15 | 1-5 (0.1) | 2-1 (3.9) | TPSMA (0.04) | None | None | PGEE (165) | None |
| Sol. 16 | 1-6 (0.1) | 2-1 (3.9) | TPSMA (0.04) | None | Oxalic acid (0.04) | PGEE (150) | Water (15) |
| Sol. 17 | 1-7 (0.1) | 2-1 (3.9) | TPSMA (0.04) | None | Maleic acid (0.04) | PGEE (150) | Water (15) |
| Sol. 18 | 1-8 (0.1) | 2-1 (3.9) | TPSMA (0.04) | None | Maleic acid (0.04) | PGEE (150) | Water (15) |
| Sol. 19 | 1-9 (0.1) | 2-1 (3.9) | TPSMA (0.04) | None | Maleic acid (0.04) | PGEE (150) | Water (15) |
| Sol. 20 | 1-10 (0.1) | 2-1 (3.9) | TPSMA (0.04) | TPSNf (0.04) | Maleic acid (0.04) | PGEE (150) | Water (15) |

TABLE 4-2

| No. | Silicon-containing surface modifier (Parts by mass) | Poly-siloxane (Parts by mass) | Thermal cross-linking accelerator (Parts by mass) | Photo-sensitive acid generator (Parts by mass) | Acid (Parts by mass) | Solvent (Parts by mass) | Water (Parts by mass) |
|---|---|---|---|---|---|---|---|
| Sol. 21 | 1-11 (0.1) | 2-1 (3.9) | TPSMA (0.04) | None | None | PGEE (165) | None |
| Sol. 22 | 1-12 (0.1) | 2-1 (3.9) | TPSMA (0.04) | None | None | PGEE (165) | None |
| Sol. 23 | 1-13 (0.1) | 2-1 (3.9) | TPSMA (0.04) | None | Maleic acid (0.04) | PGEE (150) | Water (15) |
| Sol. 24 | 1-14 (0.1) | 2-1 (3.9) | TPSMA (0.04) | None | Maleic acid (0.04) | PGEE (150) | Water (15) |
| Sol. 25 | 1-15 (0.1) | 2-1 (3.9) | TPSMA (0.04) | None | Maleic acid (0.04) | PGEE (150) | Water (15) |
| Sol. 26 | 1-16 (0.1) | 2-1 (3.9) | TPSMA (0.04) | None | Maleic acid (0.04) | PGEE (150) | Water (15) |
| Sol. 27 | 1-17 (0.1) | 2-1 (3.9) | TPSMA (0.04) | None | Maleic acid (0.04) | PGEE (150) | Water (15) |
| Sol. 28 | 1-18 (0.1) | 2-1 (3.9) | TPSMA (0.04) | None | Maleic acid (0.04) | PGEE (150) | Water (15) |
| Sol. 29 | 1-19 (0.1) | 2-1 (3.9) | TPSMA (0.04) | None | Maleic acid (0.04) | PGEE (150) | Water (15) |
| Sol. 30 | 1-20 (0.1) | 2-1 (3.9) | TPSMA (0.04) | TPSNf (0.04) | Maleic acid (0.04) | PGEE (150) | Water (15) |

TABLE 4-2-continued

| No. | Silicon-containing surface modifier (Parts by mass) | Poly-siloxane (Parts by mass) | Thermal cross-linking accelerator (Parts by mass) | Photo-sensitive acid generator (Parts by mass) | Acid (Parts by mass) | Solvent (Parts by mass) | Water (Parts by mass) |
|---|---|---|---|---|---|---|---|
| Sol. 31 | 1-21 (0.1) | 2-1 (3.9) | TPSMA (0.04) | None | None | PGEE (165) | None |
| Sol. 32 | 1-22 (0.1) | 2-1 (3.9) | TPSMA (0.04) | None | None | PGEE (165) | None |
| Sol. 33 | 1-23 (0.1) | 2-1 (3.9) | TPSMA (0.04) | None | Maleic acid (0.04) | PGEE (135) GBL (15) | Water (15) |
| Sol. 34 | 1-24 (0.1) | 2-1 (3.9) | TPSMA (0.04) | None | Maleic acid (0.04) | PGEE (150) | Water (15) |
| Sol. 35 | 1-25 (0.1) | 2-1 (3.9) | TPSMA (0.04) | None | Maleic acid (0.04) | PGEE (150) | Water (15) |
| Sol. 36 | 1-26 (0.1) | 2-1 (3.9) | TPSMA (0.04) | None | Maleic acid (0.04) | PGEE (135) GBL (15) | Water (15) |
| Sol. 37 | 1-27 (0.1) | 2-1 (3.9) | TPSMA (0.04) | None | Maleic acid (0.04) | PGEE (150) | Water (15) |
| Sol. 38 | 1-28 (0.1) | 2-1 (3.9) | TPSMA (0.04) | None | Maleic acid (0.04} | PGEE (150) | Water (15) |

TABLE 4-3

| Ho. | Silicon-containing surface modifier (Parts by mass) | Poly-siloxane (Parts by mass) | Thermal cross-linking accelerator (Parts by mass) | Photo-sensitive acid generator (Parts by mass) | Acid (Parts by mass) | Solvent (Parts by mass) | Water (Parts by mass) |
|---|---|---|---|---|---|---|---|
| Sol. 39 | 1-29 (0.1) | 2-1 (3.9) | TPSMA (0.04) | None | Maleic acid (0.04) | PGEE (135) GBL (15) | Water (15) |
| Sol. 40 | 1-30 (0.1) | 2-1 (3.9) | TPSMA (0.04) | None | Maleic acid (0.04) | PGEE (150) | Water (15) |
| Sol. 41 | 1-5 (0.05) 1-13 (0.05) | 2-1 (3.9) | TPSMA (0.04) | None | Maleic acid (0.04) | PGEE (150) | Water (15) |
| Sol. 42 | 1-5 (0.05) 1-21 (0.05) | 2-1 (3.9) | TPSMA (0.04) | None | None | PGEE (165) | None |
| Sol. 43 | 1-5 (0.05) 1-24 (0.05) | 2-1 (3.9) | TPSMA (0.04) | None | Maleic acid (0.04) | PGEE (150) | Water (15) |
| Sol. 44 | 1-22 (0.05) 1-23 (0.05) | 2-1 (3.9) | TPSMA (0.04) | None | None | PGEE (165) | None |
| Sol. 45 | 1-13 (0.1) | 2-2 (3.9) | TPSMA (0.04) | None | Maleic acid (0.04) | PGEE (135) GBL (15) | Water (15) |
| Sol. 46 | 1-13 (0.1) | 2-3 (3.9) | TPSMA (0.04) | None | Maleic acid (0.04) | PGEE (150) | Water (15) |
| Sol. 47 | 1-13 (0.1) | 2-4 (3.9) | TPSMA (0.04) | None | Maleic acid (0.04) | PGEE (135) GBL (15) | Water (15) |
| Sol. 48 | 1-13 (0.1) | 2-5 (3.9) | TPSMA (0.04) | None | Maleic acid (0.04) | PGEE (150) | Water (15) |
| Sol. 49 | 1-13 (0.1) | 2-6 (3.9) | TPSMA (0.04) | None | Maleic acid (0.04) | PGEE (150) | Water (15) |
| Sol. 50 | 1-13 (0.1) | 2-7 (3.9) | TPSMA (0.04) | None | Maleic acid (0.04) | PGEE (150) | Water (15) |
| Sol. 51 | 1-1 (0.1) | 2-8 (3.9) | TPSMA (0.04) | None | Maleic acid (0.04) | PGEE (150) | Water (15) |

TABLE 4-3-continued

| No. | Silicon-containing surface modifier (Parts by mass) | Polysiloxane (Parts by mass) | Thermal cross-linking accelerator (Parts by mass) | Photosensitive acid generator (Parts by mass) | Acid (Parts by mass) | Solvent (Parts by mass) | Water (Parts by mass) |
|---|---|---|---|---|---|---|---|
| Sol. 52 | 1-31 (0.1) | 2-1 (3.9) | TPSMA (0.04) | None | Maleic acid (0.04) | PGEE (150) | Water (15) |

TPSOH: Triphenylsulfonium hydroxide
TPSHCO$_3$: Mono(triphenylsulfonium)carbonate
TPSOx: Mono(triphenylsulfonium)oxalate
TPSTFA: Triphenylsulfonium trifluoroacetate
TPSOCOPh: Triphenylsulfonium benzoate
TPSH$_2$PO$_4$: Mono(triphenylsulfonium)phosphate
TPSMA: Mono(triphenylsulfonium)maleate
TPSNf: Triphenylsulfonium nonafluorobutanesulfonate
QMAMA: Mono(tetramethylammonium)maleate
QMATFA: Tetramethylammonium trifluoroacetate
QBANO$_3$: Tetrabutylammonium nitrate
Ph$_2$ICl: Diphenyliodonium chloride
PGEE: Propylene glycol ethyl ether
GBL: γ-Butyrolactone C. Measurement of Contact Angle C-1. Contact Angle Sample of the Underlayer Film Only Each of the silicon-containing resist underlayer film compositions Sol. 1 to Sol. 52 was applied on a silicon wafer and then heated at 240° C. for 60 seconds to form the respective silicon-containing Film 1 to Film 52 having film thickness of 35 nm; and then, contact angle thereof to pure water (CA1) was measured (Table 5).

C-2. Contact Angle Sample of the Unexposed Area of the Underlayer Film Formed by Coating a Resist for Positive Development on the Underlayer Film and Removing Thereof Thereafter Each of the silicon-containing resist underlayer film compositions Sol. 1 to Sol. 52 was applied on a silicon wafer and then heated at 240° C. for 60 seconds to form the respective silicon-containing Film 1 to Film 52 having film thickness of 35 nm. Further on this film was applied the ArF resist solution (PR-1) shown in Table 10; and then, it was baked at 100° C. for 60 seconds to form the photoresist film having film thickness of 100 nm. Then, entirety of this resist film was removed by rinsing with propylene glycol monomethyl ether (PGME) to obtain the film equivalent to the unexposed area of the silicon-containing film. Then, contact angle of it to pure water (CA2) was measured (Table 6).

C-3. Contact Angle Sample of the Unexposed Area of the Underlayer Film Formed by Coating the Underlayer Film by a Resist for Negative Development and Removing Thereof Thereafter Each of the silicon-containing resist underlayer film compositions Sol. 1 to Sol. 52 was applied on a silicon wafer and then heated at 240° C. for 60 seconds to form the respective silicon-containing Film 1 to Film 52 having film thickness of 35 nm. On this film was applied the ArF resist solution for negative development (PR-3) shown in Table 13; and then, it was baked at 100° C. for 60 seconds to form the photoresist film having film thickness of 100 nm. Further on this photoresist film was applied an immersion top coat (TC-1) shown in Table 11; and then, it was baked at 90° C. for 60 seconds to form the top coat having film thickness of 50 nm. Then, entirety of the immersion top coat and the upper layer photoresist film was removed by rinsing with PGME to obtain the film equivalent to the unexposed area of the silicon-containing film. Then, contact angle of it to pure water (CA3) was measured (Table 7).

C-4. Contact Angle Sample of the Exposed Area of the Underlayer Film Formed by Coating the Underlayer Film by a Resist for Negative Development and Removing Thereof After Photo-Exposure Each of the silicon-containing resist underlayer film compositions Sol. 1 to Sol. 52 was applied on a silicon wafer and then heated at 240° C. for 60 seconds to form respective silicon-containing Film 1 to Film 52 having film thickness of 35 nm. On this film was applied the ArF resist solution for negative development (PR-3) shown in Table 10; and then, it was baked at 100° C. for 60 seconds to form the photoresist film having film thickness of 100 nm. Further on this photoresist film was applied an immersion top coat (TC-1) shown in Table 11; and then, it was baked at 90° C. for 60 seconds to form the top coat having film thickness of 50 nm. Then, after entirety thereof was exposed by using ArF immersion exposure instrument NSR-S610C (manufactured by Nikon Corp.) and then baked at 100° C. for 60 seconds (PEB), a butyl acetate development solution was discharged for 3 seconds from a developer nozzle with rotation speed of 30 rpm; and thereafter, rotation was stopped, and then puddle development was done for 27 seconds. After rinsing thereof by diisoamyl ether, it was spin-dried and then baked at 100° C. for 20 seconds to evaporate the rinse solvent. Entirety of the remaining resist film was removed by rinsing with PGME to obtain the exposed area of the silicon-containing film. Then, contact angle of it to pure water (CA4) was measured (Table 8).

C-5. Contact Angle Sample of the Exposed Area of the Resist for Negative Development After the ArF resist solution for negative development (PR-3) shown in Table 13 was applied on a silicon wafer, it was baked at 100° C. for 60 seconds to form the photoresist film having film thickness of 100 nm; and then, contact angle of it to pure water was measured. Then, after entirety of the same resist film was exposed by using ArF exposure instrument NSR-S610C (manufactured by Nikon Corp.) and then baked at 100° C. for 60 seconds (PEB), it was rinsed by diisoamyl ether, spin-dried, and then baked at 100° C. for 20 seconds to evaporate the rinse solvent to obtain the ArF resist film corresponding to the pattern part having the acid-labile group eliminated at the time of negative development. Then, contact angle of it to pure water was measured (Table 9).

TABLE 5

| No. | Contact angle |
|---|---|
| Film 1 | 73 degrees |
| Film 2 | 69 degrees |
| Film 3 | 70 degrees |
| Film 4 | 71 degrees |
| Film 5 | 72 degrees |

TABLE 5-continued

| No. | Contact angle |
| --- | --- |
| Film 6 | 70 degrees |
| Film 7 | 69 degrees |
| Film 8 | 70 degrees |
| Film 9 | 73 degrees |
| Film 10 | 69 degrees |
| Film 11 | 73 degrees |
| Film 12 | 73 degrees |
| Film 13 | 73 degrees |
| Film 14 | 73 degrees |
| Film 15 | 74 degrees |
| Film 16 | 70 degrees |
| Film 17 | 70 degrees |
| Film 18 | 73 degrees |
| Film 19 | 73 degrees |
| Film 20 | 72 degrees |
| Film 21 | 69 degrees |
| Film 22 | 73 degrees |
| Film 23 | 70 degrees |
| Film 24 | 70 degrees |
| Film 25 | 70 degrees |
| Film 26 | 72 degrees |
| Film 27 | 72 degrees |
| Film 28 | 71 degrees |
| Film 29 | 71 degrees |
| Film 30 | 73 degrees |
| Film 31 | 71 degrees |
| Film 32 | 72 degrees |
| Film 33 | 72 degrees |
| Film 34 | 73 degrees |
| Film 35 | 73 degrees |
| Film 36 | 72 degrees |
| Film 37 | 73 degrees |
| Film 38 | 71 degrees |
| Film 39 | 72 degrees |
| Film 40 | 73 degrees |
| Film 41 | 71 degrees |
| Film 42 | 72 degrees |
| Film 43 | 71 degrees |
| Film 44 | 71 degrees |
| Film 45 | 73 degrees |
| Film 46 | 73 degrees |
| Film 47 | 70 degrees |
| Film 48 | 71 degrees |
| Film 49 | 73 degrees |
| Film 50 | 71 degrees |
| Film 51 | 73 degrees |
| Film 52 | 70 degrees |

TABLE 6

| No. | Contact angle |
| --- | --- |
| Film 1 | 69 degrees |
| Film 2 | 63 degrees |
| Film 3 | 61 degrees |
| Film 4 | 62 degrees |
| Film 5 | 62 degrees |
| Film 6 | 67 degrees |
| Film 7 | 65 degrees |
| Film 8 | 65 degrees |
| Film 9 | 69 degrees |
| Film 10 | 60 degrees |
| Film 11 | 68 degrees |
| Film 12 | 65 degrees |
| Film 13 | 71 degrees |
| Film 14 | 63 degrees |
| Film 15 | 70 degrees |
| Film 16 | 66 degrees |
| Film 17 | 67 degrees |
| Film 18 | 67 degrees |
| Film 19 | 66 degrees |
| Film 20 | 63 degrees |
| Film 21 | 63 degrees |
| Film 22 | 63 degrees |
| Film 23 | 61 degrees |

TABLE 6-continued

| No. | Contact angle |
| --- | --- |
| Film 24 | 63 degrees |
| Film 25 | 65 degrees |
| Film 26 | 64 degrees |
| Film 27 | 68 degrees |
| Film 28 | 65 degrees |
| Film 29 | 66 degrees |
| Film 30 | 70 degrees |
| Film 31 | 67 degrees |
| Film 32 | 67 degrees |
| Film 33 | 67 degrees |
| Film 34 | 63 degrees |
| Film 35 | 69 degrees |
| Film 36 | 68 degrees |
| Film 37 | 70 degrees |
| Film 38 | 69 degrees |
| Film 39 | 68 degrees |
| Film 40 | 67 degrees |
| Film 41 | 68 degrees |
| Film 42 | 63 degrees |
| Film 43 | 68 degrees |
| Film 44 | 62 degrees |
| Film 45 | 70 degrees |
| Film 46 | 63 degrees |
| Film 47 | 63 degrees |
| Film 48 | 68 degrees |
| Film 49 | 66 degrees |
| Film 50 | 62 degrees |
| Film 51 | 63 degrees |
| Film 52 | 61 degrees |

TABLE 7

| No. | Contact angle |
| --- | --- |
| Film 1 | 70 degrees |
| Film 2 | 62 degrees |
| Film 3 | 66 degrees |
| Film 4 | 68 degrees |
| Film 5 | 63 degrees |
| Film 6 | 63 degrees |
| Film 7 | 66 degrees |
| Film 8 | 67 degrees |
| Film 9 | 68 degrees |
| Film 10 | 63 degrees |
| Film 11 | 69 degrees |
| Film 12 | 68 degrees |
| Film 13 | 63 degrees |
| Film 14 | 69 degrees |
| Film 15 | 66 degrees |
| Film 16 | 65 degrees |
| Film 17 | 67 degrees |
| Film 18 | 68 degrees |
| Film 19 | 70 degrees |
| Film 20 | 69 degrees |
| Film 21 | 63 degrees |
| Film 22 | 69 degrees |
| Film 23 | 61 degrees |
| Film 24 | 63 degrees |
| Film 25 | 65 degrees |
| Film 26 | 64 degrees |
| Film 27 | 69 degrees |
| Film 28 | 64 degrees |
| Film 29 | 66 degrees |
| Film 30 | 69 degrees |
| Film 31 | 62 degrees |
| Film 32 | 69 degrees |
| Film 33 | 66 degrees |
| Film 34 | 65 degrees |
| Film 35 | 71 degrees |
| Film 36 | 68 degrees |
| Film 37 | 67 degrees |
| Film 38 | 62 degrees |
| Film 39 | 68 degrees |
| Film 40 | 67 degrees |
| Film 41 | 67 degrees |

TABLE 7-continued

| No. | Contact angle |
| --- | --- |
| Film 42 | 62 degrees |
| Film 43 | 68 degrees |
| Film 44 | 63 degrees |
| Film 45 | 63 degrees |
| Film 46 | 68 degrees |
| Film 47 | 63 degrees |
| Film 48 | 66 degrees |
| Film 49 | 65 degrees |
| Film 50 | 69 degrees |
| Film 51 | 69 degrees |
| Film 52 | 68 degrees |

TABLE 8

| No. | Contact angle |
| --- | --- |
| Film 1 | 52 degrees |
| Film 2 | 43 degrees |
| Film 3 | 43 degrees |
| Film 4 | 48 degrees |
| Film 5 | 46 degrees |
| Film 6 | 42 degrees |
| Film 7 | 44 degrees |
| Film 8 | 48 degrees |
| Film 9 | 44 degrees |
| Film 10 | 42 degrees |
| Film 11 | 49 degrees |
| Film 12 | 53 degrees |
| Film 13 | 46 degrees |
| Film 14 | 54 degrees |
| Film 15 | 51 degrees |
| Film 16 | 41 degrees |
| Film 17 | 45 degrees |
| Film 18 | 48 degrees |
| Film 19 | 55 degrees |
| Film 20 | 50 degrees |
| Film 21 | 41 degrees |
| Film 22 | 52 degrees |
| Film 23 | 38 degrees |
| Film 24 | 42 degrees |
| Film 25 | 43 degrees |
| Film 26 | 40 degrees |
| Film 27 | 50 degrees |
| Film 28 | 47 degrees |
| Film 29 | 44 degrees |
| Film 30 | 54 degrees |
| Film 31 | 46 degrees |
| Film 32 | 46 degrees |
| Film 33 | 43 degrees |
| Film 34 | 41 degrees |
| Film 35 | 53 degrees |
| Film 36 | 47 degrees |
| Film 37 | 50 degrees |
| Film 38 | 41 degrees |
| Film 39 | 45 degrees |
| Film 40 | 45 degrees |
| Film 41 | 49 degrees |
| Film 42 | 47 degrees |
| Film 43 | 46 degrees |
| Film 44 | 39 degrees |
| Film 45 | 39 degrees |
| Film 46 | 53 degrees |
| Film 47 | 39 degrees |
| Film 48 | 48 degrees |
| Film 49 | 41 degrees |
| Film 50 | 47 degrees |
| Film 51 | 59 degrees |
| Film 52 | 67 degrees |

TABLE 9

| No. | Contact angle | No. | Contact angle |
| --- | --- | --- | --- |
| Unexposed PR-3 | 71 degrees | Exposed PR-3 | 52 degrees |

TABLE 10

| Polymer No. | Polymer (Parts by mass) | Acid generator (Parts by mass) | Base (Parts by mass) | Water-repellent polymer (Parts by mass) | Solvent (Parts by mass) |
| --- | --- | --- | --- | --- | --- |
| PR-1 | ArF resist polymer 1 (100) | PAG 1 (7.0) | Quencher (1.0) | None | PGMEA (2,500) |
| PR-2 | ArF resist polymer 1 (100) | PAG 1 (10.0) | Quencher (2.0) | Water-repellent polymer 1 (4.0) | PGMEA (2,500) |

ArF Resist Polymer 1:

Molecular weight (Mw): 7,800

Dispersity (Mw/Mn): 1.78

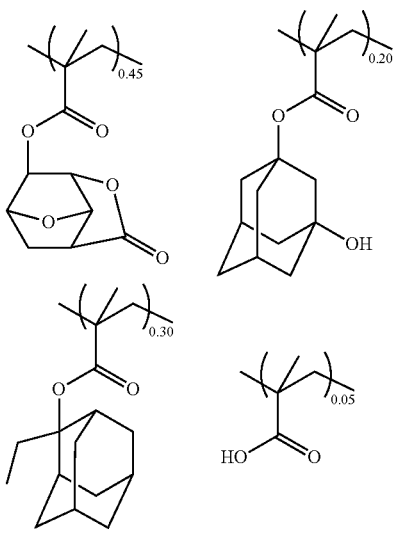

Acid Generator: PAG 1

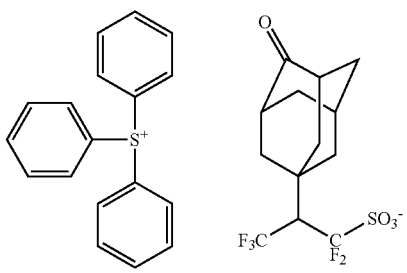

Base: Quencher

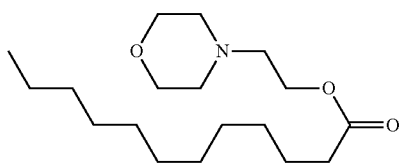 [SMILES: CCCCCCCCCCCC(=O)OCCN1CCOCC1]

Water Repellent Polymer 1:
Molecular weight (Mw): 8,200
Dispersity (Mw/Mn): 1.67

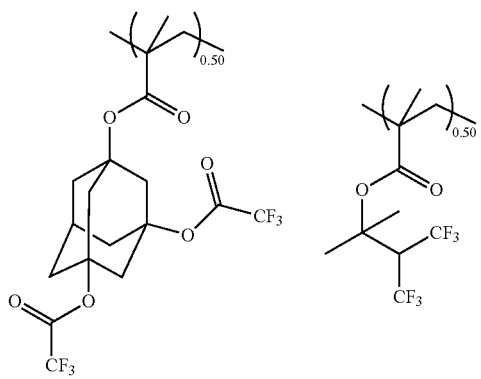

TABLE 11

|  | Polymer (Parts by mass) | Organic solvent (Parts by mass) |
| --- | --- | --- |
| TC-1 | Top coat polymer (100) | Diisoamyl ether (2700) 2-Methyl-1-butanol (270) |

Top Coat Polymer:
Molecular weight (Mw): 8,800
Dispersity (Mw/Mn): 1.69

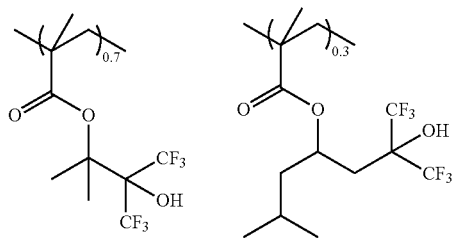

D. Patterning Test by Positive Development

Firstly, spin-on-carbon film ODL-50 (carbon content of 80% by mass, manufactured by Shin-Etsu Chemical Co., Ltd.) having film thickness of 200 nm was formed on a silicon wafer. Then, each of the silicon-containing resist underlayer film compositions Sol. 11 to Sol. 52 was applied thereonto and then baked at 240° C. for 60 seconds to form the silicon-containing film having film thickness of 35 nm (Film 11 to Film 52).

Subsequently, the ArF resist solution for positive development (PR-1) shown in Table 10 was applied on the silicon-containing film; and then, it was baked at 110° C. for 60 seconds to form the photoresist film having the film thickness of 100 nm. Further on this photoresist film was applied the immersion top coat (TC-1) shown in Table 11; and then, it was baked at 90° C. for 60 seconds to form the top coat having film thickness of 50 nm.

Separately, the ArF resist solution for positive development (PR-2) shown in Table 10 was applied on the silicon-containing film; and then, it was baked at 110° C. for 60 seconds to form the photoresist film having the film thickness of 100 nm.

Then, after these were exposed by using ArF immersion exposure instrument NSR-S610C (NA of 1.30, σ of 0.98/0.65, 35-degree dipole polarized illumination, and 6% half tone phase shift mask, manufactured by Nikon Corp.), baking (PEB) was done at 100° C. for 60 seconds, which was then followed by development with an aqueous tetramethyl ammonium hydroxide (TMAH) solution with the concentration thereof being 2.38% by mass for 30 seconds to obtain a 43-nm 1:1 positive line-and-space pattern.

With this dimension, pattern fall was measured by using electron microscope CG4000 (manufactured by Hitachi High-Technologies Corp.), and cross section form was measured by using electron microscope S-9380 (manufactured by Hitachi, Ltd.) (Table 12-1 and Table 12-2).

TABLE 12-1

|  | Silicon-containing resist underlayer film | ArF resist | Pattern cross section form after development | Pattern fall | CA1-CA2 |
| --- | --- | --- | --- | --- | --- |
| Example 1-1 | Film 11 | PR-1 | Vertical form | None | 5 degrees |
| Example 1-2 | Film 12 | PR-1 | Vertical form | None | 8 degrees |
| Example 1-3 | Film 13 | PR-1 | Vertical form | None | 2 degrees |
| Example 1-4 | Film 14 | PR-1 | Vertical form | None | 10 degrees |
| Example 1-5 | Film 15 | PR-1 | Vertical form | None | 4 degrees |
| Example 1-6 | Film 16 | PR-1 | Vertical form | None | 4 degrees |
| Example 1-7 | Film 17 | PR-1 | Vertical form | None | 3 degrees |
| Example 1-8 | Film 18 | PR-1 | Vertical form | None | 6 degrees |
| Example 1-9 | Film 19 | PR-1 | Vertical form | None | 7 degrees |
| Example 1-10 | Film 20 | PR-1 | Vertical form | None | 9 degrees |
| Example 1-11 | Film 21 | PR-1 | Vertical form | None | 6 degrees |
| Example 1-12 | Film 22 | PR-1 | Vertical form | None | 10 degrees |
| Example 1-13 | Film 23 | PR-1 | Vertical form | None | 9 degrees |
| Example 1-14 | Film 24 | PR-1 | Vertical form | None | 7 degrees |
| Example 1-15 | Film 25 | PR-1 | Vertical form | None | 5 degrees |
| Example 1-16 | Film 26 | PR-1 | Vertical form | None | 8 degrees |
| Example 1-17 | Film 27 | PR-1 | Vertical form | None | 4 degrees |
| Example 1-18 | Film 28 | PR-1 | Vertical form | None | 6 degrees |
| Example 1-19 | Film 29 | PR-1 | Vertical form | None | 5 degrees |
| Example 1-20 | Film 30 | PR-1 | Vertical form | None | 3 degrees |

TABLE 12-2

| | Silicon-containing resist underlayer film | ArF resist | Pattern cross section form after development | Pattern fall | CA1-CA2 |
|---|---|---|---|---|---|
| Example 1-21 | Film 31 | PR-1 | Vertical form | None | 4 degrees |
| Example 1-22 | Film 32 | PR-1 | Vertical form | None | 5 degrees |
| Example 1-23 | Film 33 | PR-1 | Vertical form | None | 5 degrees |
| Example 1-24 | Film 34 | PR-1 | Vertical form | None | 10 degrees |
| Example 1-25 | Film 35 | PR-1 | Vertical form | None | 4 degrees |
| Example 1-26 | Film 36 | PR-1 | Vertical form | None | 4 degrees |
| Example 1-27 | Film 37 | PR-1 | Vertical form | None | 3 degrees |
| Example 1-28 | Film 38 | PR-1 | Vertical form | None | 2 degrees |
| Example 1-29 | Film 39 | PR-1 | Vertical form | None | 4 degrees |
| Example 1-30 | Film 40 | PR-1 | Vertical form | None | 6 degrees |
| Example 1-31 | Film 41 | PR-1 | Vertical form | None | 3 degrees |
| Example 1-32 | Film 42 | PR-1 | Vertical form | None | 9 degrees |
| Example 1-33 | Film 43 | PR-1 | Vertical form | None | 3 degrees |
| Example 1-34 | Film 44 | PR-1 | Vertical form- | None | 9 degrees |
| Example 1-35 | Film 45 | PR-1 | Vertical form | None | 3 degrees |
| Example 1-36 | Film 46 | PR-1 | Vertical form | None | 10 degrees |
| Example 1-37 | Film 47 | PR-1 | Vertical form | None | 7 degrees |
| Example 1-38 | Film 48 | PR-1 | Vertical form | None | 3 degrees |
| Example 1-39 | Film 49 | PR-1 | Vertical form | None | 7 degrees |
| Example 1-40 | Film 50 | PR-1 | Vertical form | None | 9 degrees |
| Example 1-41 | Film 51 | PR-1 | Vertical form | None | 10 degrees |
| Comparative Example 1-1 | Film 52 | PR-1 | Vertical form | None | 9 degrees |

As shown in Table 12-1 and Table 12-2, when the silicon-containing film whose amount of change between contact angle of the silicon-containing film (CA1) and contact angle of the silicon-containing film after coating of the upper layer resist for positive development and removal thereof (CA2) is 10 degrees or less was used, a resist cross section of a vertical form could be obtained in the positive development. In addition, it was confirmed that there was no pattern fall.

E. Patterning Test by Negative Development

Firstly, spin-on-carbon film ODL-50 (carbon content of 80% by mass, manufactured by Shin-Etsu Chemical Co., Ltd.) having film thickness of 200 nm was formed on a silicon wafer. Then, each of the silicon-containing resist underlayer film compositions Sol. 11 to Sol. 52 was applied thereonto and then baked at 240° C. for 60 seconds to form the silicon-containing film having film thickness of 35 nm (Film 11 to Film 52).

Subsequently, the ArF resist solution for negative development (PR-3) shown in Table 13 was applied on the silicon-containing film; and then, it was baked at 100° C. for 60 seconds to form the photoresist film having film thickness of 100 nm. On this photoresist film was applied the immersion top coat (TC-1) shown in Table 11; and then, it was baked at 90° C. for 60 seconds to form the top coat having film thickness of 50 nm.

Separately, the ArF resist solution for negative development (PR-4 and PR-5) shown in Table 13 was applied on the silicon-containing film; and then, it was baked at 110° C. for 60 seconds to form the photoresist film having film thickness of 100 nm.

Then, after it was exposed by using ArF immersion exposure instrument NSR-S610C (NA of 1.30, σ of 0.98/0.65, 35-degree dipole polarized illumination, and 6% half tone phase shift mask, manufactured by Nikon Corp.) and then baked at 100° C. for 60 seconds (PEB), a butyl acetate development solution was discharged for 3 seconds from a developer nozzle with rotation speed of 30 rpm; and thereafter, rotation was stopped, and then puddle development was done for 27 seconds. After rinsing thereof by diisoamyl ether, it was spin-dried and then baked at 100° C. for 20 seconds to evaporate the rinse solvent.

By this patterning, a 43-nm 1:1 negative line-and-space pattern was obtained. With this dimension, pattern fall was measured by using electron microscope CG4000 (manufactured by Hitachi High-Technologies Corp.), and cross section form was measured by using electron microscope S-4700 (manufactured by Hitachi, Ltd.) (Table 14-1 and Table 14-2).

TABLE 13

| | Polymer (Parts by mass) | Acid generator (Parts by mass) | Base (Parts by mass) | Water-repellent polymer (Parts by mass) | Solvent (Parts by mass) |
|---|---|---|---|---|---|
| PR-3 | ArF resist polymer 2 (100) | PAG 2 (7.0) | Quencher (1.0) | None | PGMEA (2,500) |
| PR-4 | ArF resist polymer 3 (100) | PAG 2 (7.0) | Quencher (1.0) | None | PGMEA (2,500) |
| PR-5 | ArF resist polymer 3 (100) | PAG 2 (10.0) | Quencher (2.0) | Water-repellent polymer 1 (4.0) | PGMEA (2,500) |

ArF Resist Polymer 2:

Molecular weight (Mw): 8,600

Dispersity (Mw/Mn): 1.88

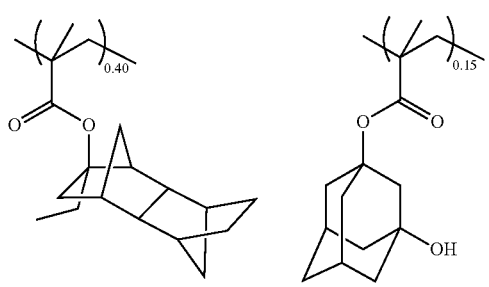

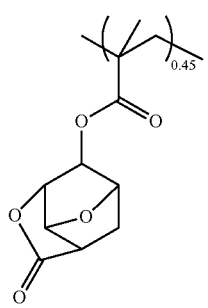

ArF Resist Polymer 3:
 Molecular weight (Mw): 8,900
 Dispersity (Mw/Mn): 1.93

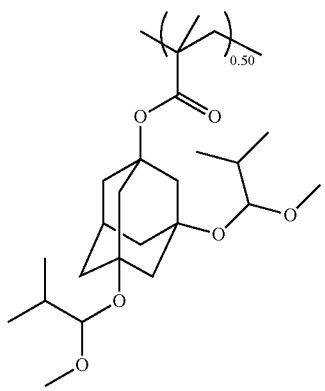

Acid Generator: PAG 2

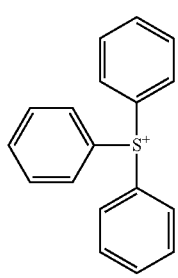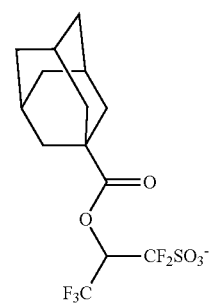

Base: Quencher

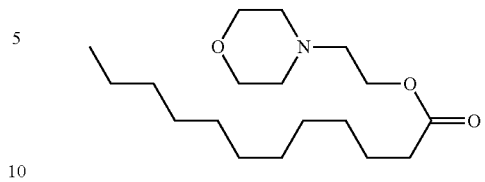

TABLE 14-1

| | Silicon-containing resist underlayer film | ArF resist | Pattern cross section form after development | Pattern fall | CA3-CA4 |
|---|---|---|---|---|---|
| Example 2-1 | Film 11 | PR-3 | Vertical form | None | 20 degrees |
| Example 2-2 | Film 12 | PR-3 | Vertical form | None | 15 degrees |
| Example 2-3 | Film 13 | PR-3 | Vertical form | None | 17 degrees |
| Example 2-4 | Film 14 | PR-3 | Vertical form | None | 15 degrees |
| Example 2-5 | Film 15 | PR-3 | Vertical form | None | 15 degrees |
| Example 2-6 | Film 16 | PR-3 | Vertical form | None | 24 degrees |
| Example 2-7 | Film 17 | PR-3 | Vertical form | None | 22 degrees |
| Example 2-8 | Film 18 | PR-3 | Vertical form | None | 20 degrees |
| Example 2-9 | Film 19 | PR-3 | Vertical form | None | 15 degrees |
| Example 2-10 | Film 20 | PR-3 | Vertical form | Hone | 19 degrees |
| Example 2-11 | Film 21 | PR-3 | Vertical form | None | 22 degrees |
| Example 2-12 | Film 22 | PR-3 | Vertical form | None | 17 degrees |
| Example 2-13 | Film 23 | PR-3 | Vertical form | None | 23 degrees |
| Example 2-14 | Film 24 | PR-3 | Vertical form | None | 21 degrees |
| Example 2-15 | Film 25 | PR-3 | Vertical form | None | 22 degrees |
| Example 2-16 | Film 26 | PR-3 | Vertical form | None | 24 degrees |
| Example 2-17 | Film 27 | PR-3 | Vertical form | None | 19 degrees |
| Example 2-18 | Film 28 | PR-3 | Vertical form | None | 17 degrees |
| Example 2-19 | Film 29 | PR-3 | Vertical form | None | 22 degrees |
| Example 2-20 | Film 30 | PR-3 | Vertical form | None | 15 degrees |

TABLE 14-2

| | Silicon-containing resist underlayer film | ArF resist | Pattern cross section form after development | Pattern fall | CA3-CA4 |
|---|---|---|---|---|---|
| Example 2-21 | Film 31 | PR-3 | Vertical form | None | 16 degrees |
| Example 2-22 | Film 32 | PR-3 | Vertical form | None | 23 degrees |
| Example 2-23 | Film 33 | PR-3 | Vertical form | None | 23 degrees |

TABLE 14-2-continued

| | Silicon-containing resist underlayer film | ArF resist | Pattern cross section form after development | Pattern fall | CA3-CA4 |
|---|---|---|---|---|---|
| Example 2-24 | Film 34 | PR-3 | Vertical form | None | 24 degrees |
| Example 2-25 | Film 35 | PR-3 | Vertical form | None | 18 degrees |
| Example 2-26 | Film 36 | PR-3 | Vertical form | None | 21 degrees |
| Example 2-27 | Film 37 | PR-3 | Vertical form | None | 17 degrees |
| Example 2-28 | Film 38 | PR-3 | Vertical form | None | 21 degrees |
| Example 2-29 | Film 39 | PR-3 | Vertical form | None | 23 degrees |
| Example 2-30 | Film 40 | PR-3 | Vertical form | None | 22 degrees |
| Example 2-31 | Film 41 | PR-3 | Vertical form | None | 18 degrees |
| Example 2-32 | Film 42 | PR-3 | Vertical form | None | 15 degrees |
| Example 2-33 | Film 43 | PR-3 | Vertical form | None | 22 degrees |
| Example 2-34 | Film 44 | PR-3 | Vertical form | None | 24 degrees |
| Example 2-35 | Film 45 | PR-3 | Vertical form | None | 24 degrees |
| Example 2-36 | Film 46 | PR-3 | Vertical form | None | 15 degrees |
| Example 2-37 | Film 47 | PR-3 | Vertical form | None | 24 degrees |
| Example 2-38 | Film 48 | PR-3 | Vertical form | None | 18 degrees |
| Example 2-39 | Film 49 | PR-3 | Vertical form | None | 24 degrees |
| Example 2-40 | Film 50 | PR-3 | Vertical form | None | 22 degrees |
| Example 2-41 | Film 51 | PR-3 | Vertical form | None | 10 degrees |
| Comparative Example 2-1 | Film 52 | PR-3 | Vertical form | Pattern fall | 1 degree |

As shown in Table 14-1 and Table 14-2, when the resist underlayer film whose amount of change between contact angle of the silicon-containing film after coating and removal of the upper layer resist for negative development (CA3) and contact angle of the silicon-containing film after coating, photo-exposure, and removal of the upper layer resist for negative development (CA4) is 10 degree or more was used, a resist cross section of a vertical form could be obtained in the negative development. It was also confirmed that there was no pattern fall. In addition, especially from Example 2-1 and Example 2-41, it was demonstrated that, if ratio of the four-functional unit (Monomer 102) in the polysiloxane is 70 mole %, the silicon-containing surface modifier of the present invention is readily localized on surface thereof during film formation whereby increasing change of the contact angle after photo-exposure.

On the other hand, in negative development in Comparative Examples 2-1 in which an organic group substituted with an acid-labile group is not contained therein, amount of change in contact angle was so small, resulting in causing of pattern fall.

F. Patterning Test: Developer

By using the developers shown below in place of the developer in Examples 2 (butyl acetate), a 43-nm 1:1 negative line-and-space pattern (Examples 3) was obtained in the manner similar to those in Examples 2 (Table 15).

TABLE 15

| | Silicon-containing film | ArF resist | Developer | Pattern cross section form after development | Pattern fall |
|---|---|---|---|---|---|
| Example 3-1 | Film 11 | PR-3 | 2-Heptanone | Vertical form | None |
| Example 3-2 | Film 11 | PR-3 | Methyl benzoate | Vertical form | None |
| Example 3-3 | Film 11 | PR-4 | Ethyl benzoate | Vertical form | None |
| Example 3-4 | Film 11 | PR-4 | Phenyl acetate | Vertical form | None |
| Example 3-5 | Film 11 | PR-5 | Benzyl acetate | Vertical form | None |
| Example 3-6 | Film 11 | PR-5 | Methyl phenylacetate | Vertical form | None |

As shown in Table 15, with any of these developers, a resist pattern having cross section of a vertical form could be obtained.

G. Pattern Etching Test: Positive Development Pattern

By using the resist pattern by positive development formed in the forgoing patterning test by positive development as a mask, the silicon-containing film was dry etched under the condition (1), and then, the pattern was transferred to the spin-on-carbon film by dry etching under the condition (2). The cross section form of the obtained pattern was measured by using electron microscope S-9380 (manufactured by Hitachi, Ltd.), and the pattern roughness was measured by using electron microscope CG4000 (manufactured by Hitachi High-Technologies Corp.). The results are summarized in Table 16-1 and Table 16-2 for comparison.

(1) Etching Condition in the $CHF_3/CF_4$ Gas System

Instrument: dry etching instrument Telius SP (manufactured by Tokyo Electron Ltd.)

Etching condition (1):

| Chamber pressure | 15 Pa |
|---|---|
| Upper/lower RF power | 500 W/300 W |
| $CHF_3$ gas flow rate | 50 mL/minute |
| $CF_4$ gas flow rate | 150 mL/minute |
| Ar gas flow rate | 100 mL/minute |
| Treatment time | 40 seconds |

(2) Etching Condition in the $O_2/N_2$ Gas System

Instrument: dry etching instrument Telius SP (manufactured by Tokyo Electron Ltd.)

Etching condition (2):

| Chamber pressure | 5 Pa |
|---|---|
| Upper/lower RF power | 1000 W/300 W |
| $O_2$ gas flow rate | 300 mL/minute |
| $N_2$ gas flow rate | 100 mL/minute |
| Ar gas flow rate | 100 mL/minute |
| Treatment time | 30 seconds |

TABLE 16-1

| | Silicon-containing film | ArF resist | Pattern cross section form of spin-on-carbon film after dry etching | Pattern roughness |
|---|---|---|---|---|
| Example 4-1 | Film 11 | PR-1 | Vertical form | 1.9 nm |
| Example 4-2 | Film 12 | PR-1 | Vertical form | 1.6 nm |
| Example 4-3 | Film 13 | PR-1 | Vertical form | 1.9 nm |
| Example 4-4 | Film 14 | PR-1 | Vertical form | 1.9 nm |
| Example 4-5 | Film 15 | PR-1 | Vertical form | 1.7 nm |
| Example 4-6 | Film 16 | PR-1 | Vertical form | 1.9 nm |
| Example 4-7 | Film 17 | PR-1 | Vertical form | 2.0 nm |

TABLE 16-1-continued

| | Silicon-containing film | ArF resist | Pattern cross section form of spin-on-carbon film after dry etching | Pattern roughness |
|---|---|---|---|---|
| Example 4-8 | Film 18 | PR-1 | Vertical form | 1.5 nm |
| Example 4-9 | Film 19 | PR-1 | Vertical form | 1.7 nm |
| Example 4-10 | Film 20 | PR-1 | Vertical form | 1.7 nm |
| Example 4-11 | Film 21 | PR-2 | Vertical form | 1.5 nm |
| Example 4-12 | Film 22 | PR-2 | Vertical form | 1.6 nm |
| Example 4-13 | Film 23 | PR-2 | Vertical form | 1.5 nm |
| Example 4-14 | Film 24 | PR-2 | Vertical form | 1.9 nm |
| Example 4-15 | Film 25 | PR-2 | Vertical form | 1.7 nm |
| Example 4-16 | Film 26 | PR-2 | Vertical form | 1.8 nm |
| Example 4-17 | Film 27 | PR-2 | Vertical form | 1.6 nm |
| Example 4-18 | Film 28 | PR-2 | Vertical form | 2.2 nm |
| Example 4-19 | Film 29 | PR-2 | Vertical form | 2.1 nm |
| Example 4-20 | Film 30 | PR-2 | Vertical form | 1.6 nm |

TABLE 16-2

| | Silicon-containing film | ArF resist | Pattern cross section form of spin-on-carbon film after dry etching | Pattern roughness |
|---|---|---|---|---|
| Example 4-21 | Film 31 | PR-1 | Vertical form | 1.8 nm |
| Example 4-22 | Film 32 | PR-1 | Vertical form | 1.7 nm |
| Example 4-23 | Film 33 | PR-1 | Vertical form | 1.9 nm |
| Example 4-24 | Film 34 | PR-1 | Vertical form | 1.8 nm |
| Example 4-25 | Film 35 | PR-1 | Vertical form | 2.2 nm |
| Example 4-26 | Film 36 | PR-1 | Vertical form | 1.6 nm |
| Example 4-27 | Film 37 | PR-1 | Vertical form | 2.0 nm |
| Example 4-28 | Film 38 | PR-1 | Vertical form | 1.6 nm |
| Example 4-29 | Film 39 | PR-1 | Vertical form | 2.0 nm |
| Example 4-30 | Film 40 | PR-1 | Vertical form | 1.6 nm |
| Example 4-31 | Film 41 | PR-1 | Vertical form | 1.6 nm |
| Example 4-32 | Film 42 | PR-1 | Vertical form | 2.0 nm |
| Example 4-33 | Film 43 | PR-1 | Vertical form | 2.0 nm |
| Example 4-34 | Film 44 | PR-1 | Vertical form | 1.6 nm |
| Example 4-35 | Film 45 | PR-1 | Vertical form | 1.5 nm |
| Example 4-36 | Film 46 | PR-1 | Vertical form | 1.6 nm |
| Example 4-37 | Film 47 | PR-1 | Vertical form | 1.8 nm |
| Example 4-38 | Film 48 | PR-1 | Vertical form | 2.0 nm |
| Example 4-39 | Film 49 | PR-1 | Vertical form | 1.8 nm |
| Example 4-40 | Film 50 | PR-1 | Vertical form | 1.9 nm |

In the present invention, as shown in Table 16-1 and Table 16-2, it was confirmed that the resist form after development and the cross section form and the pattern roughness after processing of the spin-on-carbon film were excellent.

H. Pattern Etching Test: Negative Development Pattern

By using the resist pattern by negative development formed in the forgoing patterning test by negative development as a mask, the silicon-containing film was dry etched under the condition (1), and then, the pattern was transferred to the spin-on-carbon film by dry etching under the condition (2). The cross section form of the obtained pattern was measured by using electron microscope S-9380 (manufactured by Hitachi, Ltd.), and the pattern roughness was measured by using electron microscope CG4000 (manufactured by Hitachi High-Technologies Corp.). The results are summarized in Table 17-1 and Table 17-2 for comparison.

TABLE 17-1

| | Silicon-containing film | ArF resist | Pattern cross section form of spin-on-carbon film after dry etching | Pattern roughness |
|---|---|---|---|---|
| Example 5-1 | Film 11 | PR-3 | Vertical form | 1.7 nm |
| Example 5-2 | Film 12 | PR-3 | Vertical form | 1.6 nm |
| Example 5-3 | Film 13 | PR-3 | Vertical form | 2.1 nm |
| Example 5-4 | Film 14 | PR-3 | Vertical form | 1.6 nm |
| Example 5-5 | Film 15 | PR-3 | Vertical form | 2.2 nm |
| Example 5-6 | Film 16 | PR-3 | Vertical form | 1.9 nm |
| Example 5-7 | Film 17 | PR-3 | Vertical form | 1.8 nm |
| Example 5-8 | Film 18 | PR-3 | Vertical form | 1.9 nm |
| Example 5-9 | Film 19 | PR-3 | Vertical form | 1.9 nm |
| Example 5-10 | Film 20 | PR-3 | Vertical form | 1.6 nm |
| Example 5-11 | Film 21 | PR-4 | Vertical form | 1.8 nm |
| Example 5-12 | Film 22 | PR-4 | Vertical form | 1.5 nm |
| Example 5-13 | Film 23 | PR-4 | Vertical form | 2.1 nm |
| Example 5-14 | Film 24 | PR-4 | Vertical form | 1.9 nm |
| Example 5-15 | Film 25 | PR-4 | Vertical form | 1.6 nm |
| Example 5-16 | Film 26 | PR-4 | Vertical form | 2.1 nm |
| Example 5-17 | Film 27 | PR-4 | Vertical form | 1.9 nm |
| Example 5-18 | Film 28 | PR-4 | Vertical form | 1.6 nm |
| Example 5-19 | Film 29 | PR-4 | Vertical form | 1.9 nm |
| Example 5-20 | Film 30 | PR-4 | Vertical form | 1.9 nm |

TABLE 17-2

| | Silicon-containing film | ArF resist | Pattern cross section form of spin-on-carbon film after dry etching | Pattern roughness |
|---|---|---|---|---|
| Example 5-21 | Film 31 | PR-5 | Vertical form | 1.8 nm |
| Example 5-22 | Film 32 | PR-5 | Vertical form | 1.5 nm |
| Example 5-23 | Film 33 | PR-5 | Vertical form | 2.0 nm |
| Example 5-24 | Film 34 | PR-5 | Vertical form | 1.8 nm |
| Example 5-25 | Film 35 | PR-5 | Vertical form | 1.9 nm |
| Example 5-26 | Film 36 | PR-5 | Vertical form | 1.8 nm |
| Example 5-27 | Film 37 | PR-5 | Vertical form | 1.7 nm |
| Example 5-28 | Film 38 | PR-5 | Vertical form | 2.1 nm |
| Example 5-29 | Film 39 | PR-3 | Vertical form | 1.8 nm |
| Example 5-30 | Film 40 | PR-3 | Vertical form | 1.8 nm |
| Example 5-31 | Film 41 | PR-5 | Vertical form | 1.7 nm |
| Example 5-32 | Film 42 | PR-5 | Vertical form | 2.0 nm |
| Example 5-33 | Film 43 | PR-5 | Vertical form | 1.8 nm |
| Example 5-34 | Film 44 | PR-5 | Vertical form | 1.8 nm |
| Example 5-35 | Film 45 | PR-5 | Vertical form | 2.2 nm |
| Example 5-36 | Film 46 | PR-5 | Vertical form | 2.0 nm |
| Example 5-37 | Film 47 | PR-5 | Vertical form | 1.8 nm |
| Example 5-38 | Film 48 | PR-5 | Vertical form | 2.0 nm |
| Example 5-39 | Film 49 | PR-3 | Vertical form | 2.0 nm |
| Example 5-40 | Film 50 | PR-3 | Vertical form | 1.9 nm |

In the present invention, as shown in Table 17-1 and Table 17-2, it was confirmed that the resist form after development and the cross section form and the pattern roughness after processing of the spin-on-carbon film were excellent.

It must be noted here that the present invention is not limited to the embodiments as described above. The foregoing embodiments are mere examples; any form having substantially the same composition as the technical concept described in claims of the present invention and showing similar effects is included in the technical scope of the present invention.

EXPLANATION OF REFERENCE NUMERALS

1 Body to be processed
1*a* Negative pattern
1*b* Positive pattern
2 Organic underlayer film
2*a* Negative organic underlayer film pattern
2*b* Positive organic underlayer film pattern 3 Silicon-containing resist underlayer film
3a Negative silicon-containing resist underlayer film pattern
3b Positive silicon-containing resist underlayer film pattern
4 Photoresist film
4a Negative resist pattern
4b Positive resist pattern

What is claimed is:

1. A silicon-containing resist underlayer film composition, comprising:
   a polysiloxane compound as a base polymer; and
   a silicon-containing surface modifier that contains one or more of a repeating unit shown by the following general formula (A) and a partial structure shown by the following general formula (C):

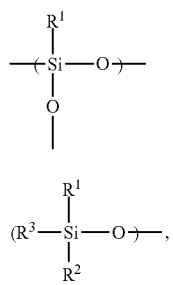

where in the formulae, $R^1$ represents an organic group having a hydroxyl group or a carboxylic acid group, the groups being substituted with an acid-labile group; and each of $R^2$ and $R^3$ independently represents a group identical to $R^1$, a hydrogen atom, or a monovalent organic group having 1 to 30 carbon atoms,
   wherein a blending amount of the silicon-containing surface modifier in the silicon-containing resist underlayer film composition is 0.1 to 10 parts by mass with respect to 100 parts by mass of the polysiloxane compound.

2. The silicon-containing resist underlayer film according to claim 1, wherein the silicon-containing surface modifier further contains a repeating unit shown by the following general formula (B):

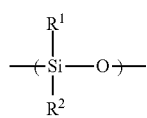

wherein $R^1$ and $R^2$ represent the same meanings as before.

3. The silicon-containing resist underlayer film according to claim 2, wherein the acid-labile group in the foregoing $R^1$ is an acetal group or a tertiary alkyl group.

4. The silicon-containing resist underlayer film composition according to claim 3, wherein, a content of a component derived from a four-functional hydrolysable monomer in the polysiloxane compound is 70 mole % or more.

5. The silicon-containing resist underlayer film composition according to claim 4, wherein the silicon-containing resist underlayer film composition contains a solvent having a boiling point of 180° C. or higher.

6. The silicon-containing resist underlayer film composition according to claim 3, wherein the silicon-containing resist underlayer film composition contains a solvent having a boiling point of 180° C. or higher.

7. The silicon-containing resist underlayer film composition according to claim 2, wherein a content of a component derived from a four-functional hydrolysable monomer in the polysiloxane compound is 70 mole % or more.

8. The silicon-containing resist underlayer film composition according to claim 7, wherein the silicon-containing resist underlayer film composition contains a solvent having a boiling point of 180° C. or higher.

9. The silicon-containing resist underlayer film composition according to claim 2, wherein the silicon-containing resist underlayer film composition contains a solvent having a boiling point of 180° C. or higher.

10. The silicon-containing resist underlayer film according to claim 1, wherein the acid-labile group in the foregoing $R^1$ is an acetal group or a tertiary alkyl group.

11. The silicon-containing resist underlayer film composition according to claim 10, wherein a content of a component derived from a four-functional hydrolysable monomer in the polysiloxane compound is 70 mole % or more.

12. The silicon-containing resist underlayer film composition according to claim 11, wherein the silicon-containing resist underlayer film composition contains a solvent having a boiling point of 180° C. or higher.

13. The silicon-containing resist underlayer film composition according to claim 10, wherein the silicon-containing resist underlayer film composition contains a solvent having a boiling point of 180° C. or higher.

14. The silicon-containing resist underlayer film composition according to claim 1, wherein a content of a component derived from a four-functional hydrolysable monomer in the polysiloxane compound is 70 mole % or more.

15. The silicon-containing resist underlayer film composition according to claim 14, wherein the silicon-containing resist underlayer film composition contains a solvent having a boiling point of 180° C. or higher.

16. The silicon-containing resist underlayer film composition according to claim 1, wherein the silicon-containing resist underlayer film composition contains a solvent having a boiling point of 180° C. or higher.

17. A patterning process, comprising:
   forming an organic underlayer film on a body to be processed by using an application-type organic underlayer film composition;
   forming a silicon-containing resist underlayer film on the organic underlayer film by using the silicon-containing resist underlayer film composition according to claim 1;
   forming a photo resist film on the silicon-containing resist underlayer film by using a chemically amplifying type resist composition, and after applying heat treatment, exposing the photo resist film to a high energy beam;
   forming a positive pattern by dissolving an exposed area of the photo resist film by using an alkaline developer;
   transferring the pattern to the silicon-containing resist underlayer film by dry etching by using the photo resist film formed with the pattern as a mask;
   transferring the pattern by dry etching the organic underlayer film by using the silicon-containing resist underlayer film transferred with the pattern as a mask; and then
   transferring the pattern to the body to be processed by dry etching by using the organic underlayer film transferred with the pattern as a mask.

18. The patterning process according to claim 17, wherein the body to be processed is a substrate for a semiconductor device or a substrate for a semiconductor device coated with any of a metal film, a metal alloy film, a metal carbide film, a metal oxide film, a metal nitride film, a metal oxide carbide film, and a metal oxide nitride film.

19. The patterning process according to claim 18, wherein the metal that constitutes the body to be processed is any of silicon, gallium, titanium, tungsten, hafnium, zirconium, chromium, germanium, copper, aluminum, and iron, or a metal alloy thereof.

20. A patterning process, comprising:
forming an organic hard mask mainly composed of carbon on a body to be processed by a CVD method;
forming a silicon-containing resist underlayer film on the organic hard mask by using the silicon-containing resist underlayer film composition according to claim 1,
forming a photo resist film on the silicon-containing resist underlayer film by using a chemically amplifying type resist composition, and after applying heat treatment, exposing the photo resist film to a high energy beam;
forming a positive pattern by dissolving an exposed area of the photo resist film by using an alkaline developer;
transferring the pattern to the silicon-containing resist underlayer film by dry etching by using the photo resist film formed with the pattern as a mask;
transferring the pattern by dry etching the organic hard mask by using the silicon-containing resist underlayer film transferred with the pattern as a mask; and then
transferring the pattern to the body to be processed by dry etching by using the organic hard mask transferred with the pattern as a mask.

21. A patterning process, comprising:
forming an organic underlayer film on a body to be processed by using an application-type organic underlayer film composition;
forming a silicon-containing resist underlayer film on the organic underlayer film by using the silicon-containing resist underlayer film composition according to claim 1;
forming a photo resist film on the silicon-containing resist underlayer film by using a chemically amplifying type resist composition, and after applying heat treatment, exposing the photo resist film to a high energy beam;
forming a negative pattern by dissolving an unexposed area of the photo resist film by using an organic solvent developer;
transferring the pattern to the silicon-containing resist underlayer film by dry etching by using the photo resist film formed with the pattern as a mask;
transferring the pattern by dry etching the organic underlayer film by using the silicon-containing resist underlayer film transferred with the pattern as a mask; and then
transferring the pattern to the body to be processed by dry etching by using the organic underlayer film transferred with the pattern as a mask.

22. A patterning process, comprising:
forming an organic hard mask mainly composed of carbon on a body to be processed by a CVD method;
forming a silicon-containing resist underlayer film on the organic hard mask by using the silicon-containing resist underlayer film composition according to claim 1;
forming a photo resist film on the silicon-containing resist underlayer film by using a chemically amplifying type resist composition, and after applying heat treatment, exposing the photo resist film to a high energy beam;
forming a negative pattern by dissolving an unexposed area of the photo resist film by using an organic solvent developer;
transferring the pattern to the silicon-containing resist underlayer film by dry etching by using the photo resist film formed with the pattern as a mask;
transferring the pattern by dry etching the organic hard mask by using the silicon-containing resist underlayer film transferred with the pattern as a mask; and then
transferring the pattern to the body to be processed by dry etching by using the organic hard mask transferred with the pattern as a mask.

\* \* \* \* \*